(12) United States Patent
Cao

(10) Patent No.: US 12,257,309 B2
(45) Date of Patent: Mar. 25, 2025

(54) ZWITTERIONIC POLYMER-INSULIN COMPOSITIONS AND RELATED METHODS

(71) Applicant: Wayne State University, Detroit, MI (US)

(72) Inventor: Zhiqiang Cao, Troy, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 17/569,129

(22) Filed: Jan. 5, 2022

(65) Prior Publication Data

US 2022/0125937 A1    Apr. 28, 2022

Related U.S. Application Data

(62) Division of application No. 16/478,352, filed as application No. PCT/US2018/014038 on Jan. 17, 2018, now abandoned.

(60) Provisional application No. 62/453,851, filed on Feb. 2, 2017, provisional application No. 62/447,048, filed on Jan. 17, 2017.

(51) Int. Cl.
| | |
|---|---|
| *A61K 47/58* | (2017.01) |
| *A61K 38/28* | (2006.01) |
| *A61K 47/54* | (2017.01) |
| *A61K 47/69* | (2017.01) |
| *A61P 3/10* | (2006.01) |

(52) U.S. Cl.
CPC ............ *A61K 47/58* (2017.08); *A61K 38/28* (2013.01); *A61K 47/549* (2017.08); *A61K 47/6903* (2017.08); *A61P 3/10* (2018.01)

(58) Field of Classification Search
None
See application file for complete search history.

(56) References Cited

U.S. PATENT DOCUMENTS

| | | |
|---|---|---|
| 2011/0097277 A1 | 4/2011 | Jiang et al. |
| 2011/0301083 A1 | 12/2011 | Zion et al. |
| 2011/0319569 A1 | 12/2011 | Emrick et al. |
| 2012/0315239 A1* | 12/2012 | Jiang ............ A61K 38/4826 424/78.17 |
| 2013/0172243 A1 | 7/2013 | Fineman et al. |
| 2014/0221577 A1 | 8/2014 | Jiang et al. |
| 2015/0246138 A1 | 9/2015 | Linder et al. |

FOREIGN PATENT DOCUMENTS

| | | |
|---|---|---|
| WO | 2015/051052 A2 | 4/2015 |
| WO | 2016/138528 A1 | 9/2016 |

OTHER PUBLICATIONS

Miyata et al. (J Biomater Sci Polym Ed. 2004; 15(9):1085-9) (Year: 2004).*
Miyata, T. et al., Preparation of reversibly glucose-responsive hydrogels by covalent immobilization of lectin in polymer networks having pendant glucose, Journal of Biomaterials Sci. Polymer Edn., 15(9): 1085-1098, 2004.
Keefe, A. et al., Poly(zwitterionic)protein conjugates offer increased stability without sacrificing binding affinity or bioactivity, Nature Chemistry, 4(1):59-63, Dec. 11, 2011.
Bhattacharjee, S. et al., Site-specific zwitterionic polymer conjugates of a protein have long plasma circulation, Chembiochem., 16(17):2451-2455, Oct. 20, 2015.

* cited by examiner

*Primary Examiner* — Sergio Coffa
(74) *Attorney, Agent, or Firm* — Julie K. Staple; Dinsmore & Shohl LLP

(57) ABSTRACT

Glucose-responsive zwitterionic polymer-insulin-saccharide compositions are provided according to aspects of the present disclosure which include a zwitterionic polymer, an insulin moiety, a saccharide moiety, and a saccharide binding molecule. Methods of use of glucose-responsive zwitterionic polymer-insulin-saccharide compositions according to aspects of the present disclosure include administration to human patients to alleviate conditions, such as diabetes, which are responsive to administration of insulin.

2 Claims, 16 Drawing Sheets

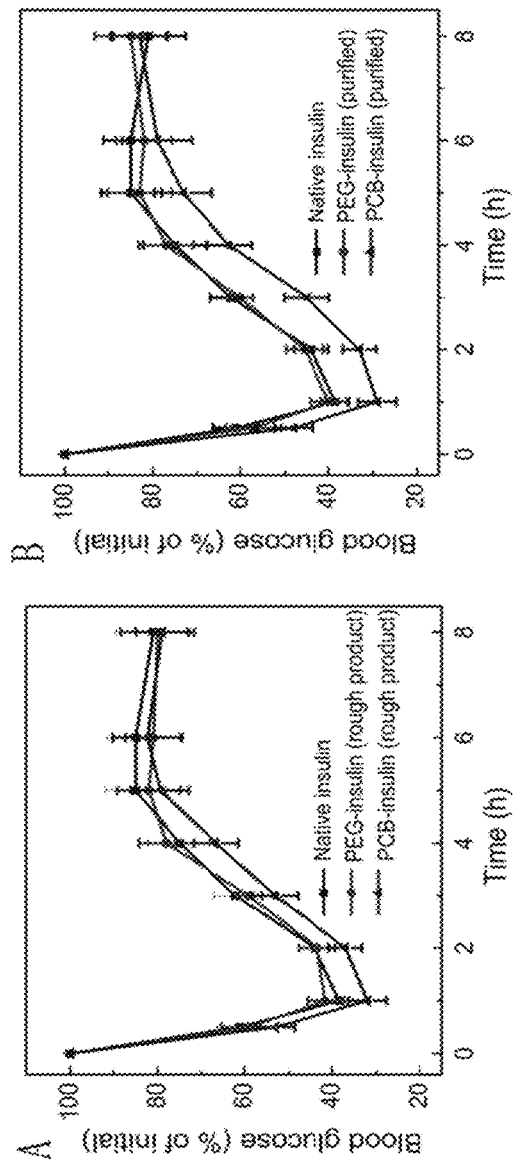
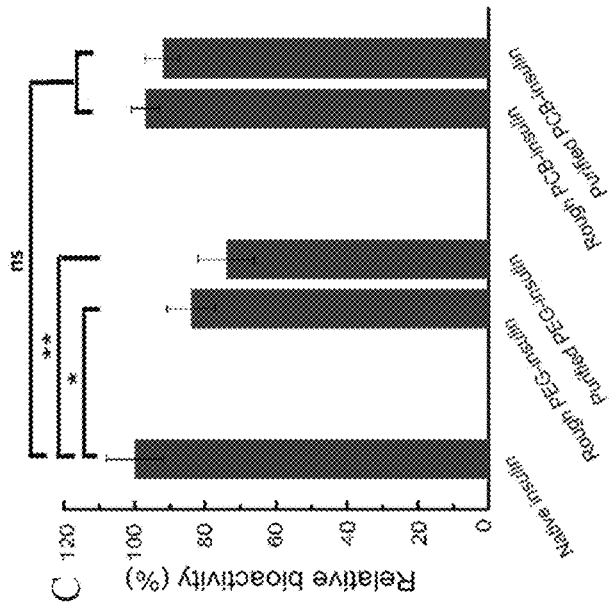
FIG. 4A
FIG. 4B
FIG. 4C

ZWITTERIONIC POLYMER-INSULIN COMPOSITIONS AND RELATED METHODS

REFERENCE TO RELATED APPLICATIONS

This application is a divisional of U.S. patent application Ser. No. 16/478,352, filed Jul. 16, 2019, which is a U.S. national stage application of PCT/US2018/014038, filed Jan. 17, 2018, which claims priority to U.S. Provisional Patent Application Ser. Nos. 62/447,048, filed Jan. 17, 2017, and 62/453,851, filed Feb. 2, 2017, the entire content of all of which is incorporated herein by reference.

FIELD OF THE INVENTION

The present invention relates generally to compositions including insulin, their methods of synthesis and use. In specific aspects the disclosure relates to compositions including zwitterionic compositions including insulin, their methods of synthesis and use.

BACKGROUND OF THE INVENTION

There is a continuing need for compositions including insulin for treatment of diabetes and other disorders for which exogenously administered insulin is beneficial.

SUMMARY OF THE INVENTION

Zwitterionic polymer-insulin-saccharide compositions are provided by the present disclosure which include a zwitterionic polymer, an insulin moiety, and a saccharide moiety.

Zwitterionic polymer-insulin-saccharide compositions are provided by the present disclosure which include a zwitterionic polymer, an insulin moiety, a saccharide moiety, and a pharmaceutically acceptable carrier.

Zwitterionic polymer-insulin-saccharide compositions are provided by the present disclosure which include a polymerization reaction product of a zwitterionic monomer, an insulin-containing monomer, and a saccharide-containing monomer.

One of skill in the art will recognize that a polymerization reaction product of specific monomers includes repeating units derived from the monomers. A polymerization reaction product of a zwitterionic monomer, an insulin-containing monomer, and a saccharide-containing monomer includes zwitterionic repeating units, insulin-containing repeating units and saccharide-containing repeating units.

According to aspects described herein, the zwitterionic monomer has the structural formula:

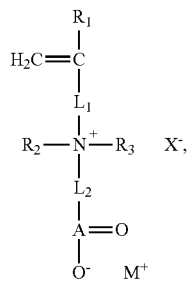

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; $X^-$ is a counter ion associated with the cationic center; and $M^+$ is a metal cation, an ammonium cation, or an organic cation.

According to aspects described herein, the zwitterionic monomer is selected from the group consisting of: carboxybetaine acrylamide; carboxybetaine methacrylate; carboxybetaine methacrylamide; carboxybetaine acrylate; carboxybetaine vinyl; sulfobetaine acrylamide; sulfobetaine methacrylate; sulfobetaine methacrylamide; sulfobetaine acrylate; sulfobetaine vinyl; phosphobetaine acrylamide; phosphobetaine methacrylate; phosphobetaine methacrylamide; phosphobetaine acrylate; phosphobetaine vinyl; and two or more thereof Zwitterionic polymer-insulin-saccharide compositions are provided by the present disclosure which include a polymerization reaction product of a zwitterionic monomer, an insulin-containing monomer, and a saccharide-containing monomer, wherein the insulin monomer comprises a terminal acryloyl functional group, the zwitterionic monomer comprises a terminal acryloyl functional group, and the saccharide monomer comprises a terminal acryloyl functional group.

Zwitterionic polymer-insulin-saccharide compositions are provided by the present disclosure which include a polymerization reaction product of a zwitterionic monomer, an insulin-containing monomer, and a saccharide-containing monomer, wherein the saccharide moiety or saccharide monomer comprises a saccharide selected from the group consisting of: mannose, fucose, a bisaccharide, a trisaccharide, a tetrasaccharide, a branched trisaccharide, bimannose, trimannose, tetramannose, branched trimannose, glucosamine, a derivative of any thereof, and a combination of any two or more thereof.

Zwitterionic polymer-insulin-saccharide compositions are provided by the present disclosure which include a polymerization reaction product of a zwitterionic monomer, an insulin-containing monomer, and a saccharide-containing monomer, wherein the saccharide monomer comprises mannose.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition and wherein the saccharide binding molecule is a lectin, a saccharide binding fragment thereof or a combination of any two or more thereof.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition and wherein the saccharide binding molecule is mannose selective or fucose selective.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition and wherein the saccharide binding molecule is selected from the group consisting of: human mannose binding protein (MBP), human mannose receptors, human pulmonary surfactant protein A (SP-1), human pulmonary surfactant protein D, collectin-43, conglutinin, a phytohemagglutinin, human fucose binding protein, human fucose receptor, and exogenous lectins including but not limited to includes *Lotus tetragonolobus* lectin, *Ulex europaeus* agglutinin, *Lens culimaris* agglutinin, *Aleuria aurantia* lectin, *Anguilla* lectin, *Rhizopus stolonifera* lectin, *Ralstonia solanacearum* lectin, a saccharide binding fragment of any thereof, and a combination of any two or more thereof.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition and wherein the saccharide binding molecule is selected from the group consisting of: concanavalin A, a phytohemoagglutinin derived from *Galanthus nivalis* (snowdrop), *Pisum sativum* (pea), *lathyrus odoratus* (sweet pea), *lens culinaris* (lentil), *narcissus pseudonarcissus* (daffodil), *Vicia faba* (fava bean), and *vicia sativa* (garden vetch), a saccharide binding fragment of any thereof, and a combination of any two or more thereof.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition and wherein the saccharide binding molecule includes two or more binding fragments of lectins covalently linked to each other.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition and wherein the saccharide binding molecule is a human saccharide binding molecule or a non-human saccharide binding molecule.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule is Concavalin A and the saccharide is mannose.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition and wherein the ratio of the saccharide binding molecule to the zwitterionic polymer-insulin-saccharide composition is in the range of 0.001:1-1:0.001.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition and wherein the saccharide binding molecule is covalently bonded to a second polymer or a hydrogel wherein the second polymer comprises a zwitterionic polymer or zwitterionic repeating unit and/or the hydrogel comprises a zwitterionic polymer or zwitterionic repeating unit.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition, and wherein the compositions are in the form of a gel. Optionally, the gel is in the form of particles having a particle diameter or longest dimension in the range of 1 nm to 50 cm, such as 1 nm to 1 mm, 1 mm to 1 cm or 1 cm to 50 cm.

Glucose-responsive zwitterionic polymer-insulin-saccharide compositions are provided by the present disclosure which include in combination: a saccharide binding molecule; and a zwitterionic polymer-insulin-saccharide composition of the present disclosure, wherein the saccharide binding molecule binds to the saccharide of the zwitterionic polymer-insulin-saccharide composition and further including a hydrogel carrier, where the glucose-responsive zwitterionic polymer-insulin-saccharide composition is encapsulated by the hydrogel carrier, producing a hydrogel encapsulated glucose-responsive zwitterionic polymer-insulin-saccharide composition. According to particular aspects of the present disclosure, the hydrogel carrier is or includes a zwitterionic polymer and/or includes a zwitterionic repeating unit.

Optionally, a glucose-responsive zwitterionic polymer-insulin-saccharide composition includes a pharmaceutically acceptable carrier.

Zwitterionic polymer-insulin compositions are provided according to aspects of the present disclosure.

Zwitterionic polymer-insulin compositions are provided according to aspects of the present disclosure which include a reaction product selected from the group consisting of: a (poly)carboxybetaine polymer comprising reactive groups that react with primary amines, and insulin; a (poly)sulfobetaine polymer comprising reactive groups that react with primary amines, and insulin; and a (poly)phosphobetaine polymer comprising reactive groups that react with primary amines, and insulin. According to aspects of the disclosure, the (poly)carboxybetaine polymer comprising reactive groups that react with primary amines is selected from the group consisting of: (poly)carboxybetaine acrylamide comprising reactive groups that react with primary amines; (poly)carboxybetaine methacrylate comprising reactive groups that react with primary amines; (poly)carboxybetaine methacrylamide comprising reactive groups that react with primary amines; (poly)carboxybetaine acrylate comprising reactive groups that react with primary amines; (poly)carboxybetaine vinyl comprising reactive groups that react with primary amines; (poly)sulfobetaine acrylamide comprising reactive groups that react with primary amines;

(poly)sulfobetaine methacrylate comprising reactive groups that react with primary amines; (poly)sulfobetaine methacrylamide comprising reactive groups that react with primary amines; (poly)sulfobetaine acrylate comprising reactive groups that react with primary amines; (poly) sulfobetaine vinyl comprising reactive groups that react with primary amines; (poly)phosphobetaine acrylamide comprising reactive groups that react with primary amines; (poly) phosphobetaine methacrylate comprising reactive groups that react with primary amines; (poly)phosphobetaine methacrylamide comprising reactive groups that react with primary amines; (poly)phosphobetaine acrylate comprising reactive groups that react with primary amines; (poly) phosphobetaine vinyl comprising reactive groups that react with primary amines; and any two or more thereof. According to particular aspects of the present disclosure, the reactive groups that react with primary amines are selected from the group consisting of: isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters.

Zwitterionic polymer-insulin compositions are provided according to aspects of the present disclosure which include a reaction product of an NHS ester terminated (poly)carboxybetaine polymer and insulin.

Zwitterionic polymer-insulin compositions are provided according to aspects of the present disclosure which include a reaction product of insulin and an NHS ester terminated (poly)carboxybetaine polymer selected from the group consisting of: NHS ester terminated (poly)carboxybetaine acrylamide; NHS ester terminated (poly)carboxybetaine methacrylate; NHS ester terminated (poly)carboxybetaine methacrylamide; NHS ester terminated (poly)carboxybetaine acrylate; NHS ester terminated (poly)carboxybetaine vinyl; NHS ester terminated (poly)sulfobetaine acrylamide; NHS ester terminated (poly)sulfobetaine methacrylate; NHS ester terminated (poly)sulfobetaine methacrylamide; NHS ester terminated (poly)sulfobetaine acrylate; NHS ester terminated (poly)sulfobetaine vinyl; NHS ester terminated (poly)phosphobetaine acrylamide; NHS ester terminated (poly)phosphobetaine methacrylate; NHS ester terminated (poly)phosphobetaine methacrylamide; NHS ester terminated (poly)phosphobetaine acrylate; NHS ester terminated (poly)phosphobetaine vinyl; and two or more thereof.

Zwitterionic polymer-insulin compositions are provided according to aspects of the present disclosure which include a reaction product of: a (poly)carboxybetaine polymer comprising reactive groups that react with primary amines; and insulin.

Zwitterionic polymer-insulin compositions are provided according to aspects of the present disclosure which include a polymerization reaction product of a zwitterionic monomer and an insulin-containing monomer.

Zwitterionic polymer-insulin compositions are provided according to aspects of the present disclosure which include a polymerization reaction product of a zwitterionic monomer and an insulin-containing monomer, wherein the zwitterionic monomer has the structural formula:

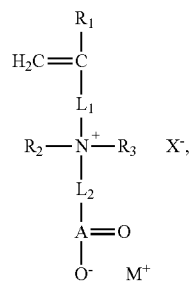

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; $X^-$ is the counter ion associated with the cationic center; and $M^+$ is a metal cation, an ammonium cation, or an organic cation.

Zwitterionic polymer-insulin compositions are provided according to aspects of the present disclosure which include a polymerization reaction product of a zwitterionic monomer and an insulin-containing monomer, wherein the zwitterionic monomer is selected from the group consisting of: carboxybetaine acrylamide; carboxybetaine methacrylate; carboxybetaine methacrylamide; carboxybetaine acrylate; carboxybetaine vinyl; sulfobetaine acrylamide; sulfobetaine methacrylate; sulfobetaine methacrylamide; sulfobetaine acrylate; sulfobetaine vinyl; phosphobetaine acrylamide; phosphobetaine methacrylate; phosphobetaine methacrylamide; phosphobetaine acrylate; phosphobetaine vinyl; and two or more thereof Zwitterionic polymer-insulin compositions are provided according to aspects of the present disclosure which include a polymerization reaction product of a zwitterionic monomer and an insulin-containing monomer, wherein the insulin monomer comprises a terminal acryloyl functional group.

Zwitterionic polymer-insulin compositions are provided according to aspects of the present disclosure which include a polymerization reaction product of a zwitterionic monomer and an insulin-containing monomer, wherein the zwitterionic monomer is selected from the group consisting of: carboxybetaine acrylamide; carboxybetaine methacrylate; carboxybetaine methacrylamide; carboxybetaine acrylate; carboxybetaine vinyl; sulfobetaine acrylamide; sulfobetaine methacrylate; sulfobetaine methacrylamide; sulfobetaine acrylate; sulfobetaine vinyl; phosphobetaine acrylamide; phosphobetaine methacrylate; phosphobetaine methacrylamide; phosphobetaine acrylate; phosphobetaine vinyl; and two or more thereof; and, wherein the insulin monomer comprises a terminal acryloyl functional group.

Hydrogel carriers or barriers for glucose-responsive release of insulin, including a zwitterionic polymer, a saccharide, and a saccharide binding molecule are provided according to aspects of the present disclosure.

Methods of treatment of a subject in need of insulin, wherein the subject has type 1 diabetes, type 2 diabetes, gestational diabetes or pre-diabetes, are provided according to aspects of the present disclosure which include administering a composition selected from the group consisting of: a zwitterionic polymer-insulin composition, a zwitterionic polymer-insulin-saccharide composition, a glucose-responsive zwitterionic polymer-insulin composition, and a combination of any two or more thereof. The subject can be a human subject.

Methods of treatment of a subject in need of insulin are provided according to aspects of the present disclosure which include administering a composition selected from the group consisting of: a zwitterionic polymer-insulin composition, a zwitterionic polymer-insulin-saccharide composition, a glucose-responsive zwitterionic polymer-insulin composition, and a combination of any two or more thereof. The subject can be a human subject.

Medical devices are provided according to aspects of the present disclosure which includes a composition selected from the group consisting of: a zwitterionic polymer-insulin composition, a zwitterionic polymer-insulin-saccharide composition, a glucose-responsive zwitterionic polymer-insulin composition, and a combination of any two or more thereof. Optionally, the included glucose-responsive zwitterionic polymer-insulin-saccharide composition is in gel form.

A conjugate, composition, device and method is provided by the present disclosure wherein the zwitterionic polymer-insulin conjugate or composition included in the conjugate, composition, device or method includes a zwitterionic polymer conjugated to at least one insulin amino acid residue selected from the group consisting of: GlyA1, PheB2 and LysB29.

A conjugate, composition, device and method is provided by the present disclosure wherein the zwitterionic polymer-insulin conjugate is (poly)carboxybetaine polymer-insulin, (poly)sulfobetaine polymer-insulin, or (poly)phosphobetaine polymer-insulin, wherein the (poly)carboxybetaine polymer-insulin, (poly)sulfobetaine polymer-insulin or (poly)phosphobetaine polymer-insulin comprises (poly)carboxybetaine polymer, (poly)sulfobetaine polymer or (poly)phosphobetaine polymer conjugated to LysB29.

A conjugate, composition, device and method is provided by the present disclosure wherein the zwitterionic polymer-insulin conjugate is (poly)carboxybetaine polymer-insulin, (poly)sulfobetaine polymer-insulin or (poly)phosphobetaine polymer-insulin wherein the (poly)carboxybetaine polymer-insulin, (poly)sulfobetaine polymer-insulin or (poly)phosphobetaine polymer-insulin comprises (poly)carboxybetaine polymer, (poly)sulfobetaine polymer or (poly)phosphobetaine polymer conjugated to at least one insulin amino acid residue selected from the group consisting of: GlyA1, PheB2 and LysB29.

A conjugate, composition, device and method is provided by the present disclosure wherein the zwitterionic polymer-insulin conjugate is (poly)carboxybetaine polymer-insulin, (poly)sulfobetaine polymer-insulin or (poly)phosphobetaine polymer-insulin, wherein the (poly)carboxybetaine polymer-insulin, (poly)sulfobetaine polymer-insulin or (poly)phosphobetaine polymer-insulin comprises (poly)carboxybetaine polymer, (poly)sulfobetaine polymer or (poly)phosphobetaine polymer conjugated to LysB29.

A conjugate, composition, device and method is provided by the present disclosure wherein the zwitterionic polymer-insulin conjugate or composition includes a mixture of a zwitterionic polymer-insulin conjugates including zwitterionic polymer conjugated to insulin at LysB29, zwitterionic polymer conjugated to insulin at PheB2 and zwitterionic polymer conjugated to insulin at GlyA1, wherein 50% or more of the zwitterionic polymer-insulin conjugates in the mixture comprise zwitterionic polymer conjugated to insulin at LysB29.

A conjugate, composition, device and method is provided by the present disclosure wherein the zwitterionic polymer-insulin conjugate or composition includes a mixture of a zwitterionic polymer-insulin conjugates including (poly)carboxybetaine polymer conjugated to insulin at LysB29, (poly)carboxybetaine polymer conjugated to insulin at PheB2 and (poly)carboxybetaine polymer conjugated to insulin at GlyA1, wherein 50% or more of the zwitterionic polymer-insulin conjugates in the mixture comprise (poly)carboxybetaine polymer conjugated to insulin at LysB29.

A conjugate, composition, device and method is provided by the present disclosure wherein the zwitterionic polymer-insulin conjugate or composition includes a mixture of a zwitterionic polymer-insulin conjugates including (poly)sulfobetaine polymer conjugated to insulin at LysB29, (poly)sulfobetaine polymer conjugated to insulin at PheB2 and (poly)sulfobetaine polymer conjugated to insulin at GlyA1, wherein 50% or more of the zwitterionic polymer-insulin conjugates in the mixture comprise (poly)sulfobetaine polymer conjugated to insulin at LysB29.

A conjugate, composition, device and method is provided by the present disclosure wherein the zwitterionic polymer-insulin conjugate or composition includes a mixture of a zwitterionic polymer-insulin conjugates including (poly)phosphobetaine polymer conjugated to insulin at LysB29, (poly)phosphobetaine polymer conjugated to insulin at PheB2 and (poly)phosphobetaine polymer conjugated to insulin at GlyA1, wherein 50% or more of the zwitterionic polymer-insulin conjugates in the mixture comprise (poly)phosphobetaine polymer conjugated to insulin at LysB29.

A conjugate, composition, device and method is provided by the present disclosure wherein the zwitterionic polymer-insulin conjugate or composition includes native human insulin conjugated to a zwitterionic polymer.

A conjugate, composition, device and method is provided by the present disclosure wherein the zwitterionic polymer-insulin conjugate or composition includes an insulin analog selected from the group consisting of: insulin glulisine, insulin lispro, insulin aspart, insulin glargine, insulin detemir, insulin isophane, GLP-1, and a GLP-1 agonist, conjugated to a zwitterionic polymer.

BRIEF DESCRIPTION OF THE DRAWINGS

FIG. 4A is a graph comparing blood glucose lowering abilities of non-purified PCB-insulin conjugate, non-purified PEG-insulin conjugate and free (native) insulin;

FIG. 4B is a graph comparing blood glucose lowering abilities of purified PCB-insulin conjugate, purified PEG-insulin conjugate and free (native) insulin;

FIG. 4C is a graph showing the bioactivity of native insulin, rough (non-purified) PEG-insulin, purified PEG-insulin, rough (non-purified) PCB-insulin and purified PCB-insulin, respectively, as measured by phosphorylation of the insulin receptor in vitro.

DETAILED DESCRIPTION OF THE INVENTION

Figure 1:
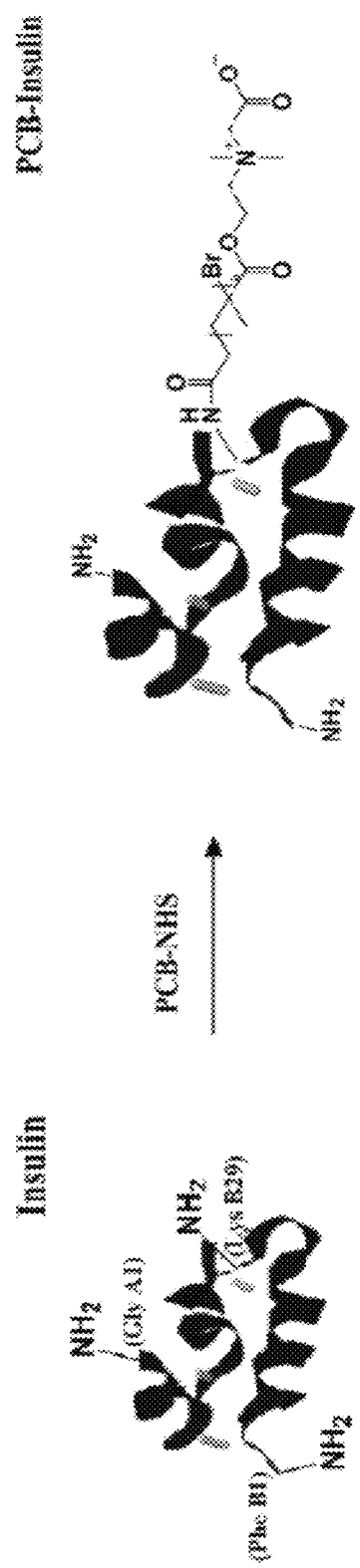
FIG. 1 is a diagram illustrating conjugation of insulin with NHS functionalized zwitterionic carboxybetaine polymer (zwitterionic carboxybetaine polymer is abbreviated PCB herein)

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Engelke, D. R., RNA Interference (RNAi): Nuts and Bolts of RNAi Technology, DNA Press LLC, Eagleville, P A, 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, PA: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

According to aspects of the present disclosure, zwitterionic polymer-insulin compositions which are conjugates or polymerization reaction products.

Zwitterionic polymer-insulin conjugates are provided according to aspects of the present disclosure.

Zwitterionic polymer-insulin conjugates are provided according to aspects of the present disclosure which include a reaction product of: a zwitterionic polymer comprising reactive groups that react with primary amines; and insulin.

The term "insulin" as used herein refers to native insulin and analogs of insulin characterized by one or more functional characteristics of native insulin. Functional characteristics of native insulin are well-known and include both direct and indirect physiological effects, for example, blood glucose lowering activity and phosphorylation of the insulin receptor.

Native insulin is a well-known protein hormone produced in beta cells of pancreatic islets. In mature form, native human insulin consists of two amino acid chains, chain A and chain B, linked by disulfide bonds between CysA7 and CysB7 and between CysA20 and CysB19 and an internal disulfide bridge between CysA6 and CysA11. Chain A is 21 amino acid residues and chain B is 30 amino acid residues. In this native form, human insulin contains three free primary amines, the N-terminal glycine of chain A: GlyA1; the N-terminal phenylalanine of chain B: PheB1; and a lysine at position 29 in chain B: LysB29.

The terminology "A1," "B1", "B29" etc. refers to the amino acid residue in position 1 in the A chain of insulin (counted from the N-terminal end), the amino acid residue in position 1 in the B chain of insulin (counted from the N-terminal end), and the amino acid residue in position 29 in the B chain of insulin (counted from the N-terminal end), respectively. The amino acid residue in a specific position may also be denoted as e.g. GlyA1 which indicates that the amino acid residue in position 1 of the A chain is a glycine residue.

Native insulin from any of various species can be isolated or synthesized, such as by chemical or molecular recombinant techniques, for conjugation with a zwitterionic polymer according to aspects of the present disclosure, including but not limited to, human, porcine, and bovine. Human insulin is conjugated with a zwitterionic polymer according to aspects of the present disclosure.

Analogs of insulin include, but are not limited to, insulin glulisine, insulin lispro, insulin aspart, insulin glargine, insulin detemir, and insulin isophane, any or all of which can be modified according to aspects of the present disclosure to produce a zwitterionic polymer-insulin conjugate by conjugation of a zwitterionic polymer to a primary amine of an insulin analog.

Analogs of insulin characterized by one or more functional characteristics of insulin can be generated by substitution or deletion of one or more amino acid residues of native insulin.

Insulin analogs include those containing an amino acid residue substitution at position B28 wherein the ProB28 is substituted by Asp, Lys or Ile. Insulin analogs include those containing an amino acid residue substitution at position B29 wherein the LysB29 is substituted by Pro. Insulin analogs include those containing an amino acid residue substitution at position B30 wherein the ThrB30 is substituted by Lys and LysB29 is Cys, Met, Arg or Lys. Insulin analogs include those containing an amino acid residue substitution at position A21 wherein the AsnA21 is substituted by Ala, Gln, Glu, Gly, His, Ile, Leu, Met, Ser, Thr, Trp, Tyr or Val. Insulin analogs include those containing an amino acid residue substitution at position B3 wherein the AsnB3 is substituted by Lys or Asp. Insulin analogs include those containing an amino acid residue deletion at position B1 and/or B2 and/or B26-B30. Insulin analogs further include those having an N-terminal or C-terminal extension of the A chain, B chain or both.

Assays of one or more functional characteristics of a putative analog are well known in the art, such as assay of blood glucose lowering activity and/or phosphorylation of the insulin receptor compared to native insulin or an insulin analog.

Zwitterionic polymer-insulin conjugates are provided according to aspects of the present disclosure including a (poly)carboxybetaine polymer (abbreviated PCB herein), (poly)sulfobetaine polymer or (poly)phosphobetaine polymer including reactive groups that react with primary amines selected from the group consisting of: (poly)carboxybetaine acrylamide including reactive groups that react with primary amines; (poly)carboxybetaine methacrylate including reactive groups that react with primary amines; (poly)carboxybetaine methacrylamide including reactive groups that react with primary amines; (poly)carboxybetaine acrylate including reactive groups that react with primary amines; (poly)carboxybetaine vinyl including reactive groups that react with primary amines; (poly)sulfobetaine acrylamide including reactive groups that react with primary amines; (poly)sulfobetaine methacrylate including reactive groups that react with primary amines; (poly)sulfobetaine methacrylamide including reactive groups that react with primary amines; (poly)sulfobetaine acrylate including reactive groups that react with primary amines; (poly)sulfobetaine vinyl including reactive groups that react with primary amines; (poly)phosphobetaine acrylamide including reactive groups that react with primary amines; (poly)phosphobetaine methacrylate including reactive groups that react with primary amines; (poly)phosphobetaine methacrylamide including reactive groups that react with primary amines; (poly)phosphobetaine acrylate including reactive groups that react with primary amines; (poly)phosphobetaine vinyl including reactive groups that react with primary amines; and any two or more thereof.

Reactive groups that react with primary amines include, but are not limited to, isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters.

Zwitterionic polymer-insulin conjugates are provided according to aspects of the present disclosure wherein the conjugate includes a reaction product of an NHS ester terminated (poly)carboxybetaine polymer, (poly)sulfobetaine polymer or (poly)phosphobetaine polymer; and insulin.

Zwitterionic polymer-insulin conjugates are provided according to aspects of the present disclosure wherein the conjugate includes a reaction product of insulin and an NHS ester terminated (poly)carboxybetaine polymer selected from the group consisting of: NHS ester terminated (poly)carboxybetaine acrylamide; NHS ester terminated (poly)carboxybetaine methacrylate; NHS ester terminated (poly)carboxybetaine methacrylamide; NHS ester terminated (poly)carboxybetaine acrylate; NHS ester terminated (poly)carboxybetaine vinyl; NHS ester terminated (poly)sulfobetaine acrylamide; NHS ester terminated (poly)sulfobetaine methacrylate; NHS ester terminated (poly)sulfobetaine methacrylamide; NHS ester terminated (poly)sulfobetaine acrylate; NHS ester terminated (poly)sulfobetaine vinyl; NHS ester terminated (poly)phosphobetaine acrylamide; NHS ester terminated (poly)phosphobetaine methacrylate; NHS ester terminated (poly)phosphobetaine methacrylamide; NHS ester terminated (poly)phosphobetaine acrylate; NHS ester terminated (poly)phosphobetaine vinyl; and any two or more thereof.

Zwitterionic polymer-insulin conjugates are provided according to aspects of the present disclosure wherein the conjugate includes a reaction product of: a (poly)carboxybetaine polymer, a (poly)sulfobetaine polymer including reactive groups that react with primary amines or a (poly)phosphobetaine polymer including reactive groups that react with primary amines; and insulin.

Particular zwitterionic polymer-insulin conjugates provided according to aspects of the present disclosure include a (poly)carboxybetaine-insulin, (poly)sulfobetaine-insulin or (poly)phosphobetaine-insulin conjugate wherein the conjugate is a reaction product of the free amine GlyA1 of insulin and an NHS ester terminated (poly)carboxybetaine polymer, NHS ester terminated (poly)sulfobetaine polymer or NHS ester terminated (poly)phosphobetaine polymer.

Particular zwitterionic polymer-insulin conjugates provided according to aspects of the present disclosure include a (poly)carboxybetaine-insulin, (poly)sulfobetaine-insulin or (poly)phosphobetaine-insulin conjugate wherein the conjugate is a reaction product of the free amine PheB1 of insulin and an NHS ester terminated (poly)carboxybetaine polymer, NHS ester terminated (poly)sulfobetaine polymer or NHS ester terminated (poly)phosphobetaine polymer.

Particular zwitterionic polymer-insulin conjugates provided according to aspects of the present disclosure include a (poly)carboxybetaine-insulin, (poly)sulfobetaine-insulin or (poly)phosphobetaine-insulin conjugate wherein the conjugate is a reaction product of the free amine LysB29 of insulin and an NHS ester terminated (poly)carboxybetaine polymer, NHS ester terminated (poly)sulfobetaine polymer or NHS ester terminated (poly)phosphobetaine polymer.

Particular zwitterionic polymer-insulin conjugates provided according to aspects of the present disclosure include a (poly)carboxybetaine-insulin, (poly)sulfobetaine-insulin or (poly)phosphobetaine-insulin conjugate wherein the conjugate is a reaction product of the free amine GlyA1 of insulin and an NHS ester terminated (poly)carboxybetaine polymer, NHS ester terminated (poly)sulfobetaine polymer or NHS ester terminated (poly)phosphobetaine polymer; and the free amine PheB1 of insulin and an NHS ester terminated (poly)carboxybetaine polymer, NHS ester terminated (poly)sulfobetaine polymer or NHS ester terminated (poly)phosphobetaine polymer. Particular zwitterionic polymer-insulin conjugates provided according to aspects of the present disclosure include a (poly)carboxybetaine-insulin, (poly)sulfobetaine-insulin or (poly)phosphobetaine-insulin conjugate wherein the conjugate is a reaction product of the free amine GlyA1 of insulin and an NHS ester terminated (poly)carboxybetaine polymer, NHS ester terminated (poly)sulfobetaine polymer or NHS ester terminated (poly)phosphobetaine polymer; and the free amine LysB29 of insulin and an NHS ester terminated (poly)carboxybetaine polymer, NHS ester terminated (poly)sulfobetaine polymer or NHS ester terminated (poly)phosphobetaine polymer.

Particular zwitterionic polymer-insulin conjugates provided according to aspects of the present disclosure include a (poly)carboxybetaine-insulin, (poly)sulfobetaine-insulin or (poly)phosphobetaine-insulin conjugate wherein the conjugate is a reaction product of the free amine PheB1 of insulin and an NHS ester terminated (poly)carboxybetaine polymer, NHS ester terminated (poly)sulfobetaine polymer or NHS ester terminated (poly)phosphobetaine polymer; and the free amine LysB29 of insulin and an NHS ester terminated (poly)carboxybetaine polymer, NHS ester terminated (poly)sulfobetaine polymer or NHS ester terminated (poly)phosphobetaine polymer.

Particular zwitterionic polymer-insulin conjugates provided according to aspects of the present disclosure include a (poly)carboxybetaine-insulin, (poly)sulfobetaine-insulin or (poly)phosphobetaine-insulin conjugate wherein the conjugate is a reaction product of the free amine GlyA1 of insulin and an NHS ester terminated (poly)carboxybetaine polymer, NHS ester terminated (poly)sulfobetaine polymer or NHS ester terminated (poly)phosphobetaine polymer; the free amine PheB1 of insulin and an NHS ester terminated (poly)carboxybetaine polymer, NHS ester terminated (poly)sulfobetaine polymer or NHS ester terminated (poly)phosphobetaine polymer; and the free amine LysB29 of insulin and an NHS ester terminated (poly)carboxybetaine polymer, NHS ester terminated (poly)sulfobetaine polymer or NHS ester terminated (poly)phosphobetaine polymer.

Particular zwitterionic polymer-insulin conjugates provided according to aspects of the present disclosure include a (poly)carboxybetaine-insulin, (poly)sulfobetaine-insulin or (poly)phosphobetaine-insulin conjugate wherein the conjugate is a reaction product of a free amine of any of insulin glulisine, insulin lispro, insulin aspart, insulin glargine, insulin detemir, and insulin isophane and an NHS ester terminated (poly)carboxybetaine polymer, NHS ester terminated (poly)sulfobetaine polymer or NHS ester terminated (poly)phosphobetaine polymer.

Zwitterionic polymer conjugation to B29 of insulin does not reduce insulin's bioactivity. Zwitterionic polymer-insulin conjugation product synthesized through simple conjugation chemistry as described herein results zwitterionic polymer-insulin conjugation products, the majority of which are conjugates of the zwitterionic polymer at B29 of insulin. The reaction product does not need to be purified and shows no insulin activity loss compared to unconjugated (free) insulin, improved PK and pharmacological activity.

Zwitterionic polymer-insulin compositions are provided according to aspects of the present disclosure which include a polymerization reaction product of a zwitterionic monomer and an insulin-containing monomer.

Zwitterionic polymer-insulin compositions are provided according to aspects of the present disclosure which include a polymerization reaction product of a zwitterionic monomer and an insulin-containing monomer wherein the zwitterionic monomer has the structural formula:

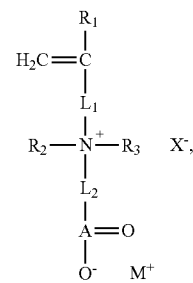

where $R_1$, $R_2$, and $R_3$ are each independently selected from hydrogen, alkyl, and aryl groups; $L_1$ is a linker that covalently couples the cationic center to the polymer backbone; $L_2$ is a linker that covalently couples the cationic center to the anionic group; $A(=O)O^-$ is the anionic group; $X^-$ is the counter ion associated with the cationic center; and $M^+$ is a metal ion, an ammonium ion, or an organic ion.

Zwitterionic polymer-insulin compositions are provided according to aspects of the present disclosure which include a polymerization reaction product of a zwitterionic monomer and an insulin-containing monomer wherein the zwitterionic monomer has the structural formula:

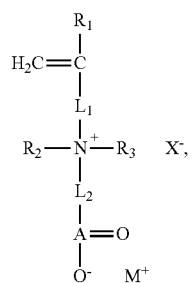

where $R_1$, $R_2$, and $R_3$ are each independently selected from hydrogen, alkyl, and aryl groups; $L_1$ is a linker that covalently couples the cationic center to the polymer backbone; $L_2$ is a linker that covalently couples the cationic center to the anionic group; $A(=O)O^-$ is the anionic group; $X^-$ is the counter ion associated with the cationic center; and $M^+$ is a metal ion, an ammonium ion, or an organic ion, and the insulin monomer comprises a terminal acroyl functional group.

For each $R_1$, $R_2$, and $R_3$ in structural formulas shown herein representative alkyl groups include $C_1$-$C_{30}$ straight chain and branched alkyl groups. According to aspects of the present disclosure, the alkyl group is further substituted with one of more substituents including, for example, an aryl group (e.g., —$CH_2C_6H_5$, benzyl).

For each $R_1$, $R_2$, and $R_3$ in structural formulas shown herein representative aryl groups include $C_6$-$C_{12}$ aryl groups including, for example, phenyl including substituted phenyl groups (e.g., benzoic add).

For each $R_1$, $R_2$, and $R_3$ in structural formulas shown herein representative alkyl groups include O—$C_{10}$ straight chain and branched alkyl groups.

According to aspects of the present disclosure, the alkyl group is further substituted with one of more substituents including, for example, an aryl group (e.g., —$CH_2C_5H_6$, benzyl).

According to aspects of the present disclosure, $R_2$ and $R_3$ in structural formulas shown herein are methyl.

According to aspects of the present disclosure, $R_2$, and in structural formulas shown herein are methyl.

According to aspects of the present disclosure, $R_2$ and $R_3$ are taken together with $N^+$ form the cationic center in structural formulas shown herein.

According to aspects of the present disclosure, $L_1$ includes a functional group (e.g., ester or amide) that couples the remainder of $L_1$ to the C=C double bond for the monomers, or the backbone for the polymers. In addition to the functional group, $L_1$ can include a $C_1$-$C_{20}$ alkylene chain. Representative $L_1$ groups include —C(=O)O—$(CH_2)_n$— and —C(=O)NH—$(CH_2)_n$—, where n is 1-20 (e.g., n=2).

$L_1$ can be a $C_1$-$C_{20}$ alkylene chain according to aspects of the present disclosure. Representative $L_2$ groups include —$(CH_2)_n$—, where n is 1-20 (e.g., 1, 2, or 3).

$A(=O)O^-$ is an anionic group in structural formulas shown herein. The group is a carboxylic acid (where A is C), a sulfmic acid (where A is S), a sulfonic acid (where A is SO), a phosphinic acid (where A is P), or a phosphonic acid (where A is PO).

As noted, X in structural formula shown herein is the counter ion associated with the cationic center. The counter ion can be the counter ion that results from the synthesis of the cationic polymers or the monomers (e.g., $Cl^-$, $Br^-$, $I^-$). The counter ion that is initially produced from the synthesis of the cationic center can also be exchanged with other suitable counter ions to provide polymers having controllable hydrolysis properties and other biological properties. According to aspects of the present disclosure, representative hydrophobic counter ions include carboxylates, such as benzoic acid and fatty acid anions (e.g., $CH_3(CH_2)_nCO)_2^-$ where n can be from 1 to 19); alkyl sulfonates (e.g., $CH_3(CH_2)_nSO_3^-$ where n can be from 1 to 19); salicylate; lactate; bis(trifluoromethylsulfonyl)amide anion ($N^-(SO_2CF_3)2$); and derivatives thereof. Other counter ions also can be chosen from chloride, bromide, iodide, sulfate; nitrate; perchlorate ($ClO_4$); tetrafluoroborate ($BF_4$); hexafluorophosphate ($PF_6$); trifluoromethylsulfonate ($SO_3CF_3$); and derivatives thereof. Other suitable counter ions include salicylic acid (2-hydroxybenzoic acid), benzoate, and lactate.

Zwitterionic polymer-insulin compositions are provided according to aspects of the present disclosure which include a polymerization reaction product of a zwitterionic monomer and an insulin-containing monomer wherein the reaction product is a copolymer.

Zwitterionic polymer-insulin compositions are provided according to aspects of the present disclosure which include a polymerization reaction product of zwitterionic monomers and an insulin-containing monomer, wherein the reaction product is a copolymer having two or more zwitterionic monomers.

Zwitterionic polymer-insulin compositions are provided according to aspects of the present disclosure which include a polymerization reaction product of a zwitterionic monomer and an insulin-containing monomer wherein the zwitterionic monomer is selected from the group consisting of: carboxybetaine acrylamide; carboxybetaine methacrylate; carboxybetaine methacrylamide; and two or more thereof; and the insulin-containing monomer comprises a terminal acryloyl functional group.

Zwitterionic polymer-insulin conjugates are provided according to aspects of the present disclosure which include a reaction product of a zwitterionic polymer and insulin, wherein the zwitterionic polymer is selected from the group consisting of: a sulfobetaine acrylate polymer, a sulfobetaine methacrylate polymer, a sulfobetaine acrylamide polymer, a sulfobetaine methacrylamide polymer, a sulfobetaine vinyl polymer, a carboxybetaine acrylate polymer, a carboxybetaine methacrylate polymer, a carboxybetaine acrylamide polymer, a carboxybetaine methacrylamide polymer, a carboxybetaine vinyl polymer, a phosphobetaine acrylate polymer, a phosphobetaine methacrylate polymer, a phosphobetaine acrylamide polymer, a phosphobetaine methacrylamide polymer, a phosphobetaine vinyl polymer; a polymer comprising of two or more zwitterionic repeating units selected from the group consisting of: a sulfobetaine acrylate, a sulfobetaine methacrylate, a sulfobetaine acrylamide, a sulfobetaine methacrylamide, a sulfobetaine vinyl compound, a carboxybetaine acrylate, a carboxybetaine methacrylate, a carboxybetaine acrylamide, a carboxybetaine methacrylamide, a carboxybetaine vinyl compound, a phosphobetaine acrylate, a phosphobetaine methacrylate, a phosphobetaine acrylamide, a phosphobetaine methacrylamide, a phosphobetaine vinyl compound; and a mixture of any two or more zwitterionic polymers thereof.

A zwitterionic polymer-insulin conjugate, reaction product may contain zwitterionic polymer conjugated to insulin at any of the free amines of insulin or insulin analogs. Optionally, the zwitterionic polymer-insulin conjugate reaction product is not purified to select for a particular conjugate reaction product. Thus, for example, zwitterionic polymer-insulin conjugate compositions according to aspects of the present disclosure include a zwittionionic polymer conjugated to insulin at LysB29 only, GlyA1 and LysB29, PheB11 and LysB29, GlyA1, PheB1 and LysB29, or a mixture of any two or more of these conjugates, wherein the composition or mixture includes more zwittionionic polymer conjugated to insulin at LysB29 than at any other free amine of insulin or an insulin analog. Alternatively, a particular zwitterionic polymer-insulin conjugate can be purified such that a composition according to aspects of the present disclosure includes a purified zwitterionic polymer-insulin conjugate wherein the zwitterionic polymer is conjugated to insulin at LysB29 only, GlyA1 and LysB29, PheB11 and LysB29, GlyA1, PheB1 and LysB29, wherein the composition includes zwittionionic polymer conjugated to insulin at LysB29 more than at any other free amine of insulin or an insulin analog.

A (poly)carboxybetaine polymer-insulin conjugate, (poly)sulfobetaine polymer-insulin conjugate or (poly)phosphobetaine polymer-insulin conjugate reaction product may contain (poly)carboxybetaine, (poly)sulfobetaine or (poly)phosphobetaine conjugated to insulin at any of the free amines of insulin or insulin analogs. Optionally, the (poly)carboxybetaine polymer-insulin conjugate, (poly)sulfobetaine polymer-insulin conjugate or (poly)phosphobetaine polymer-insulin conjugate reaction product is not purified to select for a particular conjugate reaction product. Thus, for example, polymer-insulin conjugate compositions according to aspects of the present disclosure include (poly)carboxybetaine, (poly)sulfobetaine or (poly)phosphobetaine conjugated to insulin at LysB29 only, GlyA1 and PheB1, GlyA1 and LysB29, PheB11 and LysB29, GlyA1, PheB1 and LysB29, or a mixture of any two or more of these conjugates, wherein the composition or mixture includes more zwittionionic polymer conjugated to insulin at LysB29 than at any other free amine of insulin or an insulin analog. Alternatively, a particular (poly)carboxybetaine, (poly)sulfobetaine or (poly)phosphobetaine polymer-insulin conjugate can be purified such that a composition according to aspects of the present disclosure includes a purified (poly)carboxybetaine, (poly)sulfobetaine or (poly)phosphobetaine polymer-insulin conjugate wherein the (poly)carboxybetaine, (poly)sulfobetaine or (poly)phosphobetaine polymer is conjugated to insulin at LysB29 only, GlyA1 and LysB29, PheB11 and LysB29, GlyA1, PheB1 and LysB29, wherein the composition includes more zwittionionic polymer conjugated to insulin at LysB29 than at any other free amine of insulin or an insulin analog.

Glucose-Responsive Zwitterionic Polymer-Insulin-Saccharide Composition

A glucose-responsive zwitterionic polymer-insulin-saccharide composition, comprising, in combination: 1) a saccharide binding molecule (also called Component B or Composition B herein); and 2) a molecule containing a polymer including a zwitterionic polymer, an insulin moiety, and a saccharide moiety (also called zwitterionic polymer-insulin-saccharide composition, Component A and Composition A herein), wherein the saccharide binding molecule binds to the saccharide of the Component A in the zwitterionic polymer-insulin-saccharide composition.

A glucose-responsive zwitterionic polymer-insulin-saccharide composition, comprising, in certain embodiments, in combination: 1) a saccharide binding molecule (also called Component B or Composition B herein); and 2) a polymerization reaction product of a zwitterionic monomer, an insulin-containing monomer, and a saccharide-containing monomer (also called zwitterionic polymer-insulin-saccharide composition, Component A and Composition A herein), wherein the saccharide binding molecule binds to the saccharide of the saccharide-containing monomer in the zwitterionic polymer-insulin-saccharide composition.

Zwitterionic Polymer-Insulin-Saccharide Composition (Component A)

Provided according to aspects of the present disclosure is a zwitterionic polymer-insulin-saccharide composition (Component A) which is a polymerization reaction product of a zwitterionic monomer, an insulin-containing monomer and a saccharide-containing monomer.

A polymerization reaction mixture for producing a zwitterionic polymer-insulin-saccharide composition includes a zwitterionic monomer, an insulin-containing monomer, a saccharide-containing monomer, and an initiator. The polymerization reaction mixture is dissolved in an aqueous solvent and forms a polymer under conditions that initiates the polymerization of the polymerization reaction mixture.

In one embodiment, the polymerization reaction of the zwitterionic monomer, insulin-containing monomer and saccharide-containing monomer is random free radical copolymerization of the zwitterionic monomer, the insulin-containing monomer and the saccharide-containing monomer. This method allows the synthesis of controlled molecular weight polymers, and allows the zwitterionic polymer-insulin-saccharide composition to be finely tuned such as by altering relative amounts of the zwitterionic monomer, insulin-containing monomer, and saccharide-containing monomer included in the polymerization reaction mixture and in certain embodiments, does not involve any catalysts.

The resulting Component A zwitterionic polymer-insulin-saccharide composition is optionally purified, such as by dialysis, and further optionally freeze-dried for further use. The Component A zwitterionic polymer-insulin-saccharide composition can be characterized to determine its MW using MALDI-TOFF MS, and its composition using NMR.

The amount of the zwitterionic monomer in the polymerization reaction mixture for producing a zwitterionic polymer-insulin-saccharide composition is in the range of 0.1-95% by weight of the polymerization reaction mixture for producing the zwitterionic polymer-insulin-saccharide composition. In certain embodiments, the amount of the zwitterionic monomer in the polymerization reaction mixture is in the range of 0.1-80% by weight of the polymerization reaction mixture for producing the zwitterionic polymer-insulin-saccharide composition. In certain embodiments, the amount of the zwitterionic monomer in the polymerization reaction mixture is in the range of 0.1-70% by weight of the polymerization reaction mixture for producing the zwitterionic polymer-insulin-saccharide composition. In certain embodiments, the amount of the zwitterionic monomer in the polymerization reaction mixture is in the range of 0.1-60% by weight of the polymerization reaction mixture for producing the zwitterionic polymer-insulin-saccharide composition. In certain embodiments, the amount of the zwitterionic monomer in the polymerization reaction mixture is in the range of 0.1-50% by weight of the polymerization reaction mixture for producing the zwitterionic polymer-insulin-saccharide composition.

The concentration of the zwitterionic monomer of the polymerization reaction mixture for producing a zwitterionic polymer-insulin-saccharide composition is in the range of 0.01-2000 mg/ml in the aqueous solvent. In certain embodiments, this concentration is in the range of 0.01-1000 mg/ml. In certain embodiments this concentration is in the range of 0.01-800 mg/ml. In certain embodiments, this concentration is in the range of 0.01-600 mg/ml. In certain embodiments, this concentration is in the range of 0.01-400 mg/ml. In certain embodiments, this concentration is in the range of 0.01-200 mg/ml.

The amount of the insulin-containing monomer in the polymerization reaction mixture for producing a zwitterionic polymer-insulin-saccharide composition is in the range of 0.1-90% by weight of the polymerization reaction mixture for producing the zwitterionic polymer-insulin-saccharide composition. In certain embodiments, the amount of the insulin-containing monomer in the polymerization reaction mixture is in the range of 0.1-50% by weight of the polymerization reaction mixture for producing the zwitterionic polymer-insulin-saccharide composition. In certain embodiments, the amount of the insulin-containing monomer in the polymerization reaction mixture is in the range of 0.1-40% by weight of the polymerization reaction mixture for producing the zwitterionic polymer-insulin-saccharide composition. In certain embodiment, the amount of the insulin-containing monomer in the polymerization reaction mixture is in the range of 0.1-30% by weight of the polymerization reaction mixture for producing the zwitterionic polymer-insulin-saccharide composition. In certain embodiments, the amount of the insulin-containing monomer in the polymerization reaction mixture is in the range of 0.1-20% by weight of the polymerization reaction mixture for producing the zwitterionic polymer-insulin-saccharide composition.

The amount of the saccharide-containing monomer in the polymerization reaction mixture for producing a zwitterionic polymer-insulin-saccharide composition is in the range of 0.1-90% by weight of the polymerization reaction mixture for producing the zwitterionic polymer-insulin-saccharide composition. In certain embodiments, the amount of the saccharide-containing monomer in the polymerization reaction mixture is in the range of 0.1-50% by weight of the polymerization reaction mixture for producing the zwitterionic polymer-insulin-saccharide composition. In certain embodiments, the amount of the saccharide-containing monomer in the polymerization reaction mixture is in the range of 0.1-40% by weight of the polymerization reaction mixture for producing the zwitterionic polymer-insulin-saccharide composition. In certain embodiments, the amount of the saccharide-containing monomer in the polymerization reaction mixture is in the range of 0.1-30% by weight of the polymerization reaction mixture for producing the zwitterionic polymer-insulin-saccharide composition.

The amount of the initiator in the polymerization reaction mixture for producing a zwitterionic polymer-insulin-saccharide composition is in the range of 0.001-10% by weight of the polymerization reaction mixture for producing the zwitterionic polymer-insulin-saccharide composition. In certain embodiments, the amount of the initiator in the polymerization reaction mixture for producing a zwitterionic polymer-insulin-saccharide composition is in the range of 0.001-5% by weight of the polymerization reaction mixture for producing the zwitterionic polymer-insulin-saccharide composition. In certain embodiments, the amount of the initiator in the polymerization reaction mixture for producing a zwitterionic polymer-insulin-saccharide composition is in the range of 0.001-1% by weight of the polymerization reaction mixture for producing the zwitterionic polymer-insulin-saccharide composition.

Zwitterionic polymer-insulin compositions are provided according to aspects of the present disclosure which include a polymerization reaction product of a zwitterionic monomer, an insulin-containing monomer and a mannose-containing monomer.

Zwitterionic polymer-insulin compositions are provided according to aspects of the present disclosure which include a polymerization reaction product of a zwitterionic monomer and an insulin-containing monomer wherein the zwitterionic monomer is selected from the group consisting of: carboxybetaine acrylamide; carboxybetaine methacrylate; carboxybetaine methacrylamide; and two or more thereof, wherein the insulin-containing monomer includes a terminal acryloyl functional group and wherein the mannose containing monomer includes a terminal acryloyl functional group.

Zwitterionic Monomer

Zwitterionic monomers described herein above are useful in synthesis of Component A.

Insulin-Containing Monomer

An insulin-containing monomer used in synthesis of Component A is an insulin moiety containing one or more reactive functional groups suitable for polymerization. Such reactive functional groups include, but are not limited to, a double bond which can be polymerized, such as an acryloyl functional group.

In one embodiment, the insulin-containing monomer is obtained by reacting insulin molecules with acrylic acid derived N-hydroxysuccinimide ester molecules in aqueous conditions. In this reaction, the molar ratio of the insulin:acrylic acid derivative is in the range of 1:0.1-0.01:1. In certain embodiments, the molar ratio of the insulin:acrylic acid derivative in this reaction is in the range of 1:1-1:10. In certain embodiments, the molar ratio of the insulin:acrylic acid derivative in this reaction is in the range of 1:1-1:5. The resulting insulin-containing monomer is purified to remove unreacted materials by ultrafiltration or dialysis, and concentrated to the desired concentration for polymerization or freeze-dried to obtain a powder for future use.

An insulin-containing monomer produced according to this synthetic method includes a mixture of insulin-containing monomers having one, two or three reactive functional groups wherein at least one of the reactive functional groups is conjugated to one of: LysB29, PheB2, or GlyA1 of insulin, at least two of the reactive functional groups is conjugated to two of: LysB29, PheB2, or GlyA1 of insulin, or the three reactive functional groups are conjugated to LysB29, PheB2, and GlyA1 of insulin, respectively.

In certain embodiments, the insulin-containing monomer produced according to this synthetic method includes a mixture of insulin-containing monomers wherein 50% or more of the monomers in the mixture have one reactive functional group conjugated to LysB29 of insulin.

Saccharide-Containing Monomer

A saccharide-containing monomer used in synthesis of Component A is produced by covalently linking one or multiple reactive functional groups to a saccharide. Such reactive functional groups include, but are not limited to, a double bond which can be further polymerized, such as an acryloyl functional group.

The saccharide is selected from, but not limited to, mannose, fucose, a bisaccharide, a trisaccharide, a tetrasaccharide, a branched trisaccharide, bimannose, trimannose, tetramannose, branched trimannose, glucosamine, a derivative of any thereof or a combination of any thereof.

In one embodiment, the α-configuration of mannopyranoside is used as the saccharide to form the mannose-containing monomer. This is a preferred configuration for mannose to bind mannose-selective lectins (e.g., Concavalin A, abbreviated herein as ConA). Specifically, one type of mannose-containing monomer is prepared by reacting a mannose derivative, 4-aminophenyl α-D-mannopyranoside ($NH_2$-mannose), with acryloyl chloride in anhydrate organic solvent such as dimethylformamide, and purified by ether precipitation and solvent evaporation. According to this mannose monomer synthesis, $NH_2$ groups but not OH groups of the mannopyranoside react with acryloyl chloride, with resulting mannose moieties maintaining strong binding capability to lectins. The resulting mannose-containing monomer has a benzene group between the mannose group and polymerizable double bond (the first structure of mannose monomer in FIG. 6). In this reaction, the molar ratio of the mannose derivative:acryloyl chloride is in the range of 1:0.1-0.01:1. In certain embodiments, the molar ratio of the mannose derivative:acryloyl chloride is in the range of 1:1-1:10. In certain embodiments, the molar ratio of the mannose derivative:acryloyl chloride is in the range of 1:1-1:5.

Figure 6:
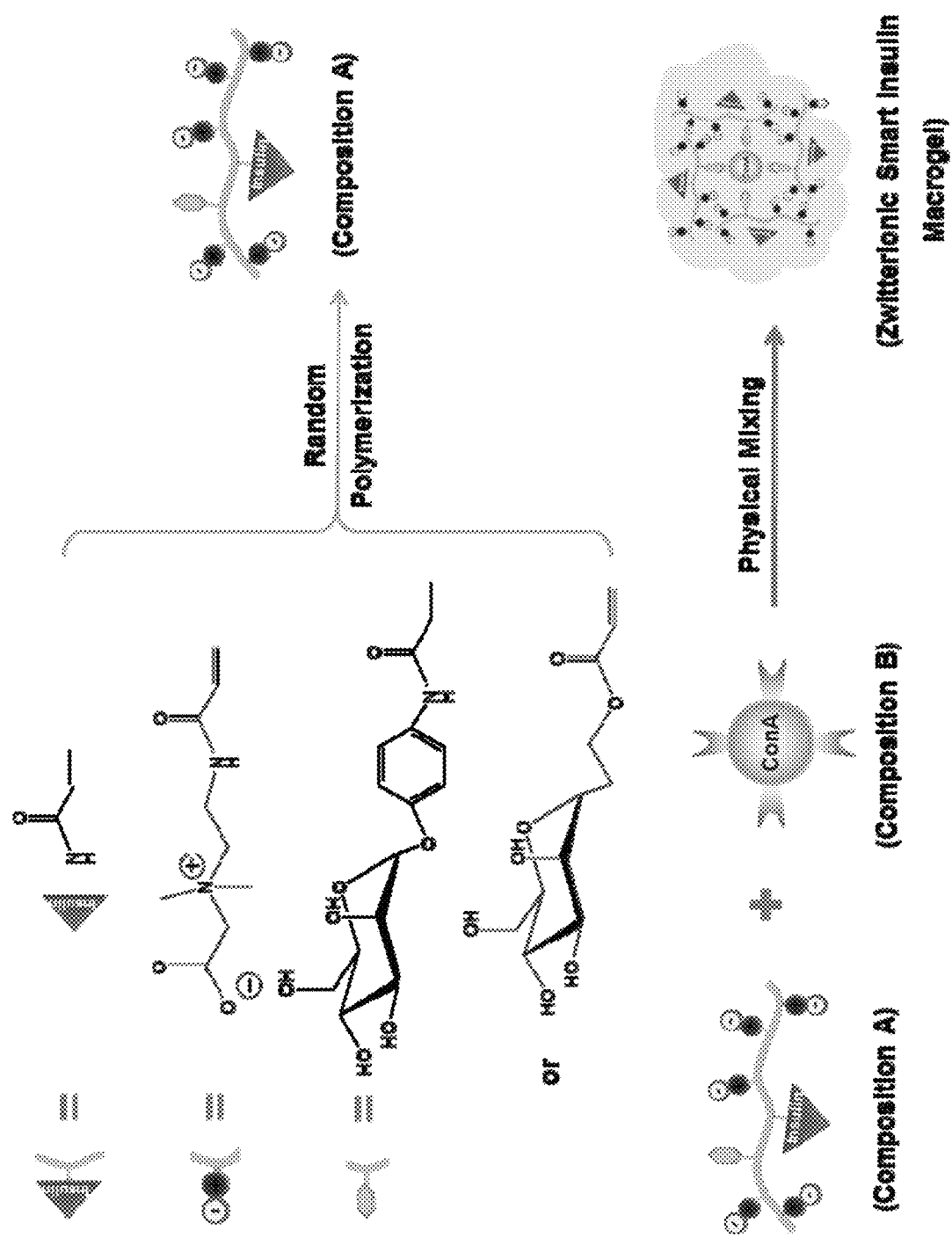
FIG. 6 is a schematic diagram showing synthesis of a zwitterionic polymer-insulin-saccharide composition (Composition A, also called Component A herein) and a glucose-responsive zwitterionic polymer-insulin-saccharide composition (Composition A mixed with Composition B, Composition B is also called Component B herein)

In another embodiment, a mannose-containing monomer, the second mannose-containing monomer structure shown in FIG. 6, can be prepared by reacting 1-C-(2-hydroxyethyl)-2,3,4,6-tetra-O-triethylsilyl α-D-mannopyranoside (a triethylsilyl (TES) protected mannopyranoside alcohol—a mannose derivative) with acryloyl chloride, followed by trifluoroacetic acid treatment to remove TES protecting groups. The TES protected mannopyranoside alcohol can be synthesized from α-D-mannose pentaacetate based on methods described in Mortell, K. H. et al., JACS, 1994. 116(26): 12053-12054; and Joralemon, M. J. et al., Biomacromolecules, 2004. 5(3):903-913. In this reaction, the molar ratio of mannose derivative:acryloyl chloride is in the range of 1:0.1-0.01:1. In certain embodiments, the molar ratio of mannose derivative:acryloyl chloride is in the range of 1:1-1:10. In certain embodiments, the molar ratio of mannose derivative:acryloyl chloride is in the range of 1:1-1:5.

In another embodiment, the mannose-containing monomer is 2-propenyl α-D-mannopyranoside.

In another embodiment, a polysaccharide moiety is incorporated in Component A such as a tri-saccharide, 3,6-di-O-(α-D-mannopyranosyl)-D-mannose.

In other embodiments, Component A comprises a fourth monomer type or even a fifth or more monomer type that contains saccharide having lectin binding capability. For example, both of the two mannose containing monomers shown in FIG. 6 can be used simultaneously. The amount of the total of saccharide-containing monomers in the polymerization reaction mixture for producing a zwitterionic polymer-insulin-saccharide composition (Component A) is in the range of 0.1-90% by weight of the polymerization reaction mixture for producing the zwitterionic polymer-insulin-saccharide composition. In certain embodiments, the amount of the total of saccharide-containing monomers in the polymerization reaction mixture is in the range of 0.1-50% by weight of the polymerization reaction mixture for producing the zwitterionic polymer-insulin-saccharide composition. In certain embodiments, the amount of the total of saccharide-containing monomers in the polymerization reaction mixture is in the range of 0.1-40% by weight of the polymerization reaction mixture for producing the zwitterionic polymer-insulin-saccharide composition. In certain embodiments, the amount of the total of saccharide-containing monomers in the polymerization reaction mixture is in the range of 0.1-30% by weight of the polymerization reaction mixture for producing the zwitterionic polymer-insulin-saccharide composition.

Hydrophobic Monomer

According to aspects of the present disclosure, a hydrophobic monomer such as styrene (vinylbenzene), is included in the polymerization reaction mixture for producing the zwitterionic polymer-insulin-saccharide composition (Component A) during the polymerization reaction to allow for a wide range of hydrophobicity to be achieved by the Component A. The amount of the hydrophobic monomer in the polymerization reaction mixture for producing the zwitterionic polymer-insulin-saccharide composition is in the range of 0-90% by weight of the polymerization reaction mixture for producing the zwitterionic polymer-insulin-saccharide composition. In certain embodiments, the amount of the hydrophobic monomer in the polymerization reaction mixture for producing the zwitterionic polymer-insulin-saccharide composition is in the range of 0-50% by weight of the polymerization reaction mixture for producing the zwitterionic polymer-insulin-saccharide composition. In certain embodiments, the amount of the hydrophobic monomer in the polymerization reaction mixture for producing the zwitterionic polymer-insulin-saccharide composition is in the range of 0-10% by weight of the polymerization reaction mixture for producing the zwitterionic polymer-insulin-saccharide composition. In certain embodiments, the amount of the hydrophobic monomer in the polymerization reaction mixture for producing the zwitterionic polymer-insulin-saccharide composition is in the range of 0-1% by weight of the polymerization reaction mixture for producing the zwitterionic polymer-insulin-saccharide composition. Where the hydrophobic monomer is present, the amount of the hydrophobic monomer in the polymerization reaction mixture for producing the zwitterionic polymer-insulin-saccharide composition is in the range of 0.001-90% by weight of the polymerization reaction mixture for producing the zwitterionic polymer-insulin-saccharide composition, 0.001-50% by weight of the polymerization reaction mixture for producing the zwitterionic polymer-insulin-saccharide composition, 0.001-10% by weight of the polymerization reaction mixture for producing the zwitterionic polymer-insulin-saccharide composition or 0.001-1% by weight of the polymerization reaction mixture for producing the zwitterionic polymer-insulin-saccharide composition.

A hydrophobic monomer according to aspects of present disclosure is any monomer with a water solubility of not more than about 0.02 g/100 g water, including but are not limited to, vinyl esters of branched mono-carboxylic acids having a total of 8 to 12 carbon atoms in the acid residue moiety and 10 to 14 total carbon atoms such as, for example, vinyl 2-ethyl hexanoate, vinyl neo-nonanoate, vinyl neo-decanoate, vinyl neo-undecanoate, vinyl neo-dodecanoate and mixtures thereof, a vinyl ester containing from about 8 to about 12 carbon atoms in the acid residue moiety, branched vinyl esters, branched vinyl ester monomers selected from the group consisting of vinyl pivalate, vinyl neo-nonanoate, vinyl 2-ethyl hexanoate, vinyl neo-decanoate, vinyl neo-undecanoate, vinyl neo-dodecanoate and mixtures thereof.

Additional examples of hydrophobic monomers include vinyl 2-ethylhexanoate, vinyl laurate, vinyl stearate, vinyl alkyl or aryl ethers with ($C_9$-$C_{30}$) alkyl groups such as stearyl vinyl ether; ($C_6$-$C_{30}$) alkyl esters of (meth-)acrylic acid, such as hexyl (meth)acrylate, heptyl (meth)acrylate, octyl (meth)acrylate, isooctyl acrylate, isononyl acrylate, decyl (meth)acrylate, isodecyl (meth)acrylate, dodecyl (meth)acrylate, 2-ethylhexyl (meth)acrylate, benzyl (meth)acrylate, lauryl (meth)acrylate, oleyl (meth)acrylate, palmityl (meth)acrylate, and stearyl (meth)acrylate; unsaturated vinyl esters of (meth)acrylic acid such as those derived from fatty acids and fatty alcohols; monomers derived from cholesterol; olefinic monomers such as 1-butene, 2-butene, 1-pentene, 1-hexene, 1-octene, isobutylene and isoprene; and the like, provided, however, that any monomer that has a solubility of more than about 0.02 g/100 g water is not within the definition of hydrophobic as used herein.

Synthesis of Component A

Provided according to specific aspects of the present disclosure is a method to synthesize a polymerization reaction product of a zwitterionic CBAA monomer (a type of zwitterionic carboxybetaine acrylamide monomer, (3-Acryloylamino-propyl)-(2-carboxy-ethyl)-dimethyl-ammonium, synthesized as previously described in Vaisocherova, H. et al., Analytical Chemistry, 2008; 80:7894-7901.), an insulin-containing monomer and a mannose-containing monomer as Component A, exemplified in Examples herein.

A zwitterionic polymer-insulin-saccharide composition, Component A, including a polymerization reaction product of a zwitterionic monomer, an insulin-containing monomer and a saccharide-containing monomer displays a pharmacodynamic (PD) and/or pharmacokinetic (PK) profile that is sensitive to the concentration of glucose in the environment, such as blood concentration of glucose when implanted in vivo.

A saccharide selected according to the aspects of present disclosure shows stronger binding affinity to human lectins including but not limited to human mannose binding protein (MBP), human mannose receptor, human pulmonary surfactant protein A (SP-1), human pulmonary surfactant protein D, collectin-43, conglutinin, human fucose binding protein, and human fucose receptor, compared to the binding affinity for glucose to the human lectin. The ratio of binding constant, Kb, for a saccharide selected according to the aspects of present disclosure to Kb for glucose is above 1 when the saccharide and the glucose interact with the human lectin selected according to the aspects of present disclosure.

A zwitterionic polymer-insulin-saccharide composition, Component A, displays a pharmacodynamic (PD) and/or pharmacokinetic (PK) profile that is sensitive to the concentration of glucose in the environment, such as blood concentration of glucose when administered to the body.

According to aspects of the present disclosure, a zwitterionic polymer-insulin-saccharide composition, Component A, of the present disclosure binds human lectins at a serum glucose concentration of 60 mg/dL or less when administered to a subject in need thereof.

Component B—Saccharide Binding Molecule

According to aspects of the present disclosure, a glucose-responsive zwitterionic polymer-insulin-saccharide composition includes a saccharide binding molecule (also called Component B or Composition B herein). The saccharide binding molecule binds to the saccharide included in Component A.

A saccharide selected according to the aspects of present disclosure shows stronger binding affinity to a lectin selected according to the aspects of present disclosure, compared to the binding affinity for a glucose to the lectin selected according to the aspects of present disclosure. The ratio of binding constant, Kb, for a saccharide selected according to the aspects of present disclosure to Kb for glucose is above 1 when the saccharide and the glucose interact with the lectin selected according to the aspects of present disclosure.

A glucose-responsive zwitterionic polymer-insulin-saccharide composition displays a releasing profile for Component A that is sensitive to the concentration of glucose in the environment, such as blood concentration of glucose of patients receiving the composition. The release for Component A is facilitated at a high glucose concentration compared at a low glucose concentration, and dis-favored at a low glucose concentration compared at a high glucose concentration. A typical low glucose concentration is in the range of 0-100 mg/dl. A typical high glucose concentration is in the range of above 100 mg/dl.

According to aspects of the present disclosure, a glucose-responsive zwitterionic polymer-insulin-saccharide composition of the present disclosure corrects a hyperglycemia to normal glycemia by facilitating release of Component A at a high glucose concentration, and prevents a hypoglycemia by disfavoring the release of Component A at a low glucose concentration, when administered to a subject in need thereof.

An included saccharide binding molecule binds a saccharide selected from, but not limited to, mannose, fucose, a bisaccharide, a trisaccharide, a tetrasaccharide, a branched trisaccharide, bimannose, trimannose, tetramannose, branched trimannose, glucosamine, a derivative of any thereof or a combination of any thereof.

Optionally, an included saccharide binding molecule is a mannose-selective lectin protein selected from, but not limited to, human mannose binding protein (MBP), human mannose receptor, human pulmonary surfactant protein A (SP-1), human pulmonary surfactant protein D, collectin-43, conglutinin, a phytohemagglutinin, including but not limited to, concanavalin A, phytohemoagglutinins derived from *Galanthus nivalis* (snowdrop), *Pisum sativum* (pea), *Lathyrus odoratus* (sweet pea), *Lens culinaris* (lentil), *Narcissus pseudonarcissus* (daffodil), *Vicia faba* (fava bean), and *Vicia sativa* (garden vetch), a binding fragment thereof, and a combination of any two or more thereof. Optionally, saccharide binding molecules can be covalently linked.

Optionally, an included saccharide binding molecule is a fucose selective lectin protein selected from, but not limited to, human fucose binding protein, human fucose receptor, and exogenous lectins including but not limited to includes *Lotus tetragonolobus* lectin, *Ulex europaeus* agglutinin, *Lens culinaris* agglutinin, *Aleuria aurantia* lectin, *Anguilla* lectin, *Rhizopus stolonifera* lectin, *Ralstonia solanacearum* lectin.

An included saccharide binding molecule can be an endogenous saccharide binding molecule, i.e. expressed by a cell of the human body or an exogenous saccharide binding molecule, i.e. expressed by an organism other than a human, such as a plant. According to particular aspects of the present disclosure, a combination of one or more endogenous saccharide binding molecules and one or more exogenous saccharide binding molecules is included in a composition including a glucose-responsive zwitterionic polymer-insulin-saccharide composition.

According to particular aspects, an endogenous saccharide binding molecule included in a glucose-responsive zwitterionic polymer-insulin-saccharide composition is the human mannose receptor 1.

A glucose-responsive zwitterionic polymer-insulin-saccharide composition according to aspects of the present disclosure includes a zwitterionic polymer-insulin-saccharide composition and a saccharide binding molecule, wherein the ratio of the saccharide binding molecule (Component B):zwitterionic polymer-insulin-saccharide composition (Component A) by weight is in the range of 0.001:1-1:0.001.

Component C

In certain embodiments, the glucose-responsive zwitterionic polymer-insulin-saccharide composition of the present disclosure further includes a component which enhances the tunability of the glucose-responsive zwitterionic polymer-insulin-saccharide composition in controlling the responsiveness to glucose levels and/or the rate of insulin release. The third component, Component C, is or includes a polymerization product of a zwitterionic monomer and a saccharide-containing monomer. The zwitterionic monomer and saccharide-containing monomer polymerized to form Component C may be the same zwitterionic monomer and saccharide-containing monomer polymerized with an insulin-containing monomer to form Component A or may be different.

The ratio of Component C:Component A by weight in a glucose-responsive zwitterionic polymer-insulin-saccharide composition including Component A, B, and C of the present disclosure is in the range of 0.001:1-1:0.001.

Preparation of a Glucose-Responsive Zwitterionic Polymer-Insulin-Saccharide Composition Generally described, to prepare a glucose-responsive zwitterionic polymer-insulin-saccharide composition, Component A is mixed with Component B under conditions which allow for binding of Components A and B.

To prepare a glucose-responsive zwitterionic polymer-insulin-saccharide composition, the saccharide binding molecule or its solution is physically added or mixed with a solution of component A, or Component A or its solution is physically added or mixed to a solution of saccharide binding molecule. The glucose-responsive zwitterionic polymer-insulin-saccharide composition thereby produced is in the form of a gel, a precipitate, or a solution.

In certain embodiments, a glucose-responsive zwitterionic polymer-insulin-saccharide composition includes a mixture of: (1) zwitterionic PCBAA polymer with insulin and mannose attached (Component A), and (2) Con A (type VI) (Component B), as shown schematically in FIG. 6, and methods of synthesis thereof are described herein.

In certain embodiments, a glucose-responsive zwitterionic polymer-insulin-saccharide composition includes a mixture of: (1) a polymerization reaction product of a zwitterionic CBAA monomer, an insulin-containing monomer and a mannose-containing monomer (Component A), and (2) Con A (Component B), as shown schematically in FIG. 6, and methods of synthesis thereof are described herein.

Preparation of a Glucose-Responsive Zwitterionic Polymer-Insulin-Saccharide Composition Including Component C.

Generally described, to prepare a glucose-responsive zwitterionic polymer-insulin-saccharide composition including Component C, Component A is mixed with Component B under conditions which allow for binding of Components A and B (i.e. via binding of the saccharide moiety of Component A with the saccharide binding molecule, Component B), and Component C is mixed with the composition including Component A and B. Alternatively, Component A is mixed with Component C, and Component B is mixed with the composition including Component A and C under conditions which allow for binding of Components A and B, and Components C and B. Alternatively, Component C is mixed with Component B under conditions which allow for binding of Components C and B, and Component A is mixed with the composition including Components C and B.

To prepare a glucose-responsive zwitterionic polymer-insulin-saccharide composition including Component C, the saccharide binding molecule, Component B, or its solution is physically added or mixed with a solution of component A, or Component A or its solution is physically added or mixed to a solution of saccharide binding molecule, Component B. Then Component C or its solution is physically added or mixed with the solution containing Component A and B, or the solution containing Component A and B is physically added or mixed with the solution of Component C. Alternatively, Component C or its solution is physically added or mixed with a solution of component A, or Component A or its solution is physically added or mixed to a solution of Component C. Then Component B or its solution is physically added or mixed with the solution containing Component A and C, or the solution containing Component A and C is physically added or mixed with the solution of Component B. Alternatively, the saccharide binding molecule, Component B, or its solution is physically added or mixed with a solution of component C, or Component C or its solution is physically added or mixed to a solution of saccharide binding molecule, Component B. Then Component A or its solution is physically added or mixed with the solution containing Component C and B, or the solution containing Component C and B is physically added or mixed with the solution of Component A.

The glucose-responsive zwitterionic polymer-insulin-saccharide composition including Component C thereby produced is in the form of a gel, a precipitate, or a solution.

Component B Immobilization

Glucose-Responsive Zwitterionic Polymer-Insulin-Saccharide Compositions According to Aspects of the Disclosure are Provided Wherein Component B is Covalently Bonded to a Second Polymer or Hydrogel to Inhibit Leaching from the Glucose-Responsive Zwitterionic Polymer-Insulin-Saccharide Composition.

A glucose-responsive zwitterionic polymer-insulin-saccharide composition, comprising, in combination: 1) a saccharide binding molecule (also called Component B or Composition B herein); and 2) a polymerization reaction product of a zwitterionic monomer, an insulin-containing monomer, and a saccharide-containing monomer (also called zwitterionic polymer-insulin-saccharide composition, Component A and Composition A herein), is provided wherein the saccharide binding molecule binds to the saccharide of the saccharide-containing monomer in the zwitterionic polymer-insulin-saccharide composition, and wherein the saccharide binding molecule is covalently bound to a second polymer.

For immobilizing saccharide binding molecule, the saccharide binding molecule is covalently linked to one or multiple reactive functional groups (e.g., double bond which can be further polymerized, such as acryloyl functional group), which enables further covalent linkage to a second polymer or hydrogel.

In one embodiment, the saccharide binding molecule is converted to a saccharide binding molecule-containing monomer by following a synthetic method similar to that described for synthesis of the insulin monomer. In a similar reaction the molar ratio of the saccharide binding molecule: acrylic acid derivative is in the range of 1:0.1-0.01:1. In certain embodiments, the molar ratio is in the range of 1:1-1:10. In certain embodiments, the molar ratio is in the range of 1:1-1:5.

A glucose-responsive zwitterionic polymer-insulin-saccharide composition, comprising, in combination: 1) a saccharide binding molecule (also called Component B or Composition B herein); and 2) a polymerization reaction product of a zwitterionic monomer, an insulin-containing monomer, and a saccharide-containing monomer (also called zwitterionic polymer-insulin-saccharide composition, Component A and Composition A herein), is provided wherein the saccharide binding molecule binds to the saccharide of the saccharide-containing monomer in the zwitterionic polymer-insulin-saccharide composition, wherein the saccharide binding molecule is covalently bound to a hydrogel. In one embodiment, the hydrogel is prepared by polymerization of zwitterionic monomers.

To synthesize a glucose-responsive zwitterionic polymer-insulin-saccharide composition, wherein the saccharide binding molecule is covalently bonded to a hydrogel, in one embodiment, the method includes: mixing a saccharide binding molecule-containing monomer and component A, a zwitterionic monomer, a crosslinker, and an initiator together in an aqueous solvent thereby generating a reaction mixture, optionally transferring the reaction mixture into a mold, and forming a hydrogel under conditions that initiate polymerization in the reaction mixture. The resulting glucose-responsive zwitterionic polymer-insulin-saccharide composition wherein the saccharide binding molecule is covalently bonded to a hydrogel is equilibrated such as in sterile PBS and optionally tailored before further use.

A crosslinker included in a reaction mixture according to aspects of the present disclosure is one or more of: allyl methacrylate, diallyl itaconate, monoallyl itaconate, dially maleate, diallyl fumarate, diallyl succinate, diallyl phthalate, triallyl cyanurate, triallyl isocyanurate, diethylene glycol bis-allyl carbonate, divinyl ether of diethylene glycol, triallyl phosphate, triallyl trimellitate, allyl ether, diallylimidazolidone, pentaerythritol triallyl ether (PETE), N,N-diallylmelamine, triallyl-1,3,5-triazine-2,4,6-(1H,3H,5H)trione (TATT), 2,4,6-Triallyloxy-1,3,5-triazine; vinyl compounds, e.g. divinyl benzene, N,N'-methylene bis acrylamide (MBAA), methylenebis(methacrylamide), ethylene glycol dimethacrylate, ethylene glycol diacrylate, neopentylglycol dimethacrylate, tetraethylene glycol dimethacrylate, polyethylene glycol dimethacrylate, polyethylene glycol diacrylate, hexamethylene bis maleimide, divinyl urea, bisphenol A bis methacrylate, divinyl adipate, glycerin trimethacrylate, trimethylolpropane triacrylate, trivinyl trimellitate, 1,5-pentadiene, 1,7-octadiene, 1,9-decadiene, 1,3-bis(4-methacryloxybutyl) tetramethyl disiloxane, divinyl ether, divinyl sulfone, N-vinyl-3(E)-ethylidene pyrrolidone (EVP), ethylidene bis(N-vinyl pyrrolidone) (EBVP).

A crosslinker included in a reaction mixture according to aspects of the present disclosure is MBAA.

The amount of the saccharide binding molecule-containing monomer in the reaction mixture for producing a glucose-responsive zwitterionic polymer-insulin-saccharide composition wherein the saccharide binding molecule is covalently bonded to a hydrogel is in the range of 0.01-95% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the saccharide binding molecule-containing monomer in the reaction mixture for producing the glucose-responsive zwitterionic polymer-insulin-saccharide composition wherein the saccharide binding molecule is covalently bonded to a hydrogel is in the range of 0.01-50% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the saccharide binding molecule-containing monomer in the reaction mixture for producing the glucose-responsive zwitterionic polymer-insulin-saccharide composition wherein the saccharide binding molecule is covalently bonded to a hydrogel is in the range of 0.01-10% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the saccharide binding molecule-containing monomer in the reaction mixture for producing the glucose-responsive zwitterionic polymer-insulin-saccharide composition wherein the saccharide binding molecule is covalently bonded to a hydrogel is in the range of 0.01-5% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the saccharide binding molecule-containing monomer in the reaction mixture for producing the glucose-responsive zwitterionic polymer-insulin-saccharide composition wherein the saccharide binding molecule is covalently bonded to a hydrogel is in the range of 0.01-3% by weight of the reaction mixture (excluding aqueous solvent) for producing the glucose-responsive zwitterionic polymer-insulin-saccharide composition wherein the saccharide binding molecule is covalently bonded to a hydrogel.

The amount of the Component A in the reaction mixture for producing the glucose-responsive zwitterionic polymer-insulin-saccharide composition wherein the saccharide binding molecule is covalently bonded to a hydrogel is in the range of 0.001-90% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the Component A in the reaction mixture for producing the glucose-responsive zwitterionic polymer-insulin-saccharide composition wherein the saccharide binding molecule is covalently bonded to a hydrogel is in the range of 0.001-50% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the Component A in the reaction mixture for producing the glucose-responsive zwitterionic polymer-insulin-saccharide composition wherein the saccharide binding molecule is covalently bonded to a hydrogel is in the range of 0.001-10% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the Component A in the reaction mixture for producing the glucose-responsive zwitterionic polymer-insulin-saccharide composition wherein the saccharide binding molecule is covalently bonded to a hydrogel is in the range of 0.001-5% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the Component A in the reaction mixture for producing the glucose-responsive zwitterionic polymer-insulin-saccharide composition wherein the saccharide binding molecule is covalently bonded to a hydrogel is in the range of 0.001-1% by weight of the reaction mixture (excluding aqueous solvent) for producing the glucose-responsive zwitterionic polymer-insulin-saccharide composition wherein the saccharide binding molecule is covalently bonded to a hydrogel.

The amount of the zwitterionic monomer in the reaction mixture for producing the glucose-responsive zwitterionic polymer-insulin-saccharide composition wherein the saccharide binding molecule is covalently bonded to a hydrogel is in the range of 0.1-99% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the zwitterionic monomer in the reaction mixture for producing the glucose-responsive zwitterionic polymer-insulin-saccharide composition wherein the saccharide binding molecule is covalently bonded to a hydrogel is in the range of 0.1-98% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the zwitterionic monomer in the reaction mixture for producing the glucose-responsive zwitterionic polymer-insulin-saccharide composition wherein the saccharide binding molecule is covalently bonded to a hydrogel is in the range of 0.1-97% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the zwitterionic monomer in the reaction mixture for producing the hydrogel is in the range of 0.1-96% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the zwitterionic monomer in the reaction mixture for producing the hydrogel is in the range of 0.1-95% by weight of the reaction mixture (excluding aqueous solvent) for producing the glucose-responsive zwitterionic polymer-insulin-saccharide composition wherein the saccharide binding molecule is covalently bonded to a hydrogel.

The concentration of the zwitterionic monomer in the aqueous solvent solution of reaction mixture for producing the glucose-responsive zwitterionic polymer-insulin-saccharide composition wherein the saccharide binding molecule is covalently bonded to a hydrogel is in the range of 0.01-2000 mg/ml. In certain embodiments, this concentration is in the range of 0.01-1000 mg/ml. In certain embodiments this concentration is in the range of 0.01-800 mg/ml. In certain embodiments, this concentration is in the range of 0.01-600 mg/ml. In certain embodiments, this concentration is in the range of 0.01-400 mg/ml. In certain embodiments, this concentration is in the range of 0.01-200 mg/ml.

The amount of the crosslinker in the reaction mixture for producing the glucose-responsive zwitterionic polymer-insulin-saccharide composition wherein the saccharide binding molecule is covalently bonded to a hydrogel is in the range of 0.001-90% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the crosslinker in the reaction mixture for producing the glucose-responsive zwitterionic polymer-insulin-saccharide composition wherein the saccharide binding molecule is covalently bonded to a hydrogel is in the range of 0.001-50% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the crosslinker in the reaction mixture for producing the glucose-responsive zwitterionic polymer-insulin-saccharide composition wherein the saccharide binding molecule is covalently bonded to a hydrogel is in the range of 0.001-10% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the crosslinker in the reaction mixture for producing the glucose-responsive zwitterionic polymer-insulin-saccharide composition wherein the saccharide binding molecule is covalently bonded to a hydrogel is in the range of 0.001-5% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the crosslinker in the reaction mixture for producing the glucose-responsive zwitterionic polymer-insulin-saccharide composition wherein the saccharide binding molecule is covalently bonded to a hydrogel is in the range of 0.001-1% by weight of the reaction mixture (excluding aqueous solvent) for producing the glucose-responsive zwitterionic polymer-insulin-saccharide composition wherein the saccharide binding molecule is covalently bonded to a hydrogel.

The amount of the initiator in the reaction mixture for producing the glucose-responsive zwitterionic polymer-insulin-saccharide composition wherein the saccharide binding molecule is covalently bonded to a hydrogel is in the range of 0.001-10% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the initiator in the reaction mixture for producing the glucose-responsive zwitterionic polymer-insulin-saccharide composition wherein the saccharide binding molecule is covalently bonded to a hydrogel is in the range of 0.001-5% by weight of the reaction mixture (excluding aqueous solvent) for producing the glucose-responsive zwitterionic polymer-insulin-saccharide composition wherein the saccharide binding molecule is covalently bonded to a hydrogel. In certain embodiments, the amount of the initiator in the reaction mixture for producing the glucose-responsive zwitterionic polymer-insulin-saccharide composition wherein the saccharide binding molecule is covalently bonded to a hydrogel is in the range of 0.001-1% by weight of the reaction mixture (excluding aqueous solvent) for producing the glucose-responsive zwitterionic polymer-insulin-saccharide composition wherein the saccharide binding molecule is covalently bonded to a hydrogel.

To synthesize the glucose-responsive zwitterionic polymer-insulin-saccharide composition wherein the saccharide binding molecule is covalently bonded to a hydrogel, in one embodiment, the method includes: dissolving the saccharide binding molecule-containing monomer in an aqueous solvent containing glucose, adding or mixing the saccharide binding molecule-containing monomer/glucose solution with Component A at various rates (e.g., dropwise), adding zwitterionic monomer, crosslinker, and initiator into the mixture in aqueous solvent, forming a reaction mixture, optionally transferring the reaction mixture into a mold, and forming a hydrogel under conditions that initiate the polymerization of the mixture. The resulting glucose-responsive zwitterionic polymer-insulin-saccharide composition wherein the saccharide binding molecule is covalently bonded to a hydrogel is equilibrated such as in sterile PBS and optionally tailored before further use.

The glucose concentration is in the range of 0-909 mg/ml in the aqueous solvent to dissolve saccharide binding molecule-containing monomer. In certain embodiments, this concentration is in the range of 0.001-200 mg/ml. In certain embodiments, this concentration is in the range of 0.001-100 mg/ml. In certain embodiments, this concentration is in the range of 0.001-50 mg/ml. In certain embodiments, this concentration is in the range of 0.001-5 mg/ml.

The amount of the saccharide binding molecule-containing monomer in the reaction mixture for forming the glucose-responsive zwitterionic polymer-insulin-saccharide composition wherein the saccharide binding molecule is covalently bonded to a hydrogel is in the range of 0.01-95% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the saccharide binding molecule-containing monomer in the reaction mixture for forming the glucose-responsive zwitterionic polymer-insulin-saccharide composition wherein the saccharide binding molecule is covalently bonded to a hydrogel is in the range of 0.01-50% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the saccharide binding molecule-containing monomer in the reaction mixture for forming the glucose-responsive zwitterionic polymer-insulin-saccharide composition wherein the saccharide binding molecule is covalently bonded to a hydrogel is in the range of 0.01-10% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the saccharide binding molecule-containing monomer in the reaction mixture for forming the glucose-responsive zwitterionic polymer-insulin-saccharide composition wherein the saccharide binding molecule is covalently bonded to a hydrogel is in the range of 0.01-5% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the saccharide binding molecule-containing monomer in the reaction mixture for forming the glucose-responsive zwitterionic polymer-insulin-saccharide composition wherein the saccharide binding molecule is covalently bonded to a hydrogel is in the range of 0.01-3% by weight of the reaction mixture (excluding aqueous solvent and glucose) for forming the glucose-responsive zwitterionic polymer-insulin-saccharide composition wherein the saccharide binding molecule is covalently bonded to a hydrogel.

The amount of the Component A in the reaction mixture for forming a glucose-responsive zwitterionic polymer-insulin-saccharide composition wherein the saccharide binding molecule is covalently bonded to a hydrogel is in the range of 0.001-90% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the Component A in the reaction mixture for forming a glucose-responsive zwitterionic polymer-insulin-saccharide composition wherein the saccharide binding molecule is covalently bonded to a hydrogel is in the range of 0.001-50% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the Component A in the reaction mixture for forming a glucose-responsive zwitterionic polymer-insulin-saccharide composition wherein the saccharide binding molecule is covalently bonded to a hydrogel is in the range of 0.001-10% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the Component A in the reaction mixture for forming a glucose-responsive zwitterionic polymer-insulin-saccharide composition wherein the saccharide binding molecule is covalently bonded to a hydrogel is in the range of 0.001-5% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the Component A in the reaction mixture for forming a glucose-responsive zwitterionic polymer-insulin-saccharide composition wherein the saccharide binding molecule is covalently bonded to a hydrogel is in the range of 0.001-1% by weight of the reaction mixture (excluding aqueous solvent and glucose) for forming the glucose-responsive zwitterionic polymer-insulin-saccharide composition wherein the saccharide binding molecule is covalently bonded to a hydrogel.

The amount of the zwitterionic monomer in the reaction mixture for forming the glucose-responsive zwitterionic polymer-insulin-saccharide composition wherein the saccharide binding molecule is covalently bonded to a hydrogel is in the range of 0.1-99% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the zwitterionic monomer in the reaction mixture for forming the glucose-responsive zwitterionic polymer-insulin-saccharide composition wherein the saccharide binding molecule is covalently bonded to a hydrogel is in the range of 0.1-98% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the zwitterionic monomer in the reaction mixture for forming the glucose-responsive zwitterionic polymer-insulin-saccharide composition wherein the saccharide binding molecule is covalently bonded to a hydrogel is in the range of 0.1-97% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the zwitterionic monomer in the reaction mixture for forming the glucose-responsive zwitterionic polymer-insulin-saccharide composition wherein the saccharide binding molecule is covalently bonded to a hydrogel is in the range of 0.1-96% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the zwitterionic monomer in the reaction mixture for forming the glucose-responsive zwitterionic polymer-insulin-saccharide composition wherein the saccharide binding molecule is covalently bonded to a hydrogel is in the range of 0.1-95% by weight of the reaction mixture (excluding aqueous solvent and glucose) for forming the glucose-responsive zwitterionic polymer-insulin-saccharide composition wherein the saccharide binding molecule is covalently bonded to a hydrogel.

The concentration of the zwitterionic monomer in the aqueous solvent of the reaction mixture for forming the glucose-responsive zwitterionic polymer-insulin-saccharide composition wherein the saccharide binding molecule is covalently bonded to a hydrogel is in the range of 0.01-2000 mg/ml. In certain embodiments, this concentration is in the range of 0.01-1000 mg/ml. In certain embodiments this concentration is in the range of 0.01-800 mg/ml. In certain embodiments, this concentration is in the range of 0.01-600 mg/ml. In certain embodiments, this concentration is in the range of 0.01-400 mg/ml. In certain embodiments, this concentration is in the range of 0.01-200 mg/ml.

The amount of the crosslinker in the reaction mixture for forming the glucose-responsive zwitterionic polymer-insulin-saccharide composition wherein the saccharide binding molecule is covalently bonded to a hydrogel is in the range of 0.001-90% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the crosslinker in the reaction mixture for forming the hydrogel is in the range of 0.001-50% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the crosslinker in the reaction mixture for forming the glucose-responsive zwitterionic polymer-insulin-saccharide composition wherein the saccharide binding molecule is covalently bonded to a hydrogel is in the range of 0.001-10% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the crosslinker in the reaction mixture for forming the glucose-responsive zwitterionic polymer-insulin-saccharide composition wherein the saccharide binding molecule is covalently bonded to a hydrogel is in the range of 0.001-5% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the crosslinker in the reaction mixture for forming the glucose-responsive zwitterionic polymer-insulin-saccharide composition wherein the saccharide binding molecule is covalently bonded to a hydrogel is in the range of 0.001-1% by weight of the reaction mixture (excluding aqueous solvent and glucose) for forming the glucose-responsive zwitterionic polymer-insulin-saccharide composition wherein the saccharide binding molecule is covalently bonded to a hydrogel.

The amount of the initiator in the reaction mixture for forming the glucose-responsive zwitterionic polymer-insulin-saccharide composition wherein the saccharide binding molecule is covalently bonded to a hydrogel is in the range of 0.001-10% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the initiator in the reaction mixture for forming the hydrogel is in the range of 0.001-5% by weight of the reaction mixture (excluding aqueous solvent and glucose) for forming the glucose-responsive zwitterionic polymer-insulin-saccharide composition wherein the saccharide binding molecule is covalently bonded to a hydrogel. In certain embodiments, the amount of the initiator in the reaction mixture for forming the glucose-responsive zwitterionic polymer-insulin-saccharide composition wherein the saccharide binding molecule is covalently bonded to a hydrogel is in the range of 0.001-1% by weight of the reaction mixture (excluding aqueous solvent and glucose) for forming the glucose-responsive zwitterionic polymer-insulin-saccharide composition wherein the saccharide binding molecule is covalently bonded to a hydrogel.

To synthesize a glucose-responsive zwitterionic polymer-insulin-saccharide composition wherein the saccharide binding molecule is covalently bonded to a hydrogel, in one embodiment, the method includes: forming a reaction mixture containing a saccharide binding molecule-containing monomer, a zwitterionic monomer, a crosslinker and an initiator in an aqueous solvent, optionally transferring the reaction mixture into a mold, and then forming a hydrogel under conditions that initiate polymerization of the mixture, equilibrating the resulting hydrogel in sterile solution, such as PBS either with or without glucose, to remove unreacted components and optionally tailor the hydrogel, equilibrating the resulting hydrogel in an aqueous solvent containing glucose and Component A, and equilibrating the resulting glucose-responsive zwitterionic polymer-insulin-saccharide composition wherein the saccharide binding molecule is covalently bonded to a hydrogel in a solution containing no glucose such as PBS while Component A is retained by the matrix. The resulting glucose-responsive zwitterionic polymer-insulin-saccharide composition wherein the saccharide binding molecule is covalently bonded to a hydrogel is ready for further use.

The glucose solution used to equilibrate the resulting hydrogel has a concentration in the range of 0.001-909 mg/ml. In certain embodiments, this concentration is in the range of 0.001-200 mg/ml. In certain embodiments, this concentration is in the range of 0.001-100 mg/ml. In certain embodiments, this concentration is in the range of 0.001-50 mg/ml. In certain embodiments, this concentration is in the range of 0.001-5 mg/ml. The glucose used in the aqueous solvent to contain Component A has a concentration in the range of 0.001-909 mg/ml. In certain embodiments, this concentration is in the range of 0.001-200 mg/ml. In certain embodiments, this concentration is in the range of 0.001-100 mg/ml. In certain embodiments, this concentration is in the range of 0.001-50 mg/ml. In certain embodiments, this concentration is in the range of 0.001-5 mg/ml.

The amount of the saccharide binding molecule-containing monomer in the reaction mixture for forming the hydrogel is in the range of 0.01-95% by weight of the reaction mixture (excluding aqueous solvent) for forming the hydrogel. In certain embodiments, the amount of the saccharide binding molecule-containing monomer in the reaction mixture for forming the hydrogel is in the range of 0.01-50% by weight of the reaction mixture (excluding aqueous solvent) for forming the hydrogel. In certain embodiments, the amount of the saccharide binding molecule-containing monomer in the reaction mixture for forming the hydrogel is in the range of 0.01-10% by weight of the reaction mixture (excluding aqueous solvent) for forming the hydrogel. In certain embodiments, the amount of the saccharide binding molecule-containing monomer in the reaction mixture for forming the hydrogel is in the range of 0.01-5% by weight of the reaction mixture (excluding aqueous solvent) for forming the hydrogel. In certain embodiments, the amount of the saccharide binding molecule-containing monomer in the reaction mixture for forming the hydrogel is in the range of 0.01-3% by weight of the reaction mixture (excluding aqueous solvent) for forming the hydrogel.

The amount of the zwitterionic monomer in the reaction mixture for forming the hydrogel is in the range of 0.1-99% by weight of the reaction mixture (excluding aqueous solvent) for forming the hydrogel. In certain embodiments, the amount of the zwitterionic monomer in the reaction mixture for forming the hydrogel is in the range of 0.1-98% by weight of the reaction mixture (excluding aqueous solvent) for forming the hydrogel. In certain embodiments, the amount of the zwitterionic monomer in the reaction mixture for forming the hydrogel is in the range of 0.1-97% by weight of the reaction mixture (excluding aqueous solvent) for forming the hydrogel. In certain embodiments, the amount of the zwitterionic monomer in the reaction mixture for forming the hydrogel is in the range of 0.1-96% by weight of the reaction mixture (excluding aqueous solvent) for forming the hydrogel. In certain embodiments, the amount of the zwitterionic monomer in the reaction mixture for forming the hydrogel is in the range of 0.1-95% by weight of the reaction mixture (excluding aqueous solvent) for forming the hydrogel.

The concentration of the zwitterionic monomer in the aqueous solvent of the reaction mixture for forming the hydrogel is in the range of 0.01-2000 mg/ml. In certain embodiments, this concentration is in the range of 0.01-1000 mg/ml. In certain embodiments this concentration is in the range of 0.01-800 mg/ml. In certain embodiments, this concentration is in the range of 0.01-600 mg/ml. In certain embodiments, this concentration is in the range of 0.01-400 mg/ml. In certain embodiments, this concentration is in the range of 0.01-200 mg/ml.

The amount of the crosslinker in the reaction mixture for forming the hydrogel is in the range of 0.001-90% by weight of the reaction mixture (excluding aqueous solvent) for forming the hydrogel. In certain embodiments, the amount of the crosslinker in the reaction mixture for forming the hydrogel is in the range of 0.001-50% by weight of the reaction mixture (excluding aqueous solvent) for forming the hydrogel. In certain embodiments, the amount of the crosslinker in the reaction mixture for forming the hydrogel is in the range of 0.001-10% by weight of the reaction mixture (excluding aqueous solvent) for forming the hydrogel. In certain embodiments, the amount of the crosslinker in the reaction mixture for forming the hydrogel is in the range of 0.001-5% by weight of the reaction mixture (excluding aqueous solvent) for forming the hydrogel. In certain embodiments, the amount of the crosslinker in the reaction mixture for forming the hydrogel is in the range of 0.001-1% by weight of the reaction mixture (excluding aqueous solvent) for forming the hydrogel.

The amount of the initiator in the reaction mixture for forming the hydrogel is in the range of 0.001-10% by weight of the reaction mixture (excluding aqueous solvent) for forming the hydrogel. In certain embodiments, the amount of the initiator in the reaction mixture for forming the hydrogel is in the range of 0.001-5% by weight of the reaction mixture (excluding aqueous solvent) for forming the hydrogel. In certain embodiments, the amount of the initiator in the reaction mixture for forming the hydrogel is in the range of 0.001-1% by weight of the reaction mixture (excluding aqueous solvent) for forming the hydrogel.

The concentration of the Component A used in the aqueous solvent is in the range of 0.01-1000 mg/ml. In certain embodiments, this concentration is in the range of 0.01-500 mg/ml. In certain embodiments, this concentration is in the range of 0.01-100 mg/ml. In certain embodiments, this concentration is in the range of 0.01-50 mg/ml. In certain embodiments, this concentration is in the range of 0.01-10 mg/ml.

The amount the Component A that can be absorbed and retained by the hydrogel is in the range of 0.001-90% by weight of the total hydrogel (including Component A and excluding aqueous solvent). In certain embodiments, the amount the Component A that can be absorbed and retained by the hydrogel is in the range of 0.001-50% by weight of the total hydrogel (including Component A and excluding aqueous solvent). In certain embodiments, the amount the Component A that can be absorbed and retained by the hydrogel is in the range of 0.001-10% by weight of the total hydrogel (including Component A and excluding aqueous solvent). In certain embodiments, the amount the Component A that can be absorbed and retained by the hydrogel is in the range of 0.001-5% by weight of the total hydrogel (including Component A and excluding aqueous solvent). In certain embodiments, the amount the Component A that can be absorbed and retained by the hydrogel is in the range of 0.001-1% by weight of the total hydrogel (including Component A and excluding aqueous solvent).

In certain embodiments, any saccharide binding molecule-immobilized hydrogel (e.g., having porous structures, via a microtemplating method) is used to interact and contain Component A. The Component A loading process is controlled by the environmental glucose concentration: at high glucose level, Component A diffusion to the inner part of the matrix is facilitated (Component A binding to Con A is weakened); at low glucose level, Component A can be stably retained by and loaded into the matrix (Component A binding to Con A is highly strengthened).

In one embodiment, the glucose-responsive zwitterionic polymer-insulin-saccharide composition in combination of a saccharide binding molecule and component A, wherein the saccharide binding molecule is covalently bound to a second polymer, wherein the second polymer is prepared from zwitterionic monomers.

To synthesize the glucose-responsive zwitterionic polymer-insulin-saccharide composition wherein the saccharide binding molecule is covalently bonded to a second polymer, in one embodiment, the method includes: forming a saccharide binding molecule-containing polymer by initiating the polymerization of a mixture containing saccharide binding molecule-containing monomer, zwitterionic monomer, and initiator in an aqueous solvent producing a saccharide binding molecule covalently bonded to second polymer, adding or mixing the resulting saccharide binding molecule covalently bonded to second polymer, either in the product rough solution or after purification, with Component A at various rates (e.g., dropwise) in an aqueous solvent, thereby producing a glucose-responsive zwitterionic polymer-insulin-saccharide composition wherein the saccharide binding molecule is covalently bonded to a second polymer. In a preferred option, the product is further covalently bound to a hydrogel by adding zwitterionic monomer, crosslinker, and initiator to produce a reaction mixture, optionally transferring the reaction mixture into a mold, and forming a hydrogel under conditions that initiate polymerization of the reaction mixture. The resulting hydrogel product is equilibrated such as in sterile PBS and optionally tailored before further use.

In the mixture to form a saccharide binding molecule-containing polymer, the amount of the saccharide binding molecule-containing monomer is in the range of 0.01-95% by weight of the reaction mixture (excluding aqueous solvent) for forming the saccharide binding molecule-containing polymer. In certain embodiments, the amount of the saccharide binding molecule-containing monomer is in the range of 0.01-50% by weight of the reaction mixture (excluding aqueous solvent) for forming the saccharide binding molecule-containing polymer. In certain embodiments, the amount of the saccharide binding molecule-containing monomer is in the range of 0.01-10% by weight of the reaction mixture (excluding aqueous solvent) for forming the saccharide binding molecule-containing polymer. In certain embodiments, the amount of the saccharide binding molecule-containing monomer is in the range of 0.01-5% by weight of the reaction mixture (excluding aqueous solvent) for forming the saccharide binding molecule-containing polymer. In certain embodiments, the amount of the saccharide binding molecule-containing monomer is in the range of 0.01-3% by weight of the reaction mixture (excluding aqueous solvent) for forming the saccharide binding molecule-containing polymer.

In the mixture to form a saccharide binding molecule-containing polymer, the amount of the zwitterionic monomer is in the range of 0.1-99% by weight of the reaction mixture (excluding aqueous solvent) for forming the saccharide binding molecule-containing polymer. In certain embodiments, the amount of the zwitterionic monomer is in the range of 0.1-98% by weight of the reaction mixture (excluding aqueous solvent) for forming the saccharide binding molecule-containing polymer. In certain embodiments, the amount of the zwitterionic monomer is in the range of 0.1-97% by weight of the reaction mixture (excluding aqueous solvent) for forming the saccharide binding molecule-containing polymer. In certain embodiments, the amount of the zwitterionic monomer is in the range of 0.1-96% by weight of the reaction mixture (excluding aqueous solvent) for forming the saccharide binding molecule-containing polymer. In certain embodiments, the amount of the zwitterionic monomer is in the range of 0.1-95% by weight of the reaction mixture (excluding aqueous solvent) for forming the saccharide binding molecule-containing polymer.

In the mixture to form a saccharide binding molecule-containing polymer, the concentration of the zwitterionic monomer in the aqueous solvent of the reaction mixture for forming the saccharide binding molecule-containing polymer is in the range of 0.01-2000 mg/ml. In certain embodiments, this concentration is in the range of 0.01-1000 mg/ml. In certain embodiments this concentration is in the range of 0.01-800 mg/ml. In certain embodiments, this concentration is in the range of 0.01-600 mg/ml. In certain embodiments, this concentration is in the range of 0.01-400 mg/ml. In certain embodiments, this concentration is in the range of 0.01-200 mg/ml.

In the reaction mixture to form a saccharide binding molecule-containing polymer, the amount of the initiator is in the range of 0.001-10% by weight of the reaction mixture (excluding aqueous solvent) for forming the saccharide binding molecule-containing polymer. In certain embodiments, the amount of the initiator is in the range of 0.001-5% by weight of the reaction mixture (excluding aqueous solvent) for forming the saccharide binding molecule-containing polymer. In certain embodiments, the amount of the initiator is in the range of 0.001-1% by weight of the reaction mixture (excluding aqueous solvent) for forming the saccharide binding molecule-containing polymer.

In the reaction mixture to form the glucose-responsive zwitterionic polymer-insulin-saccharide composition wherein the saccharide binding molecule is covalently bonded to a second polymer and wherein the composition is further covalently bound to a hydrogel, producing a hydrogel-bonded composition, the amount of the saccharide binding molecule-containing polymer in the reaction mixture for forming the hydrogel-bonded composition is in the range of 0.1-99% by weight of the reaction mixture (excluding aqueous solvent) for forming the hydrogel-bonded composition. In certain embodiments, the amount of the saccharide binding molecule-containing polymer in the reaction mixture for forming the hydrogel-bonded composition is in the range of 0.1-90% by weight of the reaction mixture (excluding aqueous solvent) for forming the hydrogel-bonded composition. In certain embodiments, the amount of the saccharide binding molecule-containing polymer in the reaction mixture for forming the hydrogel-bonded composition is in the range of 0.1-80% by weight of the reaction mixture (excluding aqueous solvent) for forming the hydrogel-bonded composition. In certain embodiments, the amount of the saccharide binding molecule-containing polymer in the reaction mixture for forming the hydrogel-bonded composition is in the range of 0.1-70% by weight of the reaction mixture (excluding aqueous solvent) for forming the hydrogel-bonded composition.

In the mixture to form the hydrogel product, the amount of composition A in the reaction mixture is in the range of 0.001-95% by weight of the reaction mixture (excluding aqueous solvent) for forming the hydrogel-bonded composition. In certain embodiments, the amount of composition A in the reaction mixture is in the range of 0.001-50% by weight of the reaction mixture (excluding aqueous solvent) for forming the hydrogel-bonded composition. In certain embodiments, the amount of composition A in the reaction mixture is in the range of 0.001-10% by weight of the reaction mixture (excluding aqueous solvent) for forming the hydrogel-bonded composition. In certain embodiments, the amount of composition A in the reaction mixture is in the range of 0.001-5% by weight of the reaction mixture (excluding aqueous solvent) for forming the hydrogel-bonded composition. In certain embodiments, the amount of composition A in the reaction mixture is in the range of 0.001-1% by weight of the reaction mixture (excluding aqueous solvent) for forming the hydrogel-bonded composition.

In the mixture to form the hydrogel product, the amount of the zwitterionic monomer is in the range of 0.01-99% by weight of the reaction mixture (excluding aqueous solvent) for forming the hydrogel-bonded composition. In certain embodiments, the amount of the zwitterionic monomer is in the range of 0.01-70% by weight of the reaction mixture (excluding aqueous solvent) for forming the hydrogel-bonded composition. In certain embodiments, the amount of the zwitterionic monomer is in the range of 0.01-50% by weight of the reaction mixture (excluding aqueous solvent) for forming the hydrogel-bonded composition. In certain embodiments, the amount of the zwitterionic monomer is in the range of 0.01-25% by weight of the reaction mixture (excluding aqueous solvent) for forming the hydrogel-bonded composition.

In the mixture to form the hydrogel product, the concentration of the zwitterionic monomer in the aqueous solvent of the reaction mixture for forming the hydrogel-bonded composition is in the range of 0.01-2000 mg/ml. In certain embodiments, this concentration is in the range of 0.01-1000 mg/ml. In certain embodiments, this concentration is in the range of 0.01-800 mg/ml. In certain embodiments, this concentration is in the range of 0.01-600 mg/ml. In certain embodiments, this concentration is in the range of 0.01-400 mg/ml. In certain embodiments, this concentration is in the range of 0.01-200 mg/ml.

In the mixture to form the hydrogel product, the amount of the crosslinker is in the range of 0.001-95% by weight of the reaction mixture (excluding aqueous solvent) for forming the hydrogel-bonded composition. In certain embodiments, the amount of the crosslinker is in the range of 0.001-50% by weight of the reaction mixture (excluding aqueous solvent) for forming the hydrogel-bonded composition. In certain embodiments, the amount of the crosslinker is in the range of 0.001-10% by weight of the reaction mixture (excluding aqueous solvent) for forming the hydrogel-bonded composition. In certain embodiments, the amount of the crosslinker is in the range of 0.001-5% by weight of the reaction mixture (excluding aqueous solvent) for forming the hydrogel-bonded composition. In certain embodiments, the amount of the crosslinker is in the range of 0.001-1% by weight of the reaction mixture (excluding aqueous solvent) for forming the hydrogel-bonded composition.

In the mixture to form the hydrogel product, the amount of the initiator is in the range of 0.001-10% by weight of the reaction mixture (excluding aqueous solvent) for forming the hydrogel-bonded composition. In certain embodiments, the amount of the initiator is in the range of 0.001-5% by weight of the reaction mixture (excluding aqueous solvent) for forming the hydrogel-bonded composition. In certain embodiments, the amount of the initiator is in the range of 0.001-1% by weight of the reaction mixture (excluding aqueous solvent) for forming the hydrogel-bonded composition.

Provided according to aspects of the present disclosure are novel glucose-responsive zwitterionic polymer-insulin-saccharide compositions and several synthesis protocols to obtain a novel glucose-responsive zwitterionic polymer-insulin-saccharide composition including ConA and a polymerization reaction product of a zwitterionic CBAA monomer, an insulin-containing monomer and a mannose-containing monomer as Component A, wherein ConA is covalently bound to a second polymer, or hydrogel, exemplified in Examples herein.

The glucose-responsive zwitterionic polymer-insulin-saccharide composition of Component A, a combination of a saccharide binding molecule and Component A, or a combination of a saccharide binding molecule and Component A wherein the saccharide binding molecule is covalently bound to a second polymer, or hydrogel, further including a hydrogel carrier, where the composition is encapsulated by the hydrogel carrier.

In certain embodiments, the hydrogel carrier is selected from a biocompatible hydrogel, wherein the biocompatible hydrogel comprises a physical hydrogel, a chemical hydrogel or both a physical hydrogel and a chemical hydrogel, wherein 1) the physical hydrogel comprises: a) a non-zwitterionic physical hydrogel-forming polymer; and one or more of: a zwitterionic polymer, a branched zwitterionic copolymer, and a zwitterionic copolymer containing a physical gel-forming polymer; b) a zwitterionic copolymer containing a physical gel-forming polymer; c) a zwitterionic polymer and/or a branched zwitterionic copolymer; and a zwitterionic copolymer containing a physical gel-forming polymer; and d) a mixture of any two or more of a), b) and c); and wherein the chemical hydrogel comprises one or more of: 2) a polymerization product of a zwitterionic monomer and a non-zwitterionic crosslinker, a polymerization product of a zwitterionic monomer and a zwitterionic copolymer comprising one or more functional groups reactive with the zwitterionic monomer, and a polymerization product of a first zwitterionic copolymer comprising reactive functional groups and a second zwitterionic copolymer comprising reactive functional groups, wherein the first and second zwitterionic copolymers are identical or different. Example biocompatible hydrogels are usefuls as carriers described in detail in WO 2016/138528, incorporated herein by reference.

To synthesize the glucose-responsive zwitterionic polymer-insulin-saccharide composition of Component A, a combination of a saccharide binding molecule and Component A, or a combination of a saccharide binding molecule and Component A wherein the saccharide binding molecule is covalently bound to a second polymer, or hydrogel, further including a hydrogel carrier, where the composition is encapsulated by the hydrogel carrier, in one embodiment, the method includes: adding or mixing the glucose-responsive zwitterionic polymer-insulin-saccharide composition of Component A, a combination of a saccharide binding molecule and Component A, or a combination of a saccharide binding molecule and Component A, wherein the saccharide binding molecule is covalently bound to a second polymer, or hydrogel, with a pre-gel mixture containing a zwitterionic monomer, a crosslinker, and an initiator in an aqueous solvent, optionally transferring the pre-gel mixture into a mold, and forming a hydrogel under conditions that initiate the polymerization of the pre-gel mixture. The resulting hydrogel encapsulated product is equilibrated, such as in sterile PBS, and optionally tailored before further use.

The amount of the zwitterionic monomer in the pre-gel mixture is in the range of 0.1-99.99% by weight of the pre-gel mixture (excluding aqueous solvent) for forming the hydrogel. In certain embodiments, the amount of the zwitterionic monomer in the pre-gel mixture is in the range of 0.1-98% by weight of the pre-gel mixture (excluding aqueous solvent) for forming the hydrogel. In certain embodiments, the amount of the zwitterionic monomer in the pre-gel mixture is in the range of 0.1-97% by weight of the pre-gel mixture (excluding aqueous solvent) for forming the hydrogel. In certain embodiments, the amount of the zwitterionic monomer in the pre-gel mixture is in the range of 0.1-96% by weight of the pre-gel mixture (excluding aqueous solvent) for forming the hydrogel. In certain embodiments, the amount of the zwitterionic monomer in the pre-gel mixture is in the range of 0.1-95% by weight of the pre-gel mixture (excluding aqueous solvent) for forming the hydrogel.

The concentration of the zwitterionic monomer in the aqueous solvent of the pre-gel mixture for forming the hydrogel is in the range of 0.01-2000 mg/ml. In certain embodiments, this concentration is in the range of 0.01-1000 mg/ml. In certain embodiments, this concentration is in the range of 0.01-800 mg/ml. In certain embodiments, this concentration is in the range of 0.01-600 mg/ml. In certain embodiments, this concentration is in the range of 0.01-400 mg/ml. In certain embodiments, this concentration is in the range of 0.01-200 mg/ml.

The amount of the crosslinker in the pre-gel mixture is in the range of 0.001-90% by weight of the pre-gel mixture (excluding aqueous solvent) for forming the hydrogel. In certain embodiments, the amount of the crosslinker in the pre-gel mixture is in the range of 0.001-50% by weight of the pre-gel mixture (excluding aqueous solvent) for forming the hydrogel. In certain embodiments, the amount of the crosslinker in the pre-gel mixture is in the range of 0.001-10% by weight of the pre-gel mixture (excluding aqueous solvent) for forming the hydrogel. In certain embodiments, the amount of the crosslinker in the pre-gel mixture is in the range of 0.001-5% by weight of the pre-gel mixture (excluding aqueous solvent) for forming the hydrogel. In certain embodiments, the amount of the crosslinker in the pre-gel mixture is in the range of 0.001-1% by weight of the pre-gel mixture (excluding aqueous solvent) for forming the hydrogel. In certain embodiments, the amount of the crosslinker in the pre-gel mixture is in the range of 0.001-0.1% by weight of the pre-gel mixture (excluding aqueous solvent) for forming the hydrogel.

The amount of the initiator in the pre-gel mixture is in the range of 0.001-10% by weight of the pre-gel mixture (excluding aqueous solvent) for forming the hydrogel. In certain embodiments, the amount of the initiator in the pre-gel mixture is in the range of 0.001-5% by weight of the pre-gel mixture (excluding aqueous solvent) for forming the hydrogel. In certain embodiments, the amount of the initiator in the pre-gel mixture is in the range of 0.001-1% by weight of the pre-gel mixture (excluding aqueous solvent) for forming the hydrogel.

The pore size and dimension of hydrogel carrier plays the function of controlling the transport of glucose and Component A through the hydrogel matrix and influences the responsiveness to glucose levels and/or the rate of release of insulin-containing Component A from the glucose-responsive zwitterionic polymer-insulin-saccharide composition.

According to aspects of the present disclosure, the pore size of the hydrogel carrier is in the range of about 2 nm to 500 μm, and the dimension of the hydrogel carrier is in the range of 10 nm to 50 cm.

Provided according to aspects of the present disclosure are novel glucose-responsive zwitterionic polymer-insulin-saccharide compositions and several synthesis protocols to obtain a novel glucose-responsive zwitterionic polymer-insulin-saccharide composition of a polymerization reaction product of a zwitterionic CBAA monomer, an insulin-containing monomer and a mannose-containing monomer as component A, further encapsulated by zwitterionic PCBAA chemical hydrogel, and a composition comprising ConA and a polymerization reaction product of a zwitterionic CBAA monomer, an insulin-containing monomer and a mannose-containing monomer as Component A, further encapsulated by zwitterionic PCBAA chemical hydrogel, exemplified in Examples herein.

A hydrogel carrier or barrier for glucose-responsive release of insulin, or zwitterionic polymer-insulin-saccharide composition according to aspects of the present disclosure, comprising a zwitterionic polymer, a saccharide, and a saccharide binding molecule.

In one embodiment, the hydrogel carrier or barrier for glucose-responsive release of insulin, or zwitterionic polymer-insulin-saccharide composition according to aspects of the present disclosure, comprises a polymerization reaction product of a zwitterionic monomer, a saccharide-containing monomer, and a saccharide binding molecule-containing monomer according to aspects of the present disclosure.

To synthesize the hydrogel carrier or barrier for glucose-responsive release of insulin, or zwitterionic polymer-insulin-saccharide composition according to aspects of the present disclosure, includes a polymerization reaction product of a zwitterionic monomer, a saccharide-containing monomer, and a saccharide binding molecule-containing monomer according to aspects of the present disclosure, in one embodiment, the method includes: forming a reaction mixture containing a zwitterionic monomer, a saccharide-containing monomer, a saccharide binding molecule-containing monomer, and an initiator in an aqueous solvent in presence of glucose, initiating the reaction under conditions that initiate the polymerization of the reaction mixture. The resulting polymer product is dialyzed against an aqueous solvent in presence of glucose and then dialyzed against an aqueous solvent without glucose to obtain the hydrogel carrier or barrier.

The amount of the saccharide binding molecule-containing monomer in the polymerization reaction mixture for producing a hydrogel carrier or barrier is in the range of 0.01-95% by weight of the polymerization reaction mixture (excluding aqueous solvent and glucose) for producing the hydrogel carrier or barrier. In certain embodiments, the amount of the saccharide binding molecule-containing monomer in the polymerization reaction mixture for producing a hydrogel carrier or barrier is in the range of 0.01-50% by weight of the polymerization reaction mixture (excluding aqueous solvent and glucose) for producing the hydrogel carrier or barrier. In certain embodiments, the amount of the saccharide binding molecule-containing monomer in the polymerization reaction mixture for producing a hydrogel carrier or barrier is in the range of 0.01-10% by weight of the polymerization reaction mixture (excluding aqueous solvent and glucose) for producing the hydrogel carrier or barrier. In certain embodiments, the amount of the saccharide binding molecule-containing monomer in the polymerization reaction mixture for producing a hydrogel carrier or barrier is in the range of 0.01-5% by weight of the polymerization reaction mixture (excluding aqueous solvent and glucose) for producing the hydrogel carrier or barrier. In certain embodiments, the amount of the saccharide binding molecule-containing monomer in the polymerization reaction mixture for producing a hydrogel carrier or barrier is in the range of 0.01-3% by weight of the polymerization reaction mixture (excluding aqueous solvent and glucose) for producing the hydrogel carrier or barrier.

The amount of the saccharide-containing monomer in the polymerization reaction mixture for producing a hydrogel carrier or barrier is in the range of 0.001-90% by weight of the polymerization reaction mixture (excluding aqueous solvent and glucose) for producing the hydrogel carrier or barrier. In certain embodiments, the amount of the saccharide-containing monomer in the polymerization reaction mixture for producing a hydrogel carrier or barrier is in the range of 0.001-50% by weight of the polymerization reaction mixture (excluding aqueous solvent and glucose) for producing the hydrogel carrier or barrier. In certain embodiments, the amount of the saccharide-containing monomer in the polymerization reaction mixture for producing a hydrogel carrier or barrier is in the range of 0.001-10% by weight of the polymerization reaction mixture (excluding aqueous solvent and glucose) for producing the hydrogel carrier or barrier. In certain embodiments, the amount of the saccharide-containing monomer in the polymerization reaction mixture for producing a hydrogel carrier or barrier is in the range of 0.001-5% by weight of the polymerization reaction mixture (excluding aqueous solvent and glucose) for producing the hydrogel carrier or barrier. In certain embodiments, the amount of the saccharide-containing monomer in the polymerization reaction mixture for producing a hydrogel carrier or barrier is in the range of 0.001-1% by weight of the polymerization reaction mixture (excluding aqueous solvent and glucose) for producing the hydrogel carrier or barrier. In certain embodiments, the amount of the saccharide-containing monomer in the polymerization reaction mixture for producing a hydrogel carrier or barrier is in the range of 0.001-0.5% by weight of the polymerization reaction mixture (excluding aqueous solvent and glucose) for producing the hydrogel carrier or barrier.

The amount of the zwitterionic monomer in the polymerization reaction mixture for producing a hydrogel carrier or barrier is in the range of 0.1-99% by weight of the polymerization reaction mixture (excluding aqueous solvent and glucose) for producing the hydrogel carrier or barrier. In certain embodiments, the amount of the zwitterionic monomer in the polymerization reaction mixture for producing a hydrogel carrier or barrier is in the range of 0.1-98% by weight of the polymerization reaction mixture (excluding aqueous solvent and glucose) for producing the hydrogel carrier or barrier. In certain embodiments, the amount of the zwitterionic monomer in the polymerization reaction mixture for producing a hydrogel carrier or barrier is in the range of 0.1-97% by weight of the polymerization reaction mixture (excluding aqueous solvent and glucose) for producing the hydrogel carrier or barrier. In certain embodiments, the amount of the zwitterionic monomer in the polymerization reaction mixture for producing a hydrogel carrier or barrier is in the range of 0.1-96% by weight of the polymerization reaction mixture (excluding aqueous solvent and glucose) for producing the hydrogel carrier or barrier. In certain embodiments, the amount of the zwitterionic monomer in the polymerization reaction mixture for producing a hydrogel carrier or barrier is in the range of 0.1-95% by weight of the polymerization reaction mixture (excluding aqueous solvent and glucose) for producing the hydrogel carrier or barrier.

The concentration of the zwitterionic monomer in the aqueous solvent of the polymerization reaction mixture for producing a hydrogel carrier or barrier is in the range of 0.01-2000 mg/ml. In certain embodiments, this concentration is in the range of 0.01-1000 mg/ml. In certain embodiments this concentration is in the range of 0.01-800 mg/ml. In certain embodiments, this concentration is in the range of 0.01-600 mg/ml. In certain embodiments, this concentration is in the range of 0.01-400 mg/ml. In certain embodiments, this concentration is in the range of 0.01-200 mg/ml.

The amount of the initiator in the polymerization reaction mixture for producing a hydrogel carrier or barrier is in the range of 0.001-10% by weight of the polymerization reaction mixture (excluding aqueous solvent and glucose) for producing the hydrogel carrier or barrier. In certain embodiments, the amount of the initiator in the polymerization reaction mixture for producing a hydrogel carrier or barrier is in the range of 0.001-5% by weight of the polymerization reaction mixture (excluding aqueous solvent and glucose) for producing the hydrogel carrier or barrier. In certain embodiments, the amount of the initiator in the polymerization reaction mixture for producing a hydrogel carrier or barrier is in the range of 0.001 1% by weight of the polymerization reaction mixture (excluding aqueous solvent and glucose) for producing the hydrogel carrier or barrier.

The glucose solution included in the aqueous solvent containing the polymerization reaction mixture for producing a hydrogel carrier or barrier has a concentration in the range of 0.001-909 mg/ml. In certain embodiments, this concentration is in the range of 0.001-200 mg/ml. In certain embodiments, this concentration is in the range of 0.001-100 mg/ml. In certain embodiments, this concentration is in the range of 0.001-50 mg/ml. In certain embodiments, this concentration is in the range of 0.001-5 mg/ml.

In certain embodiments, the hydrogel carrier or barrier includes a polymerization reaction product of one or more than one type of zwitterionic monomer, one or more than one type of saccharide-containing monomers, and one or more than one type of saccharide binding molecule-containing monomers according to aspects of the present disclosure.

The amount of the total of saccharide binding molecule-containing monomers in the polymerization reaction mixture for producing a hydrogel carrier or barrier is in the range of 0.01-95% by weight of the polymerization reaction mixture (excluding aqueous solvent and glucose) for producing the hydrogel carrier or barrier. In certain embodiments, the amount of the total of saccharide binding molecule-containing monomers in the polymerization reaction mixture for producing a hydrogel carrier or barrier is in the range of 0.01-50% by weight of the polymerization reaction mixture (excluding aqueous solvent and glucose) for producing the hydrogel carrier or barrier. In certain embodiments, the amount of the total of saccharide binding molecule-containing monomers in the polymerization reaction mixture for producing a hydrogel carrier or barrier is in the range of 0.01-10% by weight of the polymerization reaction mixture (excluding aqueous solvent and glucose) for producing the hydrogel carrier or barrier. In certain embodiments, the amount of the total of saccharide binding molecule-containing monomers in the polymerization reaction mixture for producing a hydrogel carrier or barrier is in the range of 0.01-5% by weight of the polymerization reaction mixture (excluding aqueous solvent and glucose) for producing the hydrogel carrier or barrier. In certain embodiments, the amount of the total of saccharide binding molecule-containing monomers in the polymerization reaction mixture for producing a hydrogel carrier or barrier is in the range of 0.01-3% by weight of the polymerization reaction mixture (excluding aqueous solvent and glucose) for producing the hydrogel carrier or barrier.

The amount of the total of saccharide-containing monomer in the polymerization reaction mixture for producing a hydrogel carrier or barrier is in the range of 0.001-90% by weight of the polymerization reaction mixture (excluding aqueous solvent and glucose) for producing the hydrogel carrier or barrier. In certain embodiments, the amount of the total of saccharide-containing monomer in the polymerization reaction mixture for producing a hydrogel carrier or barrier is in the range of 0.001-50% by weight of the polymerization reaction mixture (excluding aqueous solvent and glucose) for producing the hydrogel carrier or barrier. In certain embodiments, the amount of the total of saccharide-containing monomer in the polymerization reaction mixture for producing a hydrogel carrier or barrier is in the range of 0.001-10% by weight of the polymerization reaction mixture (excluding aqueous solvent and glucose) for producing the hydrogel carrier or barrier. In certain embodiments, the amount of the total of saccharide-containing monomer in the polymerization reaction mixture for producing a hydrogel carrier or barrier is in the range of 0.001-5% by weight of the polymerization reaction mixture (excluding aqueous solvent and glucose) for producing the hydrogel carrier or barrier. In certain embodiments, the amount of the total of saccharide-containing monomer in the polymerization reaction mixture for producing a hydrogel carrier or barrier is in the range of 0.001-1% by weight of the polymerization reaction mixture (excluding aqueous solvent and glucose) for producing the hydrogel carrier or barrier. In certain embodiments, the amount of the total of saccharide-containing monomer in the polymerization reaction mixture for producing a hydrogel carrier or barrier is in the range of 0.001-0.5% by weight of the polymerization reaction mixture (excluding aqueous solvent and glucose) for producing the hydrogel carrier or barrier.

The amount of the total of zwitterionic monomers in the polymerization reaction mixture for producing a hydrogel carrier or barrier is in the range of 0.1-99% by weight of the polymerization reaction mixture (excluding aqueous solvent and glucose) for producing the hydrogel carrier or barrier. In certain embodiments, the amount of the total of zwitterionic monomers in the polymerization reaction mixture for producing a hydrogel carrier or barrier is in the range of 0.1-98% by weight of the polymerization reaction mixture (excluding aqueous solvent and glucose) for producing the hydrogel carrier or barrier. In certain embodiments, the amount of the total of zwitterionic monomers in the polymerization reaction mixture for producing a hydrogel carrier or barrier is in the range of 0.1-97% by weight of the polymerization reaction mixture (excluding aqueous solvent and glucose) for producing the hydrogel carrier or barrier. In certain embodiments, the amount of the total of zwitterionic monomers in the polymerization reaction mixture for producing a hydrogel carrier or barrier is in the range of 0.1-96% by weight of the polymerization reaction mixture (excluding aqueous solvent and glucose) for producing the hydrogel carrier or barrier. In certain embodiments, the amount of the total of zwitterionic monomers in the polymerization reaction mixture for producing a hydrogel carrier or barrier is in the range of 0.1-95% by weight of the polymerization reaction mixture (excluding aqueous solvent and glucose) for producing the hydrogel carrier or barrier.

The concentration of the total of zwitterionic monomers in the aqueous solvent of the polymerization reaction mixture for producing a hydrogel carrier or barrier is in the range of 0.01-2000 mg/ml. In certain embodiments, this concentration is in the range of 0.01-1000 mg/ml. In certain embodiments this concentration is in the range of 0.01-800 mg/ml. In certain embodiments, this concentration is in the range of 0.01-600 mg/ml. In certain embodiments, this concentration is in the range of 0.01-400 mg/ml. In certain embodiments, this concentration is in the range of 0.01-200 mg/ml.

In one embodiment, the hydrogel carrier or barrier further includes a chemical crosslinker in the reaction mixture. To synthesize the hydrogel carrier or barrier for glucose-responsive release of insulin, or zwitterionic polymer-insulin-saccharide composition according to aspects of the present disclosure, includes a polymerization reaction product of a zwitterionic monomer, a saccharide-containing monomer, and a saccharide binding molecule-containing monomer according to aspects of the present disclosure, in one embodiment, the method includes: forming a reaction mixture containing a zwitterionic monomer, a saccharide-containing monomer, a saccharide binding molecule-containing monomer, a crosslinker and an initiator in an aqueous solvent in presence of glucose, initiating the reaction under conditions that initiate the polymerization of the reaction mixture. The resulting polymer product is dialyzed against an aqueous solvent in presence of glucose and then dialyzed against an aqueous solvent without glucose to obtain the hydrogel carrier or barrier.

The amount of the crosslinker in the reaction mixture for producing a hydrogel carrier or barrier is in the range of 0.001-90% by weight of the reaction mixture (excluding aqueous solvent and glucose) for producing the hydrogel carrier or barrier. In certain embodiments, the amount of the crosslinker in the reaction mixture for producing a hydrogel carrier or barrier is in the range of 0.001-50% by weight of the reaction mixture (excluding aqueous solvent and glucose) for producing the hydrogel carrier or barrier. In certain embodiments, the amount of the crosslinker in the reaction mixture for producing a hydrogel carrier or barrier is in the range of 0.001-10% by weight of the reaction mixture (excluding aqueous solvent and glucose) for producing the hydrogel carrier or barrier. In certain embodiments, the amount of the crosslinker in the reaction mixture for producing a hydrogel carrier or barrier is in the range of 0.001-5% by weight of the reaction mixture (excluding aqueous solvent and glucose) for producing the hydrogel carrier or barrier. In certain embodiments, the amount of the crosslinker in the reaction mixture for producing a hydrogel carrier or barrier is in the range of 0.001-1% by weight of the reaction mixture (excluding aqueous solvent and glucose) for producing the hydrogel carrier or barrier.

In other embodiments, the hydrogel carrier or barrier further comprises a hydrophobic monomer according to the aspects of present disclosure in presence during the reaction to allow for a wide range of hydrophobicity to be achieved by the hydrogel.

In certain embodiments, the hydrophobic monomer is styrene (vinylbenzene).

The amount of the hydrophobic monomer in the reaction mixture for producing a hydrogel carrier or barrier is in the range of 0-90% by weight of the reaction mixture (excluding aqueous solvent and glucose) for producing the hydrogel carrier or barrier. In certain embodiments, the amount of the hydrophobic monomer in the reaction mixture for producing a hydrogel carrier or barrier is in the range of 0-50% by weight of the reaction mixture (excluding aqueous solvent and glucose) for producing the hydrogel carrier or barrier. In certain embodiments, the amount of the hydrophobic monomer in the reaction mixture for producing a hydrogel carrier or barrier is in the range of 0-10% by weight of the reaction mixture (excluding aqueous solvent and glucose) for producing the hydrogel carrier or barrier. In certain embodiments, the amount of the hydrophobic monomer in the reaction mixture for producing a hydrogel carrier or barrier is in the range of 0-1% by weight of the reaction mixture (excluding aqueous solvent and glucose) for producing the hydrogel carrier or barrier. Where the hydrophobic monomer is present, the amount of the hydrophobic monomer in the reaction mixture for producing a hydrogel carrier or barrier is in the range of 0.001-90% by weight of the reaction mixture (excluding aqueous solvent and glucose) for producing the hydrogel carrier or barrier, 0.001-50% by weight of the reaction mixture (excluding aqueous solvent and glucose) for producing the hydrogel carrier or barrier, 0.001-10% by weight of the reaction mixture (excluding aqueous solvent and glucose) for producing the hydrogel carrier or barrier, or 0.001-1% by weight of the reaction mixture (excluding aqueous solvent and glucose) for producing the hydrogel carrier or barrier.

The hydrogel carrier or barrier allows ease of transport of insulin, or a zwitterionic polymer-insulin composition according to the aspects of the present disclosure at relatively high environmental glucose level when saccharide and saccharide binding molecule are not strongly interacting, and slows down or stops the transport of insulin, or a zwitterionic polymer-insulin composition at relatively low environmental glucose level when saccharide binding molecules are strongly bounded.

Provided according to aspects of the present disclosure are novel glucose-responsive zwitterionic polymer-insulin-saccharide compositions and a synthesis protocol to obtain a novel hydrogel carrier or barrier comprising a polymerization reaction product of a zwitterionic CBAA monomer, a mannose-containing monomer, and a ConA-containing monomer, either with or without a MBAA crosslinker, for glucose-responsive release of insulin, or zwitterionic polymer-insulin-saccharide composition according to aspects of the present disclosure, exemplified in Examples herein.

Glucose-responsive zwitterionic polymer-insulin-saccharide compositions are provided according to aspects of the present disclosure which include, in combination, a mannose-selective lectin; and a reaction product of a zwitterionic monomer, an insulin-containing monomer and a mannose-containing monomer.

Optionally, to increase retention of the lectin in the implanted macrogel or administered nano- or microgel particles, a polysaccharide moiety is incorporated in component (A) such as a tri-saccharide, 3,6-di-O-(α-D-mannopyranosyl)-D-mannose. In a further option, component (A) can be a fourth monomer type or even a fifth monomer type that is incorporated to bind the lectin. For example, both of the two mannose containing monomers shown in FIG. 6 can be used simultaneously, or styrene (vinylbenzene) can be further incorporated into component (A) to allow for a wide range of hydrophobicity to be achieved by the macrogel. In addition, a third component (C), e.g., containing PCB and mannose but not insulin, can be used to further enhance the tunability of the macrogel.

A zwitterionic polymer-insulin composition, a zwitterionic polymer-insulin-saccharide composition, a glucose-responsive zwitterionic polymer-insulin-saccharide composition, or a combination of any two or more thereof is provided according to aspects of the present disclosure in the form of a gel. Optionally, the gel is in the form of particles having a particle diameter in the range of 1 nm-50 cm.

The term "macrogel" as used herein refers to a hydrogel encapsulated dosage formulation of a zwitterionic polymer-insulin composition, a zwitterionic polymer-insulin-saccharide composition, a glucose-responsive zwitterionic polymer-insulin-saccharide composition, or a combination of any two or more thereof, wherein the gel formulation has a particle size, diameter or longest dimension in the range of 1 millimeter to 10 centimeters. The term "microgel" as used herein refers to a hydrogel encapsulated dosage formulation of a zwitterionic polymer-insulin composition, a zwitterionic polymer-insulin-saccharide composition, a glucose-responsive zwitterionic polymer-insulin-saccharide composition, or a combination of any two or more thereof, wherein the gel formulation has a particle size in the range of about 1 micron to about 0.99 millimeter. The term "nanogel" as used herein refers to a hydrogel encapsulated dosage formulation of a zwitterionic polymer-insulin composition, a zwitterionic polymer-insulin-saccharide composition, a glu-cose-responsive zwitterionic polymer-insulin-saccharide composition, or a combination of any two or more thereof, wherein the gel formulation has a particle size in the range of about 1 nanometer to about 0.99 micron.

Synthesis of a Glucose-Responsive Zwitterionic PCB-Insulin Macrogel

In this example, synthesis of a zwitterionic PCB-insulin macrogel is described including: (A) zwitterionic PCB polymer with insulin and mannose attached, and (B) Con A (type VI), shown schematically in FIG. 6.

Component (A) is synthesized by random free radical copolymerization of PCB monomer, and monomers with human recombinant insulin and D-mannose as side chains, respectively. This method allows the synthesis of high molecular weight polymers (suitable for later gel formation), enables the composition for PCB, insulin, and mannose to be finely tuned, and does not involve any catalysts. The resulting component (A) polymer-insulin conjugate is purified via dialysis and freeze-dried for further use. The component (A) polymer-insulin conjugate is characterized to determine its MW using MALDI-TOFF MS, and its composition using NMR.

An insulin-containing monomer used in synthesis of Component (A) is produced by reacting insulin molecules with acrylic acid N-hydroxysuccinimide ester in aqueous condition. Resulting insulin monomer is purified through ultrafiltration to remove unreacted acrylic acid N-hydroxysuccinimide ester, and concentrated to desired concentration for polymerization.

Optionally, a zwitterionic PCB-insulin macrogel according to aspects of the present disclosure includes a polymer-insulin leachable, lectin non-leachable implantable formulation. In this example, this type of formulation is achieved by producing monomers with Con A as side chains, for example by following a synthetic method similar to that described for synthesis of the insulin monomer. Con A monomer is polymerized with zwitterionic monomers, such as CBAA and MBAA crosslinker to form a non-leaching matrix either before or after the mixing with Component A.

Optionally, a matrix can be made into porous structures, e.g., via a microtemplating method. The Component A loading process can also be optimized by controlling the environmental glucose concentration: at high glucose level, Component A diffusion to the inner part of the implant can be facilitated (Component A binding to Con A is weakened); at low glucose level, Component A can be stably retained by and loaded into the matrix (Component A binding to Con A is highly strengthened).

In this example, the α-configuration of mannopyranoside is used in the mannose monomer since it is the preferred configuration for Con A binding. Specifically, one type of mannose containing monomer is prepared by reacting 4-aminophenyl α-D-mannopyranoside (NH2-Mannose, commercially available from Sigma) with acryloyl chloride in anhydrate organic solvent such as dimethylformamide, and purified through ether precipitation and solvent evaporation.

According to this mannose monomer synthesis, $NH_2$ groups but not OH groups of the mannopyranoside react with acryloyl chloride, with resulting mannose moieties maintaining strong Con A binding capability. The resulting mannose containing monomer has a benzene group between the mannose group and polymerizable double bond (the first structure of mannose monomer in FIG. 6).

Alternatively, a second type of mannose containing monomer, the second mannose-containing structure in FIG. 6, can be prepared by reacting 1-C-(2-hydroxyethyl)-2,3,4, 6-tetra-O-triethylsilyl α-D-mannopyranoside (a triethylsilyl (TES) protected mannopyranoside alcohol) with acryloyl chloride, followed by trifluoroacetic acid treatment to remove TES protecting groups. The TES protected mannopyranoside alcohol can be synthesized from α-D-mannose pentaacetate (commercially available from Sigma) based on methods described in Mortell, K. H. et al., JACS, 1994. 116(26):12053-12054; and Joralemon, M. J. et al., Biomacromolecules, 2004. 5(3):903-913. The presence of benzene structure using this mannose-containing monomer is expected to increase the overall hydrophobicity and strengthen the gel integrity.

A glucose-responsive zwitterionic PCB-insulin macrogel according to aspects of the present disclosure is obtained by physically mixing component (A) and (B).

Particle size can be achieved by physical or chemical methodology. Physical treatment of a gel mass of any shape can be used to achieve smaller particles. Examples of physical treatments to achieve a population of particles of a desired average particle size include filtration, sedimentation, crushing, cutting and micronization.

Examples of chemical treatments to achieve a population of particles of a desired average particle size include use of one or more surfactants in the process of synthesis of a zwitterionic polymer-insulin composition, a zwitterionic polymer-insulin-saccharide composition, a glucose-responsive zwitterionic polymer-insulin-saccharide composition, or a combination of any two or more thereof in the form of a gel. An included surfactant can be a single surfactant, a blend of surfactants, or a surfactant composition including a surfactant, a polymer such as guar gum or a cellulosic derived polymer, diluents such as water or glycols, or other additives. Surfactants employable in this regard include, but are not limited to cationic or quaternary surfactants, non-ionic surfactants, zwitterionic (amphoteric) surfactants, anionic surfactants, and all known surfactants in the industry including silicone surfactants, polymeric surfactants, and fluoral surfactants.

Specific examples of the surfactants include: sodium dodecyl sulfate, polysorbate, di-tallow dimethyl quaternary surfactants, preferably di-tallow dimethyl chloride, $C_{16}$-$C_{22}$ amine ethoxylate with 2EO and its oxide and betaine, $C_{16}$-$C_{22}$ amine ethoxylate quaternary with 2 EO, $C_{12}$-$C_{22}$ dimethylaminopropyl amine and its oxide and betaine, $C_{12}$-$C_{18}$ dimethyl amine oxide, $C_{12}$-$C_{18}$ dimethyl betaine, and $C_{12}$-$C_{18}$ amidoamine ethoxylate derived from DETA (diethylenetriamine) and its oxide and betaine; preferably the hydrocarbon chains derived from coco, tallow, soy, corn, castor, coconut, palm, canola, lard, peanut, or tall oil fatty acid.

Further examples of surfactants are fatty acid soaps such as sodium laurate, sodium myristate, sodium palmitate, soaps from fatty acids of tall oil or mixtures thereof; alkali metal sulfates derived from fatty alcohol containing at least 10 carbon atoms such as sodium lauryl sulfate, potassium myristyl sulfate, and the like; alkali metal sulfonates derived from aryl sulfonic acids such as sodium naphthalene sulfonate, sodium isopropyl naphthalene sulfonate, sodium di-isobutyl naphthalene sulfonate, sodium lauryl benzene sulfonate, and the like; salts of high molecular weight organic bases such as cetyl trimethyl ammonium sulfate and the like.

Glucose-responsive zwitterionic polymer-insulin-saccharide compositions are provided according to aspects of the present disclosure wherein the ratio of the mannose-selective lectin:the reaction product of a zwitterionic monomer, an insulin-containing monomer and a mannose containing monomer is in the range of 0.001:1-1:0.001.

A zwitterionic polymer-insulin composition, a zwitterionic polymer-insulin-saccharide composition, a glucose-responsive zwitterionic polymer-insulin-saccharide composition, or a combination of any two or more thereof are provided according to aspects of the present disclosure which further include a pharmaceutically acceptable carrier.

The term "pharmaceutically acceptable carrier" refers to a carrier which is substantially non-toxic to a subject to which the composition is administered and which is substantially chemically inert with respect to the active component or components.

A pharmaceutical composition according to the disclosure generally includes about 0.1-99% of free or polymer-conjugated insulin.

Pharmaceutical compositions suitable for delivery to a subject may be prepared in various forms illustratively including physiologically acceptable sterile aqueous or nonaqueous dispersions, suspensions or emulsions, and sterile powders for reconstitution into sterile injectable dispersions, suspensions or emulsions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyl oleate. Additional components illustratively including a buffer, a solvent, or a diluent may be included.

Such formulations are administered by a suitable route including parenteral and oral administration. Administration may include systemic or local injection, and particularly subcutaneous injection. Administration is preferably by subcutaneous implantation for macrogel compositions.

Pharmaceutical compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature.

Solid dosage forms for oral administration include capsules, tablets, pills, powders, and granules. In such solid dosage forms, a zwitterionic polymer-insulin composition, a zwitterionic polymer-insulin-saccharide composition, a glucose-responsive zwitterionic polymer-insulin-saccharide composition, or a combination of any two or more thereof described herein is admixed with at least one inert customary excipient (or carrier) such as sodium citrate or dicalcium phosphate or (a) fillers or extenders, as for example, starches, lactose, sucrose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to a zwitterionic polymer-insulin composition, a zwitterionic polymer-insulin-saccharide composition, a glucose-responsive zwitterionic polymer-insulin-saccharide composition, or a combination of any two or more thereof, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

Pharmaceutically acceptable carriers and formulation of pharmaceutical compositions are known in the art, illustratively including, but not limited to, as described in Remington: The Science and Practice of Pharmacy, 21st Ed., Lippincott, Williams & Wilkins, Philadelphia, PA, 2006; and Allen, L. V. et al., Ansel's Pharmaceutical Dosage Forms and Drug Delivery Systems, 8th Ed., Lippincott, Williams & Wilkins, Philadelphia, PA, 2005.

Methods of treatment of a subject in need of insulin are provided according to aspects of the present disclosure which include administering a zwitterionic polymer-insulin composition, a zwitterionic polymer-insulin-saccharide composition, a glucose-responsive zwitterionic polymer-insulin-saccharide composition, or a combination of any two or more thereof.

Figure 7:
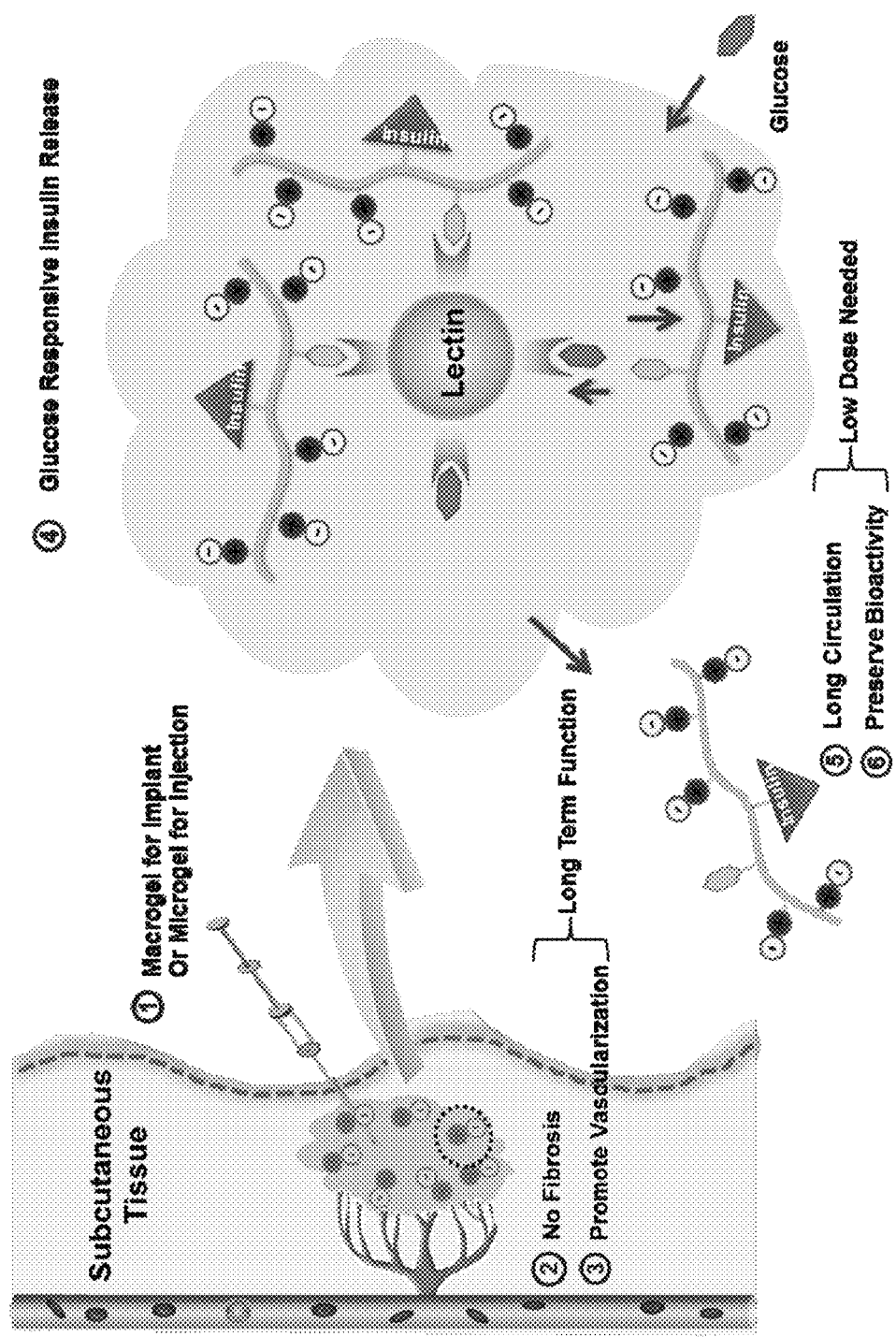
FIG. 7 is a schematic diagram showing a subcutaneous implant or injection of a glucose-responsive zwitterionic polymer-insulin-saccharide composition in gel form.
Figure 8A:
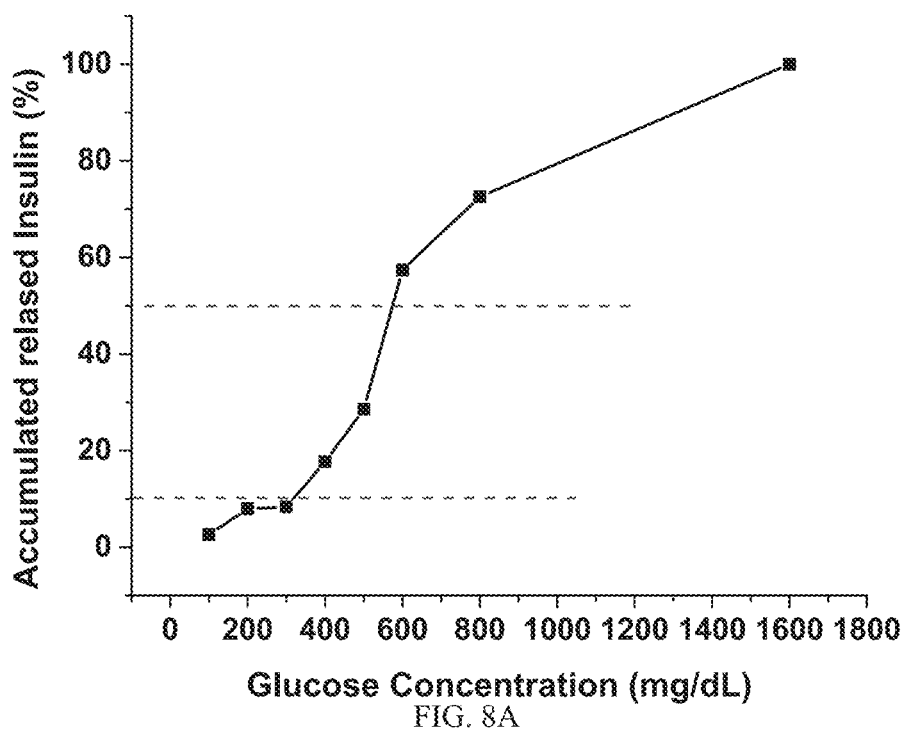
FIG. 8A is a graph showing a set-point curve of the glucose-responsive zwitterionic PCB-insulin macrogel and comparison with preferred standards.
Figure 8B:
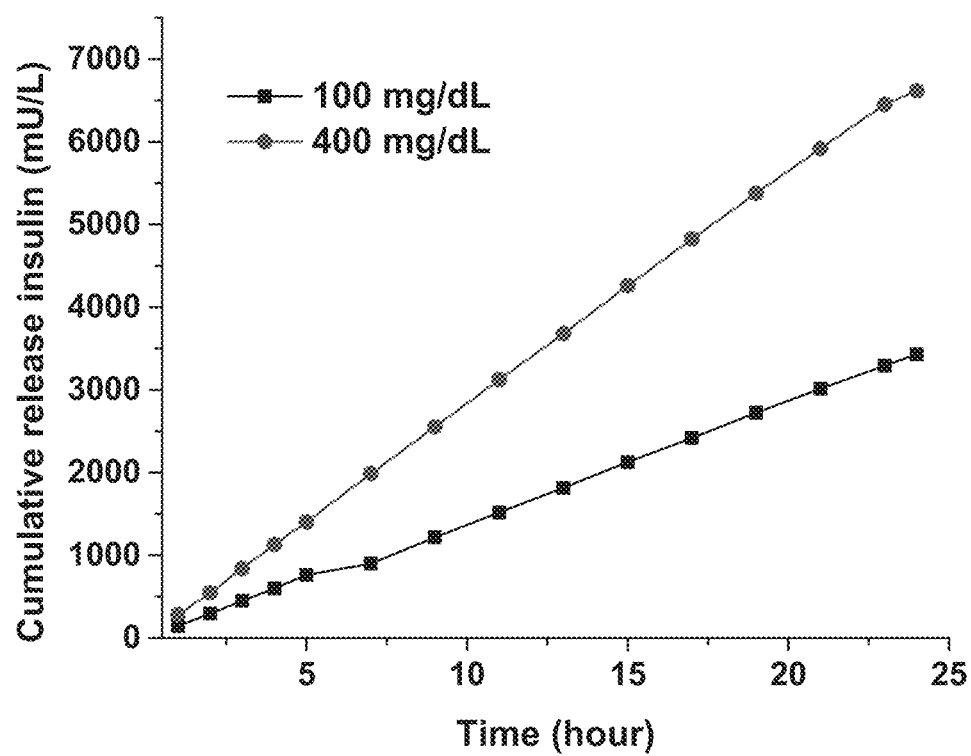
FIG. 8B is a graph showing insulin release kinetics of the glucose-responsive zwitterionic PCB-insulin macrogel during incubation in 100 mg/dl or 400 mg/dl.
Figure 8C:
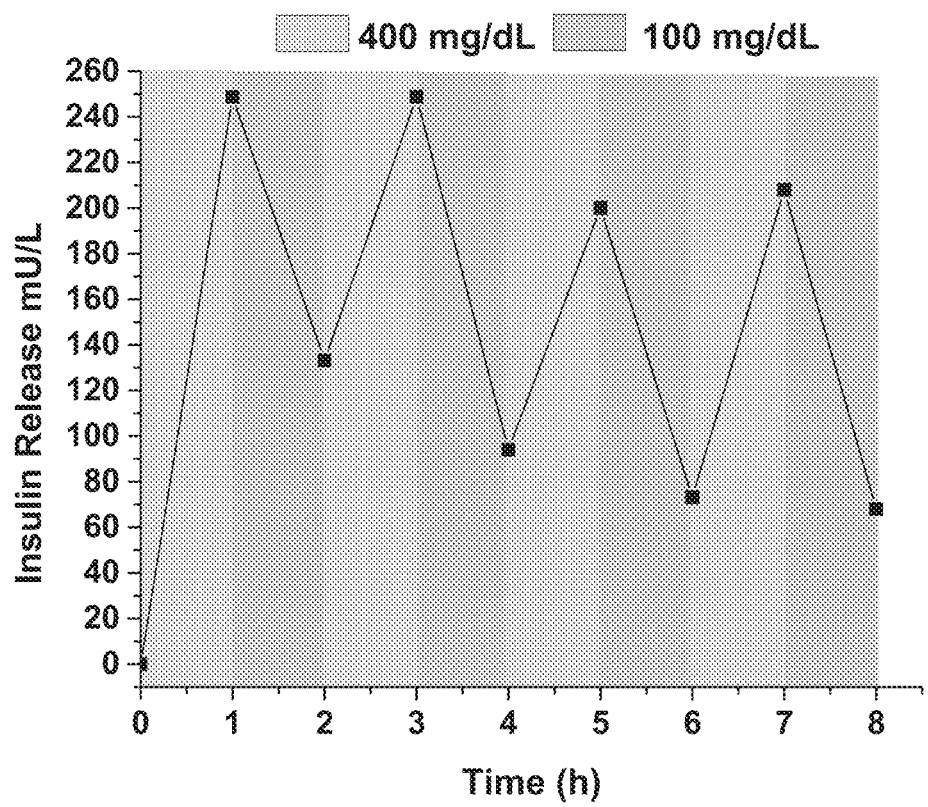
FIG. 8C is a graph showing results of a cycling test of the glucose-responsive zwitterionic PCB-insulin macrogel with repeatedly changed glucose concentration.

FIG. 7 is a schematic illustration showing a subcutaneous implant or injection of a glucose-responsive zwitterionic polymer-insulin-saccharide composition in gel form.

Methods and compositions of the present disclosure can be used for prophylaxis as well as amelioration of signs and/or symptoms of type 1 diabetes, type 2 diabetes, gestational diabetes or pre-diabetes. The terms "treating" and "treatment" used to refer to treatment of type 1 diabetes, type 2 diabetes, gestational diabetes or pre-diabetes in a subject include: preventing, inhibiting or ameliorating the type 1 diabetes, type 2 diabetes, gestational diabetes or pre-diabetes in the subject, such as slowing progression of the diabetes or pre-diabetes and/or reducing or ameliorating a sign or symptom of the type 1 diabetes, type 2 diabetes, gestational diabetes or pre-diabetes.

A therapeutically effective amount of a zwitterionic polymer-insulin composition, a zwitterionic polymer-insulin-saccharide composition, a glucose-responsive zwitterionic polymer-insulin-saccharide composition, or a combination of any two or more thereof administered according to aspects of the present disclosure is an amount which has a beneficial effect in a subject being treated. In subjects having type 1 diabetes, type 2 diabetes, gestational diabetes or pre-diabetes, or other condition responsive to treatment with insulin, a therapeutically effective amount of a zwitterionic polymer-insulin composition, a zwitterionic polymer-insulin-saccharide composition, a glucose-responsive zwitterionic polymer-insulin-saccharide composition, or a combination of any two or more thereof is effective to ameliorate or prevent one or more signs and/or symptoms of the type 1 diabetes, type 2 diabetes, gestational diabetes or pre-diabetes or other condition responsive to treatment with insulin.

Subjects are identified as having, or at risk of having, type 1 diabetes, type 2 diabetes, gestational diabetes or pre-diabetes or other condition responsive to treatment with insulin using well-known medical and diagnostic techniques. In particular aspects of the present disclosure, a treated subject is an individual known to have type 1 diabetes, suspected of having type 1 diabetes or at risk of having type 1 diabetes.

The term "subject" refers to an individual in need of treatment for a pathological condition responsive to the beneficial effects of compositions of the present disclosure, particularly type 1 diabetes, type 2 diabetes, gestational diabetes or pre-diabetes. While the present disclosure describes compositions and methods for treatment of human subjects in need thereof, the present disclosure is not limited to human subjects and the term subject generally includes mammals, birds and fish, such as, but not limited to, non-human primates, cats, dogs, cows, horses, rodents, pigs, sheep, goats, poultry and fish. Subjects can be either gender and can be any age.

A zwitterionic polymer-insulin composition, a zwitterionic polymer-insulin-saccharide composition, a glucose-responsive zwitterionic polymer-insulin-saccharide composition, or a combination of any two or more thereof of the present disclosure is injected intravenously and/or implanted subcutaneously according to aspects of the present disclosure.

A zwitterionic polymer-insulin composition, a zwitterionic polymer-insulin-saccharide composition, a glucose-responsive zwitterionic polymer-insulin-saccharide composition, or a combination of any two or more thereof is administered to a subject by any of a variety of systemic and/or local routes according to aspects of methods of the present disclosure including, but not limited to, intravenous, intramuscular, subcutaneous, intraperitoneal, oral, otic, rectal, vaginal, topical, parenteral, pulmonary, ocular, nasal, intratumoral and mucosal.

A zwitterionic polymer-insulin composition, a zwitterionic polymer-insulin-saccharide composition, a glucose-responsive zwitterionic polymer-insulin-saccharide composition, or a combination of any two or more thereof may be administered acutely or chronically according to aspects of methods of the present disclosure.

A zwitterionic polymer-insulin composition, a zwitterionic polymer-insulin-saccharide composition, a glucose-responsive zwitterionic polymer-insulin-saccharide composition, or a combination of any two or more thereof may be administered as a unitary dose or in multiple doses over a relatively limited period of time, such as seconds-hours. Administration may include multiple doses of a zwitterionic polymer-insulin composition, a zwitterionic polymer-insulin-saccharide composition, a glucose-responsive zwitterionic polymer-insulin-saccharide composition, or a combination of any two or more thereof of the present disclosure administered over a period of days-years, such as for chronic treatment of type 1 diabetes, type 2 diabetes, gestational diabetes or pre-diabetes.

A therapeutically effective amount of a zwitterionic polymer-insulin composition, a zwitterionic polymer-insulin-saccharide composition, a glucose-responsive zwitterionic polymer-insulin-saccharide composition, or a combination of any two or more thereof according to the present disclosure will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

Combination Treatments

Combinations of therapeutic agents are administered according to aspects of the present disclosure. In some aspects, a zwitterionic polymer-insulin composition, a zwitterionic polymer-insulin-saccharide composition, a glucose-responsive zwitterionic polymer-insulin-saccharide composition, or a combination of any two or more thereof of the present disclosure and at least one additional therapeutic agent is administered to a subject to treat type 1 diabetes, type 2 diabetes, gestational diabetes or pre-diabetes in a subject in need thereof. In still further aspects, a zwitterionic polymer-insulin composition, a zwitterionic polymer-insulin-saccharide composition, a glucose-responsive zwitterionic polymer-insulin-saccharide composition, or a combination of any two or more thereof of the present disclosure and at least two additional therapeutic agents are administered to a subject to treat type 1 diabetes, type 2 diabetes, gestational diabetes or pre-diabetes in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present disclosure include one or more anti-diabetic drugs such as, but are not limited to, acarbose, biguanides such as metformin, butformin and phenformin; sulfonylureas such as acetohexamide, chlorpropamide, tolazamide, tolbutamide, glyburide, gliquidone, gliclazide, glipizide and glimepiride; meglitinides such as repaglinide and nateglinide; thiazolidinediones such as rosiglitazone, englitazone, lobeglitazone and pioglitazone; DPP-4 inhibitors such as sitagliptin, saxagliptin and linagliptin; meglitinides such as nateglinide and repaglinide; GLP-1 receptor agonists such as exenatide and liraglutide; SGLT2 inhibitors such as canagliflozin and dapagliflozin; insulin and insulin analogs such as insulin glulisine, insulin lispro, insulin aspart, insulin glargine, insulin detemir, and insulin isophane.

Additional therapeutic agents included in aspects of methods and compositions of the present disclosure include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Combination therapies utilizing a zwitterionic polymer-insulin composition, a zwitterionic polymer-insulin-saccharide composition, a glucose-responsive zwitterionic polymer-insulin-saccharide composition, or a combination of any two or more thereof of the present disclosure and one or more additional therapeutic agents may show synergistic effects.

Medical devices including a zwitterionic polymer-insulin composition, a zwitterionic polymer-insulin-saccharide composition, a glucose-responsive zwitterionic polymer-insulin-saccharide composition, or a combination of any two or more thereof in gel form are provided according to aspects of the present disclosure.

Such medical devices include, for example, an implantable sensor, an implantable prosthesis such as an artificial joint, breast implant, cochlear implant, dental implant or removable apparatus, contact lens, prosthetic eye, artificial heart valve, artificial blood vessel, pacemaker, left ventricular assist device, blood vessel graft, such as an artery graft, stent, tubing such as a urinary catheter, drainage tube, endotracheal tube, instrument guidance tube, feeding tube, shunt, bone repair implant, suture material, membranes, particles, films, tissues and pads.

An element of a medical device is optionally coated, partially or completely, with a zwitterionic polymer-insulin composition, a zwitterionic polymer-insulin-saccharide composition, a glucose-responsive zwitterionic polymer-insulin-saccharide composition, or a combination of any two or more thereof in gel form wherein the element is a surface of the device, a component of the device or any portion thereof. An entire device may be coated or impregnated with a zwitterionic polymer-insulin composition, a zwitterionic polymer-insulin-saccharide composition, a glucose-responsive zwitterionic polymer-insulin-saccharide composition, or a combination of any two or more thereof in gel form according to aspects of the present disclosure.

Embodiments of inventive compositions and methods are illustrated in the following examples. These examples are provided for illustrative purposes and are not considered limitations on the scope of inventive compositions and methods.

Polymerization Reactions

Methods of polymerizing reaction components having reactive groups to produce a polymerization product include radical polymerization, living polymerization, condensation, ring opening polymerization and click chemistry. Details of polymerization mechanisms are weft-known along with appropriate reaction conditions, initiators, catalysts and other standard co-factors as exemplified herein.

Zwitterionic monomers containing carboxybetaine and sulfobetaine can be synthesized by using a tertiary amine containing acrylate, acrylamide, or vinyl monomer to react with lactone or sultone, or to react with alkyl halides containing acid groups, or to react with alkyl halides containing acid esters followed by removal acid ester to give acid groups.

Zwitterionic copolymers with reactive double bond groups are synthesized through free radical random polymerization of zwitterionic monomer ester precursors (e.g., CBAA-tBu monomer) and functionalizable monomers such as amine containing monomers (e.g., aminoethyl methacrylate hydrochloride) initiated by an initiator at heating, or lighting conditions. The obtained copolymer has the functionalizable repeating unit that is further reacted to introduce a double bond into the copolymer, e.g., by reacting the amine group of aminoethyl methacrylate with acryloylchloride. The resulting product is subjected to trifluoroacetic acid treatment to remove the ester groups of zwitterionic monomer precursors (e.g., t-Bu ester groups) to re-generate the zwitterionic repeating units. The ratios of monomers/initiators and zwitterionic precursor monomers/functionalizable monomers are varied to obtain copolymers with different MWs and with different amounts of double bond groups attached to the copolymer chain. The obtained zwitterionic copolymers containing reactive double bond groups are purified through precipitation in ethyl ether and vacuum-dried before use.

Zwitterionic polymers are synthesized through free radical polymerization method or living polymerization method. These polymerization methods normally involve initiators, zwitterionic monomers, catalysts (optional), and the polymerization condition is selected from heating, lighting, etc. The feeding monomer amount relative to initiator amount is varied to obtain polymers with different molecular weight (MW). The obtained polymers are typically purified by dialyzing against water followed by freeze-drying.

Methods are provided according to aspects of the present disclosure which include a method for modifying insulin to improve its pharmacokinetics and its bioactivity, including (1) reacting a (poly)carboxybetaine polymer, (poly)sulfobetaine polymer or (poly)phosphobetaine polymer with insulin under reaction conditions so that acylation occurs primarily on LysB29 and less acylation occurs on GlyA1 and PheB1 of the insulin protein, forming a (poly)carboxybetaine polymer-insulin conjugate, (poly)sulfobetaine polymer-insulin conjugate or (poly)phosphobetaine polymer-insulin conjugate reaction product which has biological activity similar to or better than unconjugated insulin. The (poly)carboxybetaine polymer, (poly)sulfobetaine polymer or (poly)phosphobetaine polymer includes reactive groups that react with primary amines of insulin. The (poly)carboxybetaine polymer-insulin conjugate, (poly)sulfobetaine polymer-insulin conjugate or (poly)phosphobetaine polymer-insulin conjugate reaction product includes one or more isoforms and one or all of the isoforms is optionally purified from other isoforms. In a further option, one or more isoforms of the (poly)carboxybetaine polymer-insulin conjugate, (poly)sulfobetaine polymer-insulin conjugate or (poly)phosphobetaine polymer-insulin conjugate reaction product is purified to remove unconjugated, free insulin protein from the reaction product. In a further option, one or more isoforms of the (poly)carboxybetaine polymer-insulin conjugate, (poly)sulfobetaine polymer-insulin conjugate or (poly)phosphobetaine polymer-insulin conjugate reaction product is purified to remove unconjugated, free (poly)carboxybetaine, (poly)sulfobetaine or (poly)phosphobetaine from the reaction product.

Reaction conditions so that acylation occurs primarily on LysB29 and less acylation occurs on GlyA1 and PheB1 of insulin include, for example, pH conditions and ratio of polymer:insulin reactants.

Thus, pH near or exceeding the pka of epsilon amine of LysB29 will result in majority of polymers conjugated to B29, that is, about pH 10 or above.

Non-limiting examples of such reaction conditions operative with any of the "reactive groups that react with primary amines of insulin" include reaction in 0.1M Na2CO3; or water/MeCN, pH 10; or DMSO/TEA.

The ratio of polymer:insulin in a conjugation reaction to produce zwitterionic polymer-insulin conjugates wherein at least 50% of the zwitterionic polymer-insulin conjugates comprise zwitterionic polymer conjugated to insulin at least at LysB29 is 1:1 or greater, such as 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, 100:1, 200:1, 300:1, 400:1, 500:1, 600:1, 700:1, 800:1, 900:1, 1000:1 or greater.

Methods are provided according to aspects of the present disclosure which include a method for modifying insulin to improve its pharmacokinetics and its bioactivity, including (1) reacting a (poly)carboxybetaine polymer, (poly)sulfobetaine polymer or (poly)phosphobetaine polymer with insulin under reaction conditions so that acylation occurs primarily on LysB29 and less acylation occurs on GlyA1 and PheB1 of the insulin protein, wherein the one or more primary amines of insulin are selected from a group consisting of GlyA1, PheB1 and LysB29, forming a (poly)carboxybetaine polymer-insulin conjugate, (poly)sulfobetaine polymer-insulin conjugate or (poly)phosphobetaine polymer-insulin conjugate reaction product which has biological activity similar to or better than unconjugated insulin. The (poly)carboxybetaine polymer, (poly)sulfobetaine polymer or (poly)phosphobetaine polymer includes reactive groups that react with primary amines of insulin. The (poly)carboxybetaine polymer-insulin conjugate, (poly)sulfobetaine polymer-insulin conjugate or (poly)phosphobetaine polymer-insulin conjugate reaction product includes one or more isoforms and one or all of the isoforms is optionally purified from other isoforms. In a further option, one or more isoforms of the (poly)carboxybetaine polymer-insulin conjugate, (poly)sulfobetaine polymer-insulin conjugate or (poly)phosphobetaine polymer-insulin conjugate reaction product is purified to remove unconjugated, free insulin protein from the reaction product. In a further option, one or more isoforms of the (poly)carboxybetaine polymer-insulin conjugate, (poly)sulfobetaine polymer-insulin conjugate or (poly)phosphobetaine polymer-insulin conjugate reaction product is purified to remove unconjugated, free (poly)carboxybetaine, (poly)sulfobetaine or (poly)phosphobetaine from the reaction product.

Embodiments of inventive compositions and methods are illustrated in the following examples. These examples are provided for illustrative purposes and are not considered limitations on the scope of inventive compositions and methods.

EXAMPLES

Example 1

Materials

Human recombinant insulin was purchased from Life Technologies Corporation. Methoxypolyethylene glycol 5000 Da acetic acid N-succinimidyl ester (PEG-NETS) and streptozotocin (STZ) were purchased from Sigma-Aldrich. HEPES buffer were purchased from Hyclone.

Synthesis of Conjugates of PCB-Insulin and PEG-Insulin

1) Synthesis of PCB-(N-hydroxysuccinimide) (NETS)

NHS-PCB-tBu was synthesized by atom transfer radical polymerization (ATRP) of 2-tert-butoxy-N-(2-(methacryloyloxy)ethyl)-N,N-dimethyl-2-oxoethanaminium (CB-tBu), which was carried out in anhydrous dimethylformamide (DMF), initiated by N-hydroxysuccinimide 2-bromopropanoate, and catalyzed by Cu(I)Br/1,1,4,7,10,10-hexamethyltriethylenetetramine (HMTETA). The resulting NHS-PCB-tBu was purified through precipitation in acetone, and later treated with trifluoroacetic acid to obtain PCB-NHS, which was further precipitated in ethyl ether, and dried under vacuum condition.

2) Synthesis of Conjugates of PCB-Insulin and PEG-Insulin

Conjugates of PCB-insulin and PEG-insulin were synthesized by reacting NETS ester groups of the polymer with available amine groups on the protein. Typically, insulin (1 mg/mL) was dissolved in 0.1 M $Na_2CO_3$ buffer. To obtain free insulin, PCB-insulin and PEG-insulin rough products (without purification) having the same molar content, the insulin stock solution was homogeneously divided into three portions, with one used without modification as free insulin, and the other two portions used for conjugation with PCB and PEG, respectively. For the conjugation reaction, pre-dissolved PCB-(N-succinimidyl ester) 5,000 (PCB-NHS 5K) or methoxypolyethylene glycol 5,000 Da acetic acid N-succinimidyl ester (PEG-NETS 5K) was added into the insulin solution at a polymer:insulin molar ratio of 1.2:1, and the reaction mixture was stirred at a rate of 700 r/min, 0° C., for one hour to obtain the PCB-insulin or PEG-insulin rough products. After reaction, the buffer was adjusted to pH 7.4 using HCl. To obtain PEG-insulin and PCB-insulin where most of the three amines of insulin (GlyA1, PheB1, and LysB29) were conjugated with PEG or PCB, pre-dissolved PCB-NHS 5K or PEG-NETS 5K was added into the insulin solution at a polymer:insulin molar ratio of 20:1 in 0.2 M HEPES buffer, and the reaction mixture was stirred at a rate of 400 r/min for 40 hours.

3) Purification of PCB-Insulin and PEG-Insulin

To purify PCB-insulin and PEG-insulin, the rough products were placed in a dialysis kit (6-8 kDa MWCO, Sigma-Aldrich). The MW cut off retains the polymer-insulin conjugates, but allows both free insulin and unconjugated PCB-NHS or PEG-NETS to go through. It was monitored whether or not there was unconjugated insulin or polymer partitioned to the solvent phase outside of the dialysis tubing after each dialysate buffer refreshment—a criterion to determine the completion of purification. Unconjugated insulin can be detected using UV-vis spectrometer (at 276 nm). Also both unconjugated insulin and polymer can be sensitively detected by dynamic light scattering (DLS) (Zetasizer Nano-ZS, Malvern); a dialysate solution with the count rate (the number of photons detected per second) as low as that of pure water indicating that the solution is essentially free of insulin or polymer. The purified polymer-insulin samples were desalted using a PD-1 column and freeze-dried for storage. To quantify the molar concentration of purified PCB-insulin and PEG-insulin solution sample, both methods of UV-vis absorbance (276 nm), and a commercially available human insulin ELISA assay kit (Mercodia, Uppsala, SE) were used.

Matrix-assisted laser desorption/ionization time-of-flight mass spectrometry (MALDI-TOF MS)

The samples of free insulin, PEG-insulin and PCB-insulin were dissolved in 0.2M HEPES buffer and analyzed on an Autoflex III matrix assisted laser desorption/ionization time-of-flight mass spectrometry (MALDI-TOF-MS, Bruker Daltonics). The mass spectra were collected with repetition rate of 100 Hz, accelerating voltage of 19 kV and an average of 700 shots. The data was analyzed with Biotools program (Bruker).

Circular Dichroism (CD)

CD spectra were collected by using a Chirascan spectrophotometer from Applied Photophysics at 25° C. Insulin samples were dissolved in 0.2 M PBS buffer at 0.2 mg/ml. The near-UV CD spectra were measured from 200 to 250 nm with the light-path length of 1 mm. The scanning speed of CD spectra measurement was set at 200 nm/min. Each spectrum was the average of three scans to increase the signal-to-noise ratio of the measurements. The secondary structure proportions for insulin and its conjugates were analyzed using CDSSTR software.

Dynamic Light Scattering (DLS)

The hydrodynamic sizes of the insulin and its conjugate samples were collected by a DLS method using a Malvern Nano-ZS Zetasizer at 25° C.

In Vitro Bioactivity Assay of Insulin

About 25,000 CHO-M1 cells/well (ATCC) were seeded in a 96-well tissue culture treated plate and incubate for 24 h before being cultured in serum-free medium. These cells were then treated with 10 μg/mL native insulin, PEG-insulin, and PCB-insulin samples, respectively, for 45 minutes. Then cells were lysed and a commercially available kit (Cisbio) was used to assay phosphorylated AKT at Ser473. The fluorescence emission at 665 and 620 nm was measured on a HTRF reader (BioTek, USA).

Animal Experiments

To establish streptozotocin (STZ)-induced diabetic mice model, healthy mice (C57BL/6J, male, 6-8 weeks of age, Jackson Lab) received a daily i.p. injection of 5 mg/ml STZ at 50 mg/kg for 5 consecutive days. 17 days after the first injection, body weight and blood glucose were measured to confirm the diabetic status. Only mice whose nonfasted blood glucose levels were above 300 mg/dL for two consecutive days were considered diabetic for further in vivo testing. To examine the blood glucose lowering effect of insulin and its conjugate samples, diabetic mice received tail vein injection of 10 nmol/kg of free insulin, rough products and purified forms of PCB-insulin and PEG-insulin, respectively (mouse group size was 6). 5-10 μL blood samples were collected from the tail for glucose testing using a clarity plus blood-glucose meter at predetermined time intervals. The mice were fasted during the glucose testing period. To examine the blood concentration of injected insulin, 10 nmol/kg of free insulin, purified PCB-insulin and PEG-insulin were injected through the tail vein (mouse group size was 6). At predetermined time intervals, 25 μL blood samples were collected from the tail vein. The insulin concentration in the blood serum was determined using a Mercodia human insulin ELISA assay. The mice were fasted during the blood insulin testing period.

Synthesis of PCB-Insulin Conjugate

NHS ester terminated PCB (PCB-NHS) was synthesized as described in Cao Z Q et al., Langmuir, 2012; 28:11625-11632. The MW for PCB-NHS was ~5000 Da: MW=4887D determined by $^1$H NMR, Mn=5410 D, polydispersity=1.03 characterized by GPC. Then PCB-NHS was reacted with the amine group of insulin at PCB-NHS: the insulin molar ratio was of 1.2 to 1 to synthesize PCB-insulin conjugate. The reaction was conducted at $Na_2CO_3$ solution (pH>10), at which condition the acylation is at any of the three amines (GlyA1, PheB1, or LysB29), but prioritized at epsilon amine of LysB29.

For comparison, PEG-insulin was obtained by reacting a commercially available PEG-NHS (5000 Da, MW) with human recombinant insulin, using a similar method.

Figure 2:
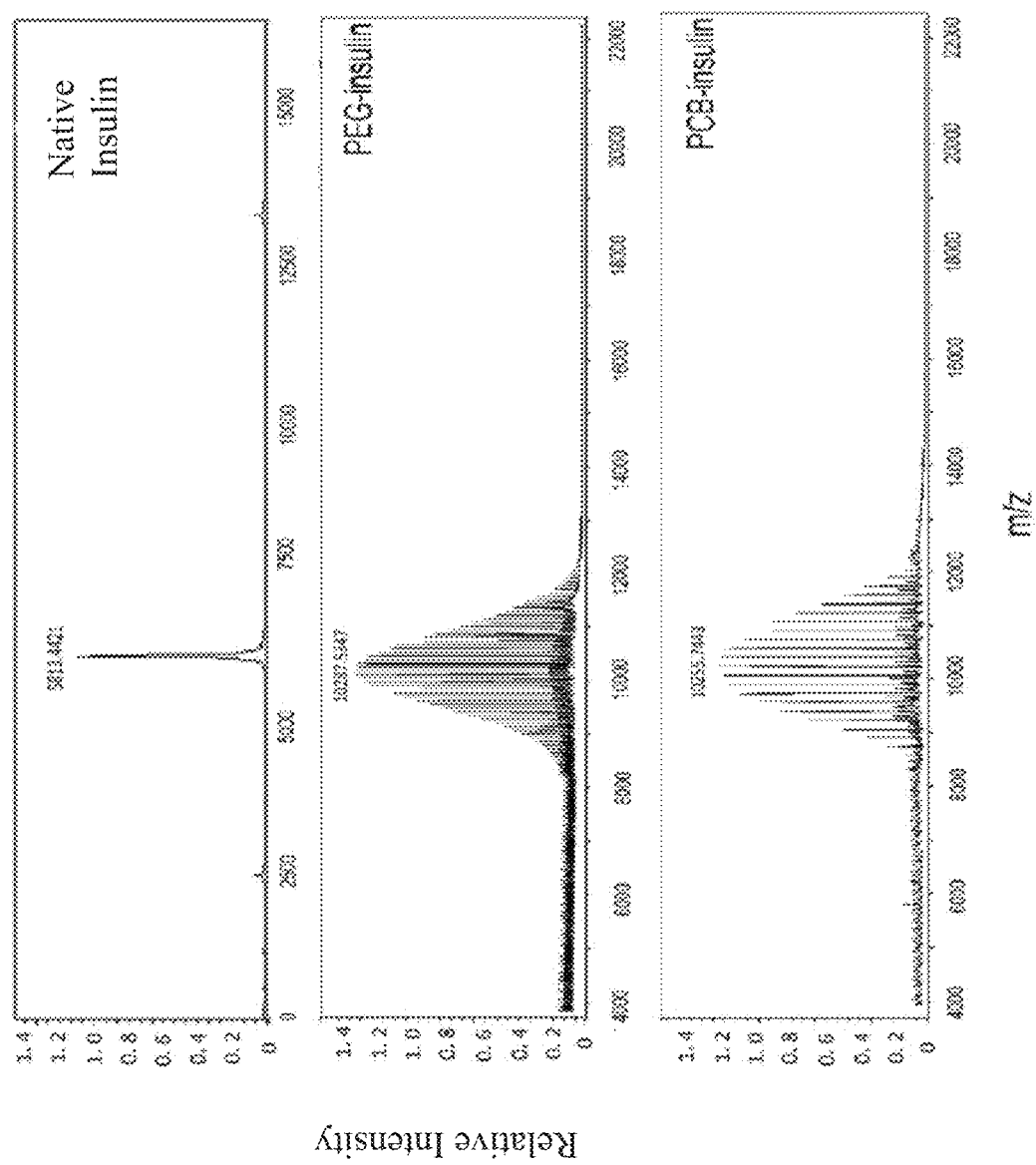
FIG. 2 is a graph showing results of MALDI-TOF MS analysis of purified PCB-insulin conjugate and purified PEG-insulin conjugate compared to free insulin.

The synthesized PCB-insulin conjugates and PEG-insulin conjugates were purified using a 6-8 kDa MWCO dialysis kit to remove unreacted insulin (~5800 Da) and un-conjugated PCB-NHS or PEG-NHS (about 5000 Da). The purified PCB-insulin and PEG-insulin were analyzed by MALDI-TOF MS, and their purity was confirmed by the disappearance of free insulin peak (m/z=5813.44 Da) as shown in FIG. 2.

Based on MALDI-TOF results (FIG. 2), the major products for both PCB-insulin and PEG-insulin have one-polymer-chain modification per protein: only one peak was shown corresponding to insulin with one polymer chain conjugated. The obtained PCB-insulin and PEG-insulin were not further separated to obtain their respective purified isoforms (i.e., a polymer conjugated to LysB29 of insulin) before evaluating their PK and bioactivity.

Secondary Structure of PCB-Insulin

Figures 3A, 3B:
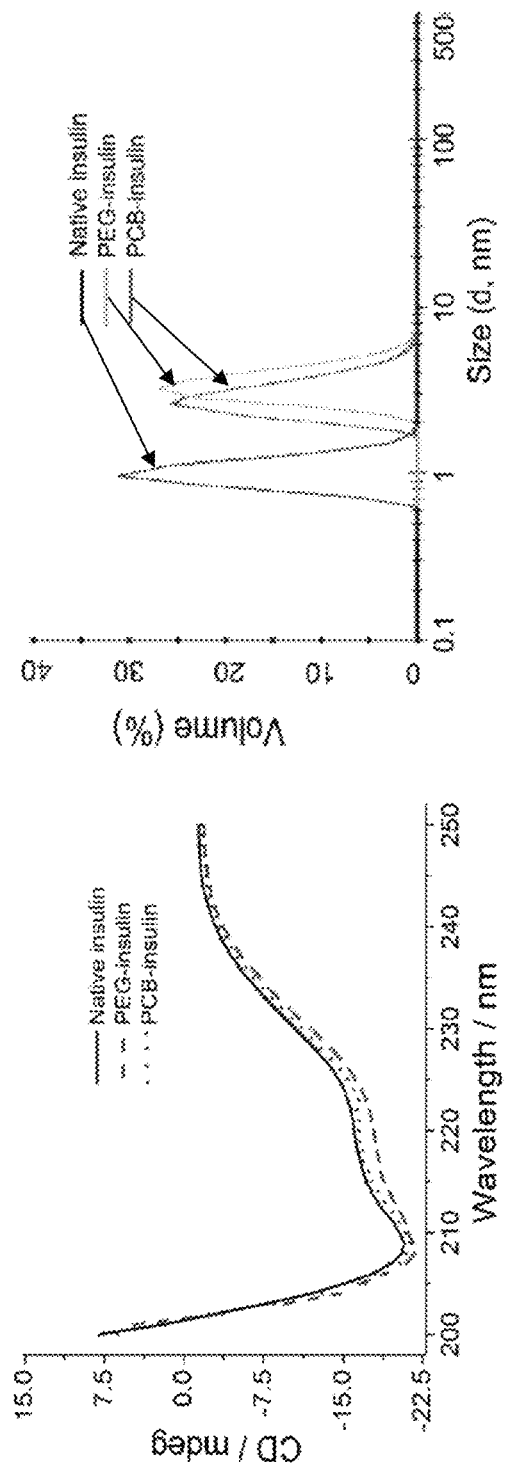
FIG. 3A is a graph showing far-ultraviolet circular dichroism (CD) spectra of free insulin, PCB-insulin conjugate and PEG-insulin conjugate, wherein the CD spectrum of PCB-insulin shows an evident decrease of the negative peak at 222 nm, indicating the increase of α-helix structure.
FIG. 3B is a graph showing results of analysis of the hydrodynamic size of free insulin, PEG-conjugated insulin, and PCB-conjugated insulin measured by a dynamic light scattering (DLS) method using a Malvern Nano-ZS Zetasizer.

The effect of polymer conjugation on the structure change of insulin was evaluated. Far-ultraviolet CD spectra were collected to quantify the effect of the zwitterionic polymer conjugation on insulin's secondary structure. The spectra of free and conjugated insulins, 0.2 mg/mL insulin or conjugates in 0.2 M pH 8.2 PBS buffer, are shown in FIG. 3A. The quantified results of secondary structures in different samples are shown in Table 1. It was found that the percentage of α-helix structure for PEG-insulin is 46%, and is a slightly less than that for free insulin which is 50%. The random coil structure proportion for PEG-insulin is 30%, and is more than 24% for free insulin. The CD spectrum of PCB-insulin shows an evident decrease of the negative peak at 222 nm, indicating the increase of α-helix structure, FIG. 3A.

The quantified results show that the α-helix structure proportion of PCB-insulin is 53% (slightly more than 50% of free insulin), and the random coil structure proportion of PCB-insulin is 23% (a little less than 24% of free insulin), Table 1.

TABLE 1

The secondary structure proportion of insulin samples

| | α-helix | β-structure (β-turn and β-sheet) | Random coil |
| --- | --- | --- | --- |
| Free insulin | 50% | 26% | 24% |
| PEG-insulin | 46% | 24% | 30% |
| PCB-insulin | 53% | 24% | 23% |

Thus, the conjugation of PCB has a moderate stabilizing effect on the secondary structure of insulin implicating retention of insulin bioactivity after PCB conjugation.

Results show that one-PCB-chain modification per insulin at LysB29 obtained from simple, regular conjugation chemistry shows improved pharmacokinetics, retained in vitro bioactivity and remarkably increased in vivo pharmacological activity of lowering blood glucose.

Hydrodynamic Size of PCB-Insulin

The hydrodynamic size of PCB-conjugated insulin was measured by a dynamic light scattering (DLS) method by using a Malvern Nano-ZS Zetasizer. Representative results are shown in FIG. 3B. The hydrodynamic sizes of free insulin, PEG-insulin and PCB-insulin in pH 8.4 0.2M HEPES buffer are 1.4±0.2 nm, 4.2±0.7 nm and 3.7±0.6 nm, respectively (average±standard deviation, n=3). There is a significant hydrodynamic size increase for PCB-insulin, implicating a potential protracted blood circulating life time for PCB-insulin.

Bioavailability and Blood Circulation Characteristics of PCB-Insulin

To evaluate the bioavailability of the insulin conjugates, free insulin (human, recombinant) PCB-insulin or PEG-insulin was injected intravenously into streptozotocin (STZ) induced diabetic mice. Blood glucose concentration was monitored by measurement at various time points following injection of free insulin, PCB-insulin or PEG-insulin.

Non-purified PCB-insulin or non-purified PEG-insulin, each containing both conjugated and unconjugated insulin, were administered to the mice for comparison with administration of free insulin alone. The injection dose for the three samples were readily kept the same at 10 nmol/Kg insulin or its conjugate (for native insulin dose, 10 nmol/kg=1.5 IU/kg), by accurately controlling the feeding molar content of insulin for the conjugation reaction.

It was found that blood glucose lowering abilities of PEG-insulin and native insulin, as reflected by the relative intensity of blood glucose concentration, are similar, FIG. 4A. Unexpectedly, PCB-insulin shows significantly higher blood glucose lowering ability than native insulin, FIG. 4A. The data are presented as the percentage of the initial values of blood glucose concentration.

Purified PCB-insulin or purified PEG-insulin was administered to the mice for comparison with administration of free insulin alone. The injection dose for free insulin purified PCB-insulin and purified PEG-insulin were kept the same at 10 nmol/kg, by quantifying the insulin molar content using both UV-vis absorbance method and ELISA kit.

The purified PEG-insulin did not show any better glucose lowering effect than native insulin as shown in FIG. 4B, similar to the result in FIG. 4A. However, unexpectedly, the purified zwitterionic PCB-insulin sample had even higher blood glucose lowering ability than native insulin as shown in FIG. 4B, and its non-purified form as well, compare FIGS. 4A and 4B. The data are presented as the percentage of the initial values of blood glucose concentration.

The in vivo bioavailability of insulin samples was evaluated by quantifying the area above the curve (AAC) of relative intensity of blood glucose concentration in FIG. 4B. The bioavailability of PEG-insulin is about 97.5% comparing with that of free insulin, while PCB-insulin is about 124.3%. This indicates the effect of PCB conjugation to insulin significantly increases the in vivo bioavailability of insulin.

FIG. 4C shows the bioactivity of native insulin, rough PEG-insulin, purified PEG-insulin, rough PCB-insulin and purified PCB-insulin, respectively, as measured by phosphorylation of the insulin receptor in vitro. The relative activity was presented as the percentage relative to native insulin±standard deviation (n=6) * p<0.05, ** p<0.01, ns=not significant. FIG. 4C shows that there was no significant decrease in the in vitro bioactivity of both the rough and purified zwitterionic PCB-insulin, while a significant decrease of in vitro activity of PEG-insulin was observed. The purified PEG-insulin lost about 27% activity in vitro compared with native insulin.

Figure 4D:
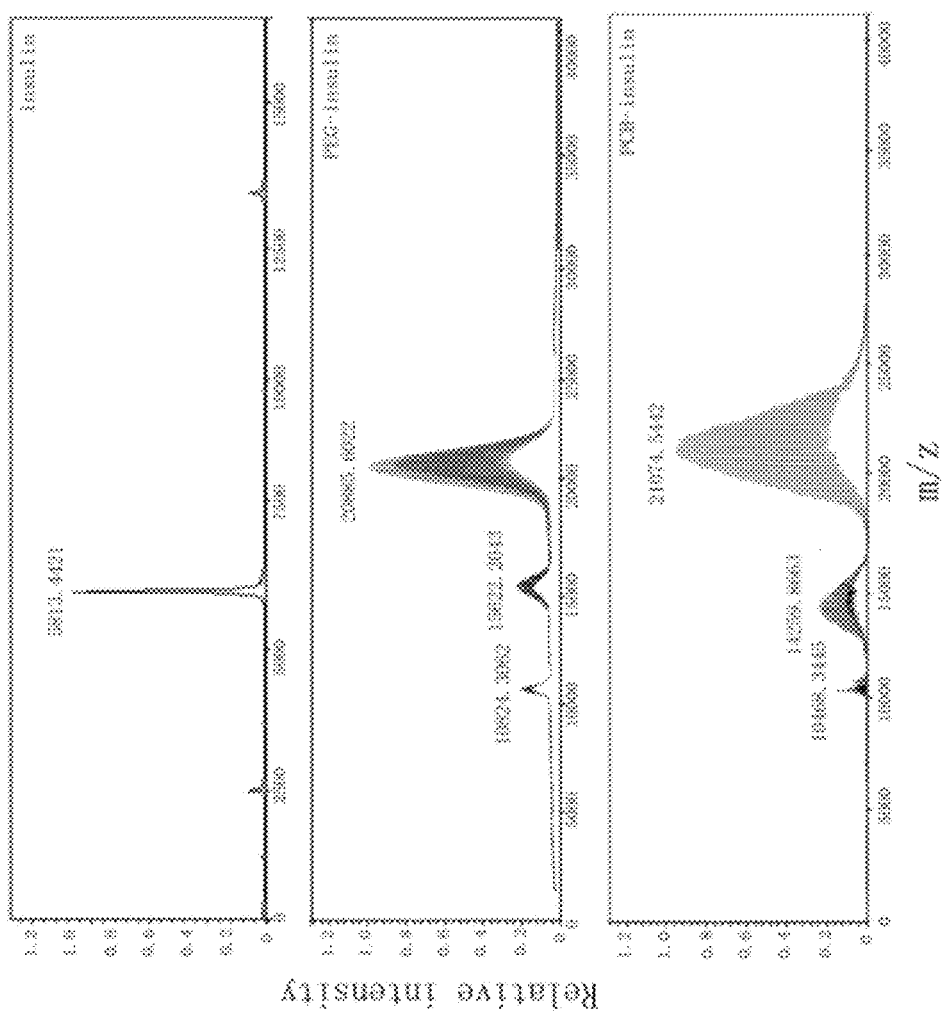
FIG. 4D is a set of graphs showing MALDI-TOF Mass spectra of native insulin, purified PEG-insulin and purified PCB-insulin where most of the three amines of insulin were conjugated with PEG or PCB.

FIG. 4D is a set of graphs showing MALDI-TOF Mass spectra of native insulin, purified PEG-insulin and purified PCB-insulin where most of the three amine of insulin were conjugated with PEG or PCB.

Figure 4E:
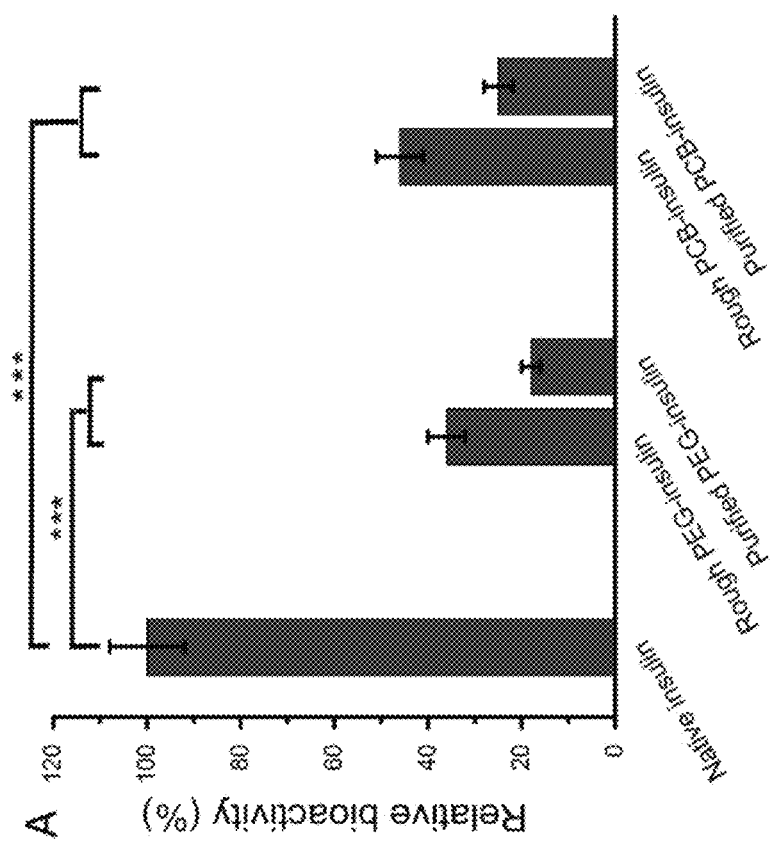
FIG. 4E is a graph showing the bioactivity of native insulin, rough (non-purified) PEG-insulin, purified PEG-insulin, rough (non-purified) PCB-insulin and purified PCB-insulin, respectively, as measured by phosphorylation of the insulin receptor in vitro.

FIG. 4E is a graph showing the bioactivity of native insulin, rough PEG-insulin, purified PEG-insulin, rough PCB-insulin and purified PCB-insulin, respectively, as measured by phosphorylation of the insulin receptor in vitro. For the polymer-insulin tested, most of the three amines were conjugated with PEG or PCB. The relative activity was presented as the percentage relative to native insulin±standard deviation (n=6) *** p<0.001.

Figure 4F:
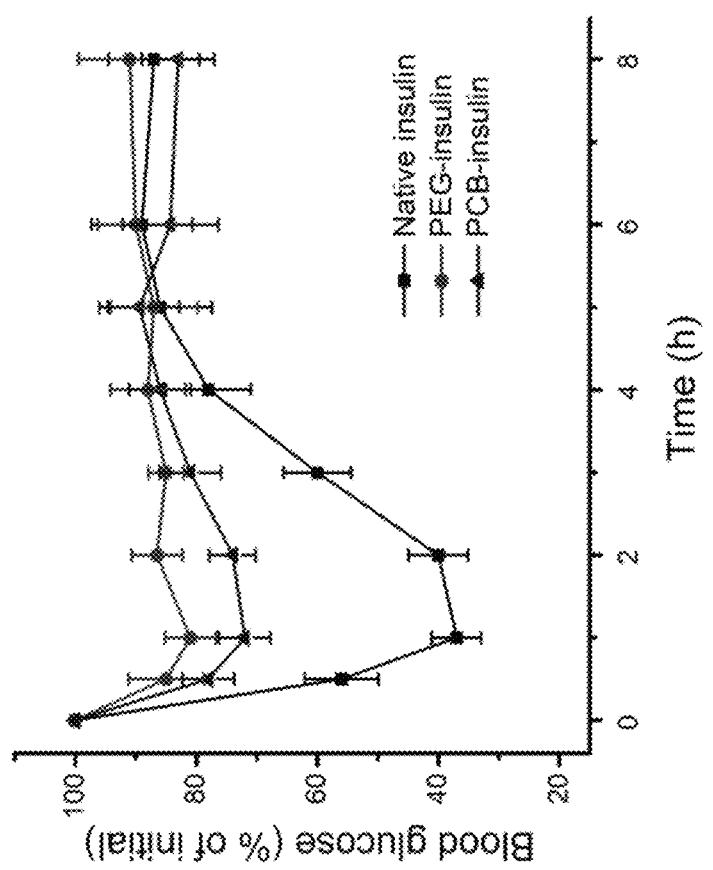
FIG. 4F is a graph showing the relative blood glucose concentration as a function of time after the tail vein injection of free insulin, rough (non-purified) PEG-insulin, and rough (non-purified) PCB-insulin (before purifying insulin conjugate products)

FIG. 4F is a graph showing the relative blood glucose concentration as a function of time after the tail vein injection of free insulin, rough PEG-insulin, and rough PCB-insulin (before purifying insulin conjugate products). For the polymer-insulin tested, most of the three amines were conjugated with PEG or PCB. The data are presented as the percentage of the initial values of blood glucose concentration±standard deviation (n=6).

Figure 5:
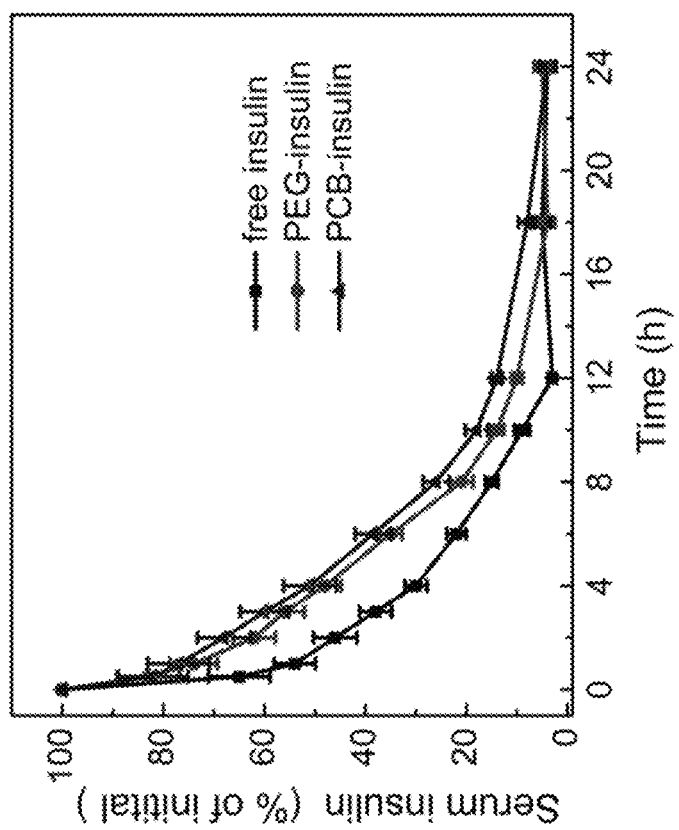
FIG. 5 is a graph showing the concentration of serum insulin as a function of time following the intravenous injection of free insulin, PCB-insulin or PEG-insulin to diabetic mice.

After intravenously administering free insulin, PCB-insulin or PEG-insulin to diabetic mice, blood samples were collected at various time intervals and the concentration of insulin was quantified with human insulin ELISA assay. The concentration of serum insulin as a function of time following the injection was plotted in FIG. 5. For the polymer-insulin tested in this figure, the acylation is at any of the three amines (GlyA1, PheB1, or LysB29), but prioritized at epsilon amine of LysB29. The data are presented as the percentage of the initial values of serum insulin concentration.

The relative area under the curve (AUC) was calculated and the blood circulation half-life ($t_{1/2}$) was obtained to fit a one compartment model, Table 2.

TABLE 2

The relative area under the curve (AUC) and elimination half-life ($t_{1/2}$) of free insulin, PCB-insulin or PEG-insulin in blood serum. Data are illustrated by average ± standard deviation, n = 3.

|  | Relative area under the curve (AUC) | Half-life elimination time ($t_{1/2}$) (h) |
|---|---|---|
| Free insulin | 341 ± 24 | 2.0 ± 0.3 |
| PEG-insulin | 447 ± 30 | 3.6 ± 0.3 |
| PCB-insulin | 466 ± 34 | 4.2 ± 0.3 |

The AUCs for both PCB-insulin and PEG-insulin are larger than that of native insulin. The relative AUC for PCB-insulin is almost 1.43 times of that of native insulin. $t_{1/2}$ for PCB-insulin (4.2 h) and PEG-insulin (3.6 h) are significantly longer than free insulin (2 h), indicating the prolonged blood circulation effect upon polymer conjugation.

A glucose-responsive zwitterionic PCB-insulin macrogel according to aspects of the present disclosure is obtained by physically mixing component (A) and (B).

Insulin Release Profile Upon Glucose Challenge

The obtained glucose-responsive zwitterionic PCB-insulin macrogels are subjected to different glucose challenge patterns (glucose set-point, kinetic, and cycling experiments) at 37° C. and tested for insulin release. Insulin amount released are quantified via a human insulin ELISA assay kit (Mercodia, Uppsala, SE). For set-point study, macrogels are continuously incubated with 50, 100, 200, 400, 800, and 1600 mg/dl glucose solution each for 1 h. Cumulative insulin released after each of the challenge is recorded. The glucose concentration corresponding to 10% ($G_{10\%}$) and 50% insulin release ($G_{50\%}$) is calculated. $G_{10\%}$>100 mg/dl and $G_{50\%}$>350 mg/dl are preferred so that the macrogel will not over release insulin at hypoglycemic glucose level (<70 mg/dl). For kinetic study, insulin release is monitored over time up to 5 h in 50, 100, and 400 mg/dl glucose solution; this is to validate the ability to release basal amount of insulin at hypo- and normo-glycemic level, and to rapidly release insulin at high glucose level. For cycling study, macrogel is repeatedly treated with 100 and 400 mg/dl glucose solution each for 1 h up to 4 cycles with released polymer-insulin quantified over time; this is to verify whether the macrogels can sustain cycled glucose challenge and reverse insulin release, which is the prerequisite for long-term blood glucose control. To evaluate whether the macrogels are physically durable (not dissolved so quickly) for long-term implantation, they will be placed at 100 mg/dl glucose and monitored for their weight loss over time.

Example 2

Materials and Methods

Synthesis of Mannose Monomer 137.5 mg (0.5 mmol) 4-aminophenyl α-D-mannopyranoside and 70 μl (0.5 mmol) triethylamine were dissolved in 2 ml DMF with an ice bath. Add 60 ul (0.75 mmol)acryloyl chloride to the mixture dropwise. After 2 hours' reaction at room temperature, centrifuge the mixture to remove undissolved triethylamine hydrochloride. Transfer the supernatant to anhydrous chloroform to obtain precipitates. Wash the precipitates with ethyl ether and dried the product under vacuum.

Synthesis of Insulin Monomer 4.26 mg DCC and 2.38 mg NHS and 20.67 μmol 2-carboxyethyl acrylate were dissolved in 1 ml THF and stirred for 4 hours. In another vial, 100 mg insulin was dissolved in 0.1 M NaHCO$_3$ solution. The THF mixture was transferred into the vial and reacted for 2 hours. 6N HCl was then added to the mixture and vaporize THF. The residue solution was dialyzed and lyophilized to obtain insulin monomer powder. Typically, the yield is 24.6%.

Preparation of Concanavalin a Monomer

Concanavalin A was dissolved in BES buffer in an ice bath. Acryloyl chloride was add dropwise into the system and stirred continuously for 3 hours. The whole mixture was then dialyzed and lyophilized to obtain the product. To prepare FITC labeled concanavalin A monomer, 1 mg fluorescein-5-isothiocyanate isomer was added to 100 mg Con A monomer solution and stirred for 24 hours. The obtained solution was dialyzed to remove unreacted fluorescein isomer.

Polymerization to Produce Component A 50 mg CBAA monomer, 30 mg mannose monomer and 20 mg insulin monomer were dissolved in 3 ml water. 2 mg ammonium persulfate (APS) was added and the polymerization reaction mixture was stirred for 1 hour at 37 degrees Celsius. The reacted mixture was then dialyzed and lyophilized to obtain the product.

Glucose-Responsive Zwitterionic Polymer-Insulin-Saccharide Composition Preparation Prepare 50 mg/ml Con A solution and 10 mg/ml Component A. Add 0.5 ml Con A solution into 0.5 ml Component A solution dropwise and wait for 1 hour, producing the glucose-responsive zwitterionic polymer-insulin-saccharide composition suspended in aqueous solvent.

Hydrogel Encapsulated Glucose-Responsive Zwitterionic Polymer-Insulin-Saccharide Composition Preparation (Glucose-Responsive Zwitterionic Polymer-Insulin-Saccharide Composition with Hydrogel Carrier)

Use the suspended the glucose-responsive zwitterionic polymer-insulin-saccharide composition in aqueous solvent from the step above to dissolve 800 mg CBAA monomer, 5 mg MBAA crosslinker, 8 mg APS, and transfer the resulting reaction mixture into silicone molds immediately. After 1 hour incubation at 37 degrees Celsius, the resulting hydrogel, also called a "macrogel" herein, was transferred into sterilized PBS to equilibrate for 2 days and then hydrogel disks with 0.5 cm diameter were generated using an appropriately sized punch.

Component B Immobilization

To synthesize the glucose-responsive zwitterionic polymer-insulin-saccharide composition, wherein the saccharide binding molecule is covalently bonded to a second polymer or a hydrogel.

Synthesis protocols to obtain a glucose-responsive zwitterionic polymer-insulin-saccharide composition comprising ConA and a reaction product of a zwitterionic CBAA monomer, an insulin-containing monomer and a mannose-containing monomer as component A, wherein ConA is non-leachable by covalently immobilizing it to a second polymer or a hydrogel ConA monomer synthesis. 50 mg ConA and 84 mg NaHCO$_3$ were dissolved in BES buffer with an ice bath, and 80 ul acryloyl chloride was added dropwise to the mixture. The reaction was kept for 3 hours under stirring. Resulting product ConA monomer was obtained after dialysis against water and lyophilization.

Synthesis protocols to obtain a glucose-responsive zwitterionic polymer-insulin-saccharide composition comprising ConA and a reaction product of a zwitterionic CBAA monomer, an insulin-containing monomer and a mannose-containing monomer as component A, wherein ConA is non-leachable by covalently immobilizing it to a hydrogel 0.5 ml of 50 mg/ml ConA monomer solution plus 0.5 ml of 10 mg/ml component A solution in water was used to dissolve 800 mg CBAA monomer, 5 mg MBAA crosslinker, and 8 mg APS through vortex and the mixture was transferred into a silicone mold immediately. After 1 hour reaction at 37° C., a hydrogel was formed and transferred into sterilized PBS to equilibrate for 1 day. Hydrogel disks with 0.5 cm diameter were punched out for further use.

Alternatively, a water solution was obtained containing 50 mg/ml ConA monomer and 5 mg/ml glucose solution. 0.5 ml of this solution was added into 0.5 ml of 10 mg/ml component A solution in a dropwise manner. After 1 hour, 800 mg CBAA monomer, 5 mg MBAA crosslinker, 8 mg APS were added into the mixture, and the mixture was transferred into a silicone mold immediately. After 1 hour reaction at 37 C° C., a hydrogel was formed and transferred into sterilized PBS to equilibrate for 1 day. Hydrogel disks with 0.5 cm diameter were punched out for further use.

Alternatively, 800 mg CBAA monomer, 5 mg MBAA crosslinker, 8 mg APS were dissolved in 0.5 ml water plus 0.5 ml of 50 mg/ml ConA monomer solution. The mixture was transferred into a silicone mold immediately. After 1 hour reaction at 37° C., a hydrogel was formed and transferred into sterilized PBS to equilibrate for 1 day. Hydrogel disks with 0.5 cm diameter were pouched out and were further equilibrated in PBS for a week (PBS was frequently refreshed). To load component A into this ConA-containing matrix, the hydrogel was equilibrated with PBS containing 5 mg/ml glucose for two hours, then with PBS containing 5 mg/ml glucose and 10 mg/ml component A for 12 hours. Then the hydrogel with component A absorbed was placed in 1 L of regular PBS for two hours and was ready for further use.

Synthesis protocols to obtain a glucose-responsive zwitterionic polymer-insulin-saccharide composition comprising ConA and a reaction product of a zwitterionic CBAA monomer, an insulin-containing monomer and a mannose-containing monomer as component A, wherein ConA is non-leachable by covalently immobilizing it to a second polymer.

600 mg CBAA monomer, and 6 mg APS were dissolved in 0.5 ml of 50 mg/ml ConA monomer solution, and incubated at 37° C. for 1 hour. Then 0.5 ml of 10 mg/ml component A solution, 200 mg CBAA monomer, 5 mg MBAA crosslinker, 2 mg APS were added into the previous solution. The mixture was transferred into a silicone mold immediately. After 1 hour reaction at 37° C., a hydrogel was formed and transferred into sterilized PBS to equilibrate for 1 day. Hydrogel disks with 0.5 cm diameter were pouched out for further use.

Synthesis with the Hydrogel Carrier:

Synthesis of a novel glucose-responsive zwitterionic polymer-insulin conjugate of a reaction product of a zwitterionic CBAA monomer, an insulin-containing monomer and a mannose-containing monomer as component A, further encapsulated by zwitterionic PCBAA chemical hydrogel.

0.5 ml of 10 mg/ml Component A plus 0.5 ml water was used to dissolve 800 mg CBAA monomer, 5 mg MBAA crosslinker, and 8 mg APS. The mixture was transferred into a silicone mold immediately. After 1 hour reaction at 37° C., a hydrogel was formed and transferred into sterilized PBS to equilibrate for 2 days. Hydrogel disks with 0.5 cm diameter were pouched out before further use.

Synthesis of a novel glucose-responsive zwitterionic polymer-insulin conjugate comprising ConA and a reaction product of a zwitterionic CBAA monomer, an insulin-containing monomer and a mannose-containing monomer as component A, further encapsulated by zwitterionic PCBAA chemical hydrogel.

0.5 ml of 50 mg/ml ConA solution was added into 0.5 ml of 10 mg/ml component A solution in a dropwise manner and 1 hour was allowed for the two molecules to complete interaction. The suspended mixture was used to dissolve 800 mg CBAA monomer, 5 mg MBAA crosslinker, and 8 mg APS. The mixture was transferred into a silicone mold immediately. After 1 hour reaction at 37° C., a hydrogel was formed and transferred into sterilized PBS to equilibrate for 2 days. Hydrogel disks with 0.5 cm diameter were pouched out before further use.

Synthesis of Glucose-Responsive Hydrogel Carrier or Barrier:

Synthesis of a novel glucose-responsive hydrogel carrier or barrier comprising a reaction product of a zwitterionic CBAA monomer, a mannose-containing monomer, and a ConA-containing monomer, for glucose-responsive release of insulin, or zwitterionic polymer-insulin-saccharide compositions according to aspects of the present disclosure A water solution was obtained containing 50 mg/ml ConA monomer and 5 mg/ml glucose solution. 0.5 ml of this solution was added into 0.5 ml of 3 mg/ml mannose monomer solution containing 5 mg/ml glucose in a dropwise manner. After 1 hour, 600 mg CBAA monomer, and 6 mg APS were added into the mixture, and the reaction was kept at 37° C. for 1 hour. The resulting solution was dialyzed against 5 mg/ml glucose solution for a day then PBS for half a day. A physical hydrogel formed when ConA-mannose interaction was established as glucose was removed.

Synthesis of a novel glucose-responsive hydrogel carrier or barrier comprising a reaction product of a zwitterionic CBAA monomer, a mannose-containing monomer, a ConA-containing monomer, and a MBAA crosslinker, for glucose-responsive release of insulin, or zwitterionic polymer-insulin-saccharide compositions according to aspects of the present disclosure.

0.5 ml of 50 mg/ml ConA monomer solution containing 5 mg/ml glucose plus 0.5 ml of 3 mg/ml mannose monomer solution containing 5 mg/ml glucose in water was used to dissolve 800 mg CBAA monomer, 5 mg MBAA crosslinker, and 8 mg APS through vortex and the mixture was transferred into a silicone mold immediately. After 1 hour reaction at 37° C., a chemical and physical hydrogel was formed and transferred into 5 mg/ml glucose solution and then sterilized PBS to equilibrate for 1 day and a half day, respectively, before further use.

Glucose-Set Point Test and Other In Vitro Tests

Glucose set-point (GSP) is a method to evaluate the accuracy of insulin retention/release when the hydrogel encapsulated glucose-responsive zwitterionic polymer-insulin-saccharide composition was challenged by a given glucose concentration. In a typical testing procedure, the composition was incubated in different concentration glucose solution (100, 200, 300, 400, 500, 600, 800, and 1600 mg/dL respectively) for 1 hour. The cumulative released insulin is quantified using a human insulin ELISA assay. Usually the cumulative released insulin after challenge with highest concentration of glucose solution was normalized as 100%. The glucose concentration corresponding to 10% (G10%) insulin release and 50% (G50%) are chosen to characterize these two points, respectively. Generally, G10%>100 mg/dL and G50%>350 mg/dL are preferred. By meeting this requirement, the composition will not "over-release" insulin at hypoglycemic glucose level but will release insulin at high (hyperglycemic) blood glucose level.

Insulin release kinetics were tested at different concentration glucose solution (100 mg glucose/dL, 400 mg glucose/dL) for up to 24 hours. At fixed time intervals, 1 ml sample of solution was extracted and the insulin concentration was measured.

Insulin release under hypoglycemic and hyperglycemic conditions was also measured. The hydrogel encapsulated glucose-responsive zwitterionic polymer-insulin-saccharide composition was alternatively immersed in 100 mg/dL glucose and 400 mg/dL glucose every 1 hour. 1 ml sample of each solution was extracted each hour and the insulin concentration was measured.

Bioactivity of Modified Insulin

In vitro bioactivity of modified insulin in Component A was tested using a cell-based protein kinase B phosphorylation assay. Briefly, 25000 CHO-M1 cells per well (American Type Culture Collection, ATCC) were seeded in a 96-well tissue culture treated plate and incubated for 24 hours before being cultured in serum-free medium overnight. These cells were then treated with 50 μL of native insulin, modified insulin for 45 min. The effective insulin concentration in each of the sample was maintained at 2 nmol mL-1. Then treated cells were lysed, and a commercially available kit (Cisbio) was used to assay phosphorylated AKT at Ser473.

Validate of Anti-Fibrosis and Vascularization-Promoting Capabilities.

Glucose responsive zwitterionic PCB-insulin macrogels will be s.c. implanted in both healthy (C57BL/6 mice) and diabetic mice (streptozotocin (STZ)-induced C57BL/6 mice) to evaluate their resistance to fibrotic tissue deposition, and the ability to promote new blood vessel formation. Two formulations from each type of macrogel (two types using the two mannose monomers respectively), a total of four formulations, are used in both healthy and diabetic mice.

For implantation surgery, mice will receive meloxicam analgesia and be anesthetized under isoflurane inhalation (inducted in a chamber and maintained via a nose cone). Appropriate anesthesia levels are monitored by observing respiration rate, eye response, and response to front toe pinch. The surgical site (dorsal skin) is shaved and prepped with three alternating scrubs of betadine and alcohol. On each prepped animal, a single incision is made through dorsal skin. One subcutaneous pocket is created by blunt dissection through the incision for placement of one macrogel sample. The wound is then closed with wound clips ¼" apart, which will be removed within two weeks. Surgeries are conducted with animal on a warm pad. After 2 weeks, 1 month and 3 months implantation, macrogels with surrounding tissues are explanted, fixed in zinc fixative overnight and embedded in paraffin wax for sectioning. They will be stained with hematoxylin & eosin (H&E) for cell structures, Masson's trichrome for fibrotic collagen formation, and anti-MECA-32 for blood vessel formation.

Evaluation of the bioavailability of Component A and long-term glucose control of the implant in diabetic mice.

In vitro bioactivity for Component A compared with native insulin is tested using an insulin receptor activation assay.

About 25,000 CHO-M1 cells/well (ATCC) were seeded in a 96-well tissue culture treated plate and incubate for 24 h before being cultured in serum-free medium. These cells were then treated with 10 μg/mL native insulin, PEG-insulin, and PCB-insulin samples, respectively, for 45 minutes. The effective insulin concentration in each of the samples was maintained at 2 nmol/mL. Then cells were lysed and a commercially available kit (Cisbio) was used to assay phosphorylated AKT at Ser473. The fluorescence emission at 665 and 620 nm was measured on a HTRF reader (BioTek, USA).

In vivo bioavailability of component A is tested by s.c. injection at 10 nmol/kg into STZ mice, and blood glucose concentration at pre-determined time points (within 24 h) is monitored and bioavailability for component A (AAC relative to that of native insulin) is obtained.

Long-term blood glucose control is determined by s.c. implanting the glucose-responsive zwitterionic PCB-insulin macrogel (four formulations) in diabetic STZ mice at day 0. The animals' weight and blood is sampled three times a week until the endpoint. To test blood glucose, 5 μl blood drops are collected from the tails using a lancet and tested using a commercial glucometer. Typically, the mice blood glucose is expected to drop from minutes to hours after the implantation, which will be closely monitored. Mice with blood glucose below 200 mg/dL are considered normoglycemic.

Statistical Analysis

Examination and quantification of histological images will be done by three independent researchers blinded to sample identity with at least five random images in each section on two sections per animal. A two-tailed Student's t-test will be used for all statistical analyses, with $P<0.05$ being considered as statistically significant.

Results

Figure 9A:
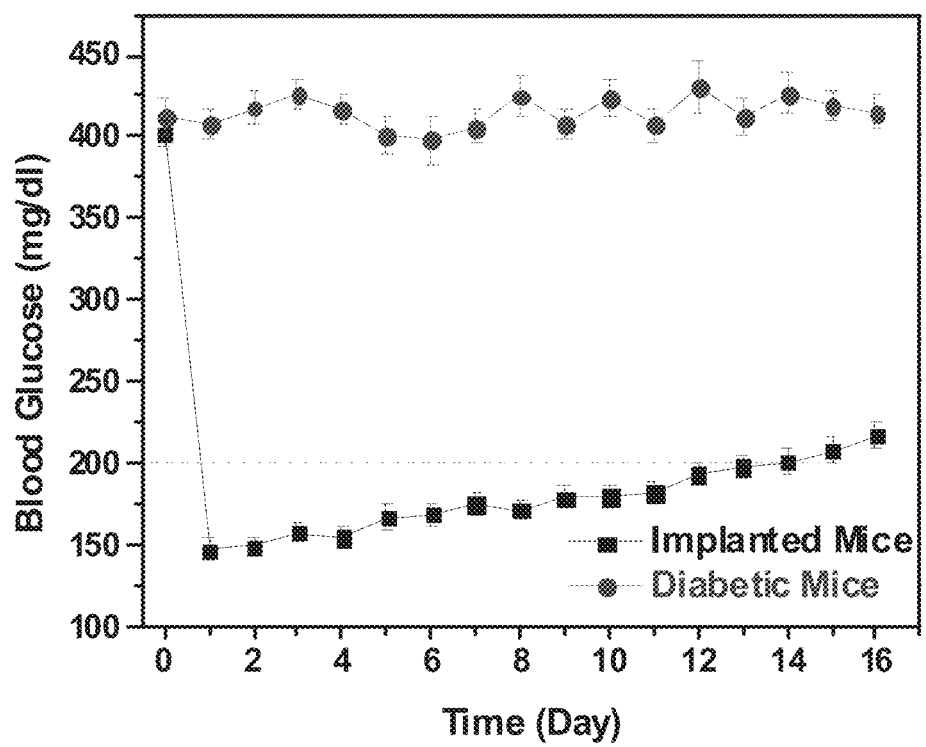
FIG. 9A is a graph showing results of blood glucose monitoring of mice implanted with the glucose-responsive zwitterionic PCB-insulin macrogel after surgery compared with diabetic mice.
Figure 9B:
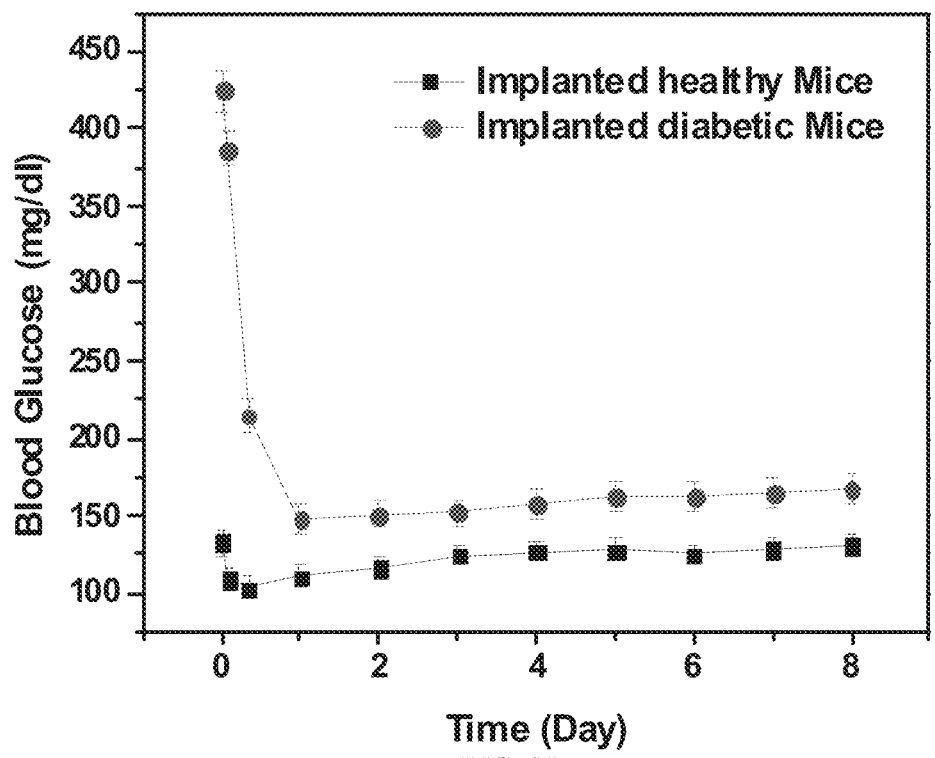
FIG. 9B is a graph showing that no hypoglycemia was observed in healthy mice after implantation of the glucose-responsive zwitterionic PCB-insulin macrogel.
Figure 9C:
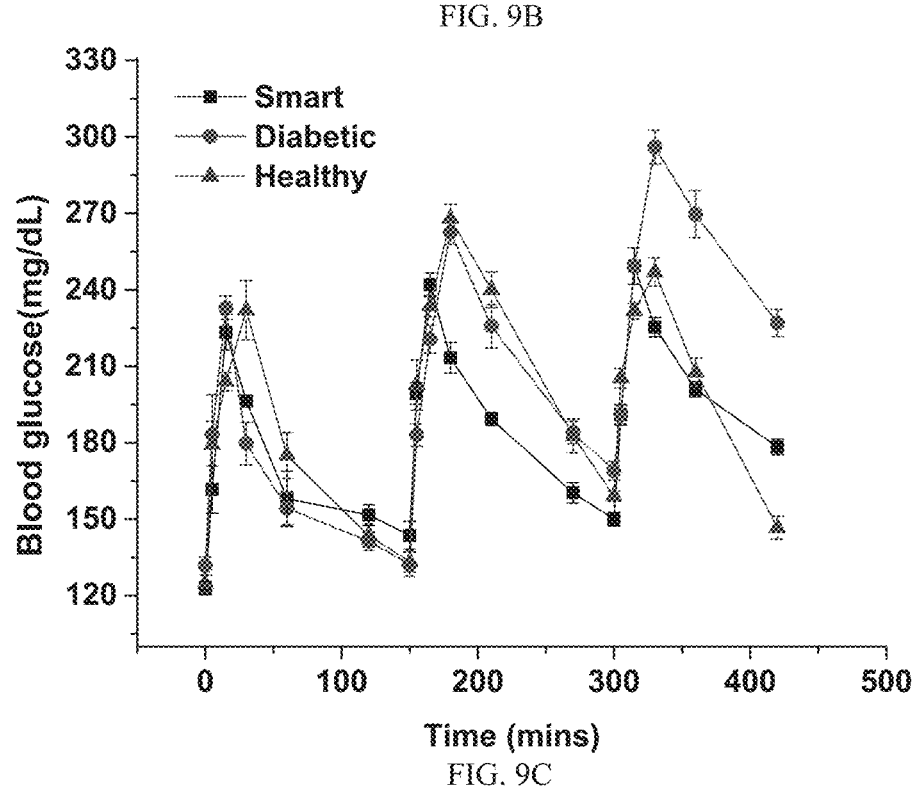
FIG. 9C is a graph showing results of continual IPGTT testing for both diabetic mice with and without the glucose-responsive zwitterionic PCB-insulin macrogel implantation and healthy mice.
Figure 9D:
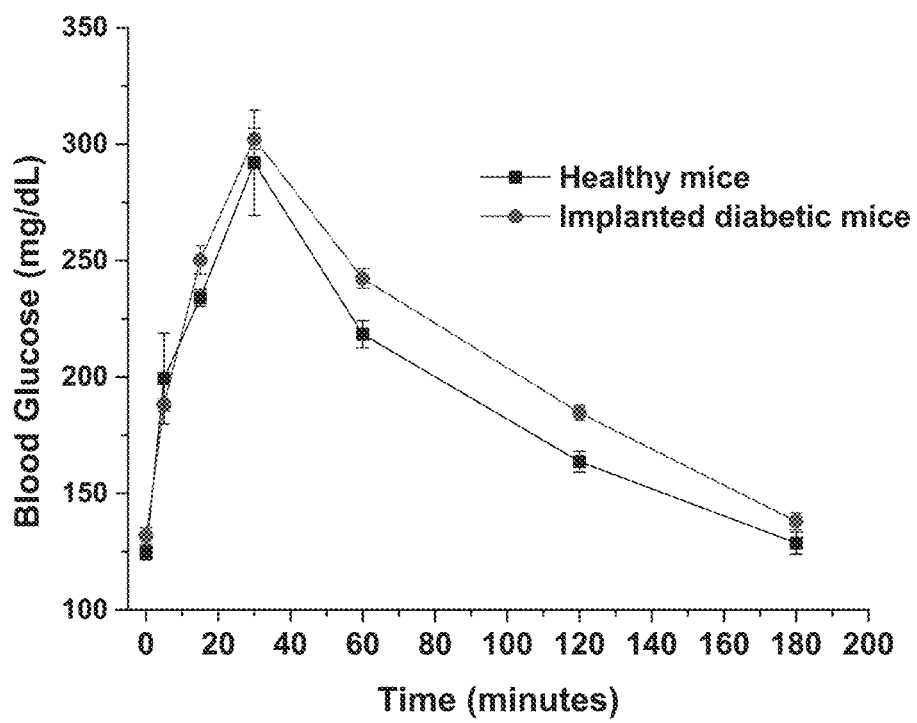
FIG. 9D is a graph showing results of an IPGTT test on day 3 post implantation of the glucose-responsive zwitterionic PCB-insulin macrogel.
Figure 9E:
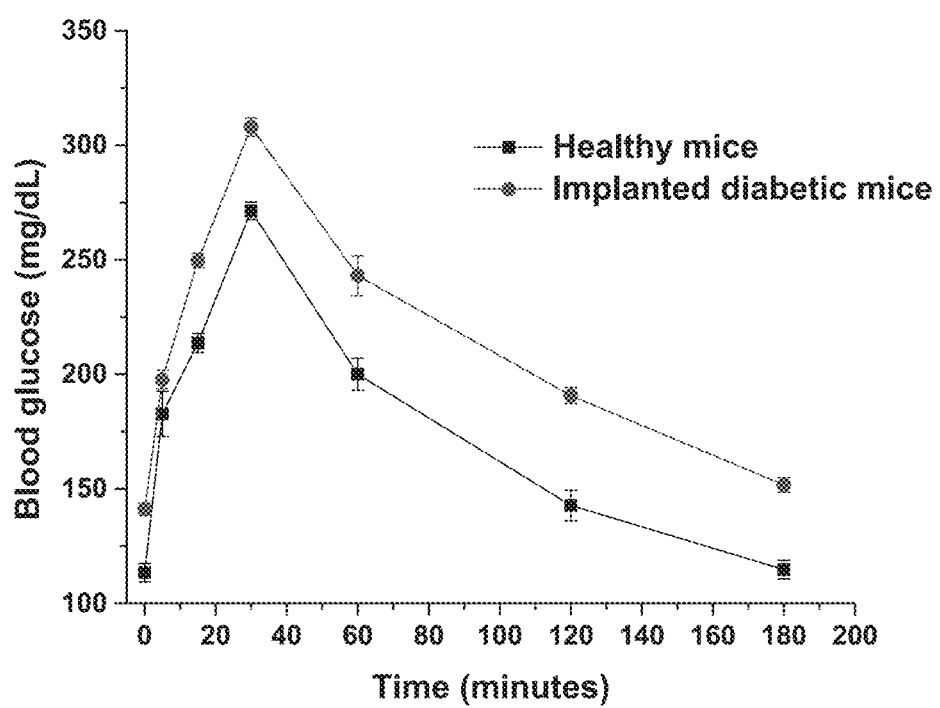
FIG. 9E is a graph showing results of an IPGTT test on day 6 post implantation of the glucose-responsive zwitterionic PCB-insulin macrogel.
Figure 9F:
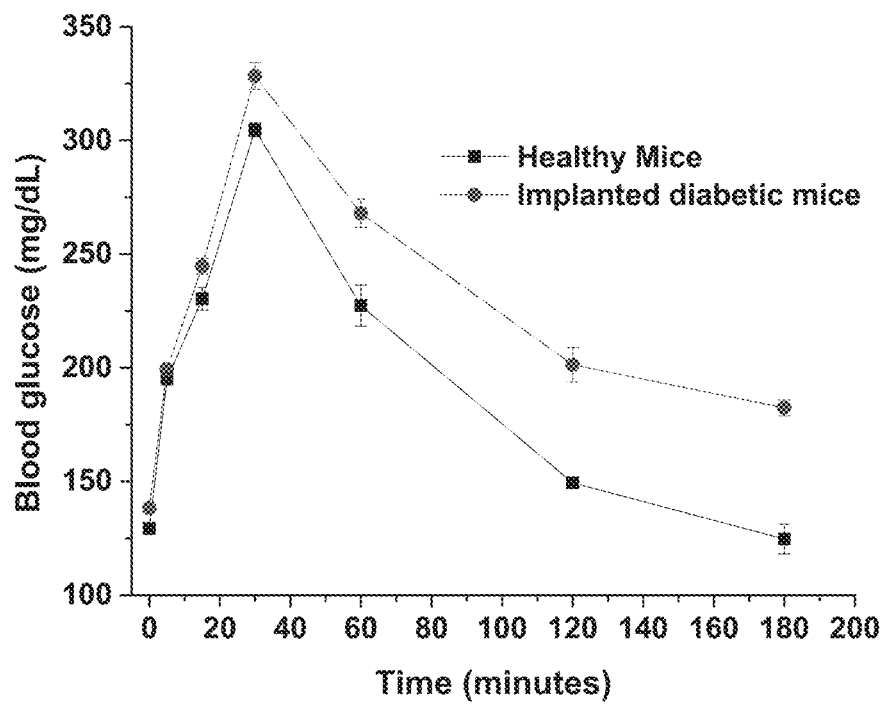
FIG. 9F is a graph showing results of an IPGTT test on day 9 post implantation of the glucose-responsive zwitterionic PCB-insulin macrogel.

A glucose-responsive zwitterionic PCB-insulin macrogel used in this example is based on mannose/glucose-Concavalin A (Con A) binding competition which includes Component A and Component B wherein: Component (A) is zwitterionic PCB polymer with insulin and mannose attached, and Component B is Con A (type VI), shown schematically in FIGS. 6 and 7. Con A can bind with mannose or glucose, so the interactions of a complex formed by physically mixing components A and B is significantly influenced by ambient glucose concentration. Thus, a hydrogel containing mannose-Con A complex of the present disclosure is gradually swelled as glucose concentration rises and releases insulin-containing Component A from the complex. When the concentration of ambient glucose decreases, the complex shrinks and gradually stops releasing insulin.

In this example, Component A was synthesized by random free radical co-polymerization of PCB monomers, human recombinant insulin monomers and mannose monomers as side chains, respectively. This method produces a high molecular weight zwitterionic polymer-insulin-saccharide composition, enables the PCB, insulin, and mannose in the composition to be finely tuned according to the desired ratios of each, and, in preferred embodiments, does not involve any toxic catalysts (e.g., present in living polymerization methods).

To test the bioactivity of the insulin moiety in Component A, Component A was incubated with cells and its bioactivity was measured as 88.3% of native insulin using an Insulin Bioactivity Kit. Compared with native insulin, the insulin moiety in Component A didn't lose any significant bioactivity.

After physically mixing Component A and Component B, a glucose-responsive zwitterionic polymer-insulin-saccharide composition was formed by interaction of mannose incorporated in the zwitterionic polymer-insulin-saccharide composition (Component A) with the ConA (Component B) such that a mannose-Con A binding complex (glucose-responsive zwitterionic polymer-insulin-saccharide composition) formed and precipitated in the solution. The precipitated glucose-responsive zwitterionic polymer-insulin-saccharide composition was then resuspended in a zwitterionic monomer-containing pre-gel solution and an encapsulated glucose-responsive zwitterionic PCB-insulin "macrogel" was obtained by encapsulation of the glucose-responsive zwitterionic polymer-insulin-saccharide composition into chemically crosslinked zwitterionic hydrogel.

Con A was also crosslinked to avoid any leaching from the macrogel. To verify there is no leaching of Con A from the macrogel, FITC labeled crosslinked Con A was used to prepare the macrogel and the macrogel was incubated for 2 days. No characteristic absorbance peak of FITC was observed on UV-Vis spectrum, which showed there is no Con A leaching from the macrogel.

Before implantation into a mouse, the glucose-responsive zwitterionic PCB-insulin macrogel was subjected to a series of different glucose challenges to test insulin release kinetics. To plot the insulin release curve, the glucose-responsive zwitterionic PCB-insulin macrogel was incubated with 100, 200, 300, 400, 500, 600, 800 and 1600 mg/dl glucose solution each for 1 h. 25 ul samples were extracted and released insulin was quantified via a Mercodia human insulin ELISA assay. Cumulative released insulin in the different glucose concentration solutions within 1 hour is shown in FIG. 8A. The glucose concentration corresponding to 10% (G10%) and 50% insulin release (G50%) was calculated to comply with preferred standard: G10%>100 mg/dl and G50%>350 mg/dl. This indicated that the glucose-responsive zwitterionic PCB-insulin macrogel quickly releases insulin at high glucose concentrations and only released trace insulin at low glucose concentrations.

Specially, 100 mg/dl and 400 mg/dl are typically upper and lower limit for normal glucose variation in human subjects. Insulin release from the glucose-responsive zwitterionic PCB-insulin macrogel was monitored for up to 24 hours in 100 and 400 mg/dl glucose solutions. The results shown in FIGS. 8A, 8B and 8C further validate the ability of the glucose-responsive zwitterionic PCB-insulin macrogel to release a basal amount of insulin at hypo- and normal-glycemic levels, and to rapidly release insulin at high glucose levels.

Since blood glucose levels in vivo vary from high level to low level, tests were performed to verify that the glucose-responsive zwitterionic PCB-insulin macrogel can sustain cycled glucose challenge and reverse insulin release. In this example, the glucose-responsive zwitterionic PCB-insulin macrogel was repeatedly treated with 100 and 400 mg/dl glucose solution each for 1 hour up to 4 cycles with released polymer-insulin quantified. Results in FIG. 8C demonstrated the quick response of the glucose-responsive zwitterionic PCB-insulin macrogel to varied glucose concentration, which is the prerequisite for long-term blood glucose control.

FIG. 8A is a graph showing a set-point curve of the glucose-responsive zwitterionic PCB-insulin macrogel and comparison with preferred standards; FIG. 8B is a graph showing insulin release kinetics of the glucose-responsive zwitterionic PCB-insulin macrogel during incubation in 100 mg/dl or 400 mg/dl; FIG. 8C is a graph showing results of a cycling test of the glucose-responsive zwitterionic PCB-insulin macrogel with repeatedly changed glucose concentration.

For in vivo testing, the glucose-responsive zwitterionic PCB-insulin macrogel was implanted subcutaneously in STZ induced diabetic mice and their blood glucose was monitored every day. Typically, 4 disks of the glucose-responsive zwitterionic PCB-insulin macrogel could control blood glucose at normal level as long as 2 weeks, see FIG. 9A. Each disk of the macrogel contained ~30 μg of insulin equivalent. Insulin dosage for each mouse receiving the implanted disks is 6 mg/kg.

Even after 2 weeks, blood glucose of mice with the glucose-responsive zwitterionic PCB-insulin macrogel implanted was only gradually increased rather than quickly returned to hyperglycemia. Such results indicate that the cause of blood glucose increase is only because the glucose-responsive zwitterionic PCB-insulin macrogel was almost run out of encapsulated modified insulin (Component A).

To test whether the basal insulin release at low glucose concentration could lead to hypoglycemia, normoglycemia mice were also implanted with the glucose-responsive zwitterionic PCB-insulin macrogel. Results in FIG. 9B showed that even healthy mice with implanted glucose-responsive zwitterionic PCB-insulin macrogel disk do not show any sign of hypoglycemia.

To challenge the ability to quickly respond to glucose change in the environment, IPGTTs (intraperitoneal glucose tolerance tests) were executed continually on a single day and on different days post-implantation of the glucose-responsive zwitterionic PCB-insulin macrogel. It was found that blood glucose of mice implanted with the glucose-responsive zwitterionic PCB-insulin macrogel would quickly rise due to the injection of glucose solution and gradually decrease to normal level due to the release of insulin moiety from the implanted glucose-responsive zwitterionic PCB-insulin macrogel in response to increased blood glucose FIG. 9A is a graph showing results of blood glucose monitoring of mice implanted with the glucose-responsive zwitterionic PCB-insulin macrogel after surgery compared with diabetic mice. FIG. 9B is a graph showing that no hypoglycemia was observed in healthy mice after implantation of the glucose-responsive zwitterionic PCB-insulin macrogel. FIG. 9C is a graph showing results of continual IPGTT testing for both diabetic mice with and without the glucose-responsive zwitterionic PCB-insulin macrogel implantation and healthy mice. The glucose challenge dose is 1 g/kg through i.p. injection. Diabetic mice without implantation received a 5 IU/kg insulin through s.c. injection 1 hour prior to IPGTT test. FIG. 9D is a graph showing results of an IPGTT test on day 3 post implantation of the glucose-responsive zwitterionic PCB-insulin macrogel. The glucose challenge dose is 1 g/kg through i.p. injection. FIG. 9E is a graph showing results of an IPGTT test on day 6 post implantation of the glucose-responsive zwitterionic PCB-insulin macrogel. The glucose challenge dose is 1 g/kg through i.p. injection. FIG. 9F is a graph showing results of an IPGTT test on day 9 post implantation of the glucose-responsive zwitterionic PCB-insulin macrogel. The glucose challenge dose is 1 g/kg through i.p. injection.

Figure 10A:
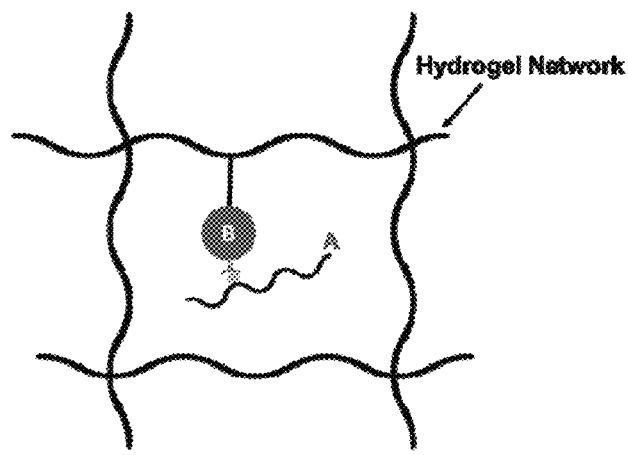
FIG. 10A is a schematic diagram of a glucose-responsive zwitterionic polymer-insulin-saccharide composition, wherein the saccharide binding molecule is covalently bonded to a hydrogel; "A" indicates Component A and "B" indicates Component B wherein Component A and Component B are bound via specific interaction of a saccharide moiety of Component A and the saccharide binding molecule which is Component B.
Figure 10B:
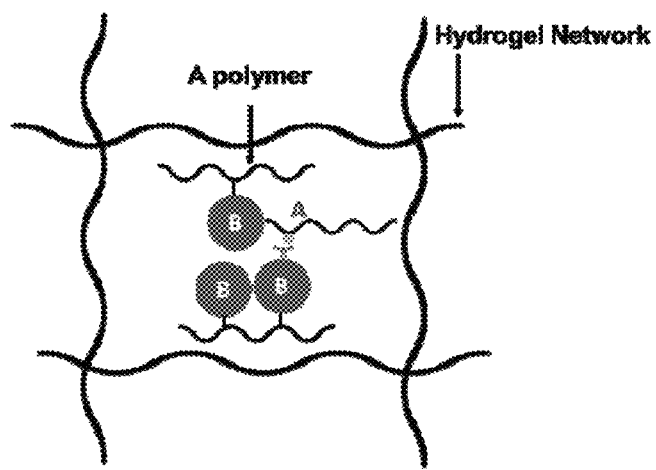
FIG. 10B is a schematic diagram of a glucose-responsive zwitterionic polymer-insulin-saccharide composition, wherein the saccharide binding molecule is covalently bonded to a second polymer and the composition is encapsulated in a hydrogel and/or the second polymer is covalently bonded to the hydrogel; "A" indicates Component A and "B" indicates Component B wherein Component A and Component B are bound via specific interaction of a saccharide moiety of Component A and the saccharide binding molecule which is Component B.

FIG. 10A is a schematic diagram of a glucose-responsive zwitterionic polymer-insulin-saccharide composition, wherein the saccharide binding molecule is covalently bonded to a hydrogel; "A" indicates Component A and "B" indicates Component B wherein Component A and Component B are bound via specific interaction of a saccharide moiety of Component A and the saccharide binding molecule which is Component B;

FIG. 10B is a schematic diagram of a glucose-responsive zwitterionic polymer-insulin-saccharide composition, wherein the saccharide binding molecule is covalently bonded to a second polymer and the composition is encapsulated in a hydrogel and/or the second polymer is covalently bonded to the hydrogel; "A" indicates Component A and "B" indicates Component B wherein Component A and Component B are bound via specific interaction of a saccharide moiety of Component A and the saccharide binding molecule which is Component B.

Items

Item 1. A zwitterionic polymer-insulin-saccharide composition, comprising: a zwitterionic polymer covalently bonded to an insulin moiety, and covalently bonded to a saccharide moiety.

Item 2. The zwitterionic polymer-insulin-saccharide composition of item 1, comprising a polymerization reaction product of a zwitterionic monomer, an insulin-containing monomer, and a saccharide-containing monomer.

Item 3. The zwitterionic polymer-insulin-saccharide composition of item 1 or item 2, wherein the zwitterionic monomer has the structural formula:

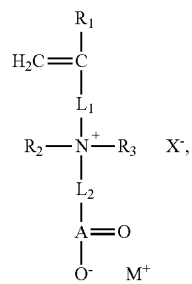

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; $X^-$ is a counter ion associated with the cationic center; and $M^+$ is a metal cation, an ammonium cation, or an organic cation.

Item 4. The zwitterionic polymer-insulin-saccharide composition of item 2 or 3, wherein the zwitterionic monomer is selected from the group consisting of: carboxybetaine acrylamide; carboxybetaine methacrylate; carboxybetaine methacrylamide; carboxybetaine acrylate; carboxybetaine vinyl; sulfobetaine acrylamide; sulfobetaine methacrylate; sulfobetaine methacrylamide; sulfobetaine acrylate; sulfobetaine vinyl; phosphobetaine acrylamide; phosphobetaine methacrylate; phosphobetaine methacrylamide; phosphobetaine acrylate; phosphobetaine vinyl; and two or more thereof Item 5. The zwitterionic polymer-insulin-saccharide composition of any of items 2 to 4 wherein the insulin monomer comprises a terminal acryloyl functional group, the zwitterionic monomer comprises a terminal acryloyl functional group, and the saccharide monomer comprises a terminal acryloyl functional group.

Item 6. The zwitterionic polymer-insulin-saccharide composition of any of items 1-5 wherein the saccharide moiety or saccharide monomer comprises a saccharide selected from the group consisting of: mannose, fucose, a bisaccharide, a trisaccharide, a tetrasaccharide, a branched trisaccharide, bimannose, trimannose, tetramannose, branched trimannose, glucosamine, a derivative of any thereof, and a combination of any two or more thereof.

Item 7. The zwitterionic polymer-insulin-saccharide composition of any of items 1-6 wherein the saccharide moiety or saccharide monomer comprises mannose.

Item 8. The zwitterionic polymer-insulin-saccharide composition of any of items 1 to 7, further comprising a pharmaceutically acceptable carrier.

Item 9. A glucose-responsive zwitterionic polymer-insulin-saccharide composition, comprising, in combination: a saccharide binding molecule; and the zwitterionic polymer-insulin-saccharide composition of any of items 1 to 8, wherein the saccharide binding molecule binds to the saccharide of the zwitterionic polymer-insulin-saccharide composition.

Item 10. The glucose-responsive zwitterionic polymer-insulin-saccharide composition of item 9 wherein the saccharide binding molecule is a lectin, a saccharide binding fragment thereof or a combination of any two or more thereof.

Item 11. The glucose-responsive zwitterionic polymer-insulin-saccharide composition of item 9 or 10, wherein the saccharide binding molecule is mannose selective or fucose selective.

Item 12. The glucose-responsive zwitterionic polymer-insulin-saccharide composition of item of any of items 9 to 11, wherein the saccharide binding molecule is selected from the group consisting of: human mannose binding protein (MBP), human mannose receptors, human pulmonary surfactant protein A (SP-1), human pulmonary surfactant protein D, collectin-43, conglutinin, a phytohemagglutinin, human fucose binding protein, human fucose receptor, and exogenous lectins including but not limited to includes *Lotus tetragonolobus* lectin, *Ulex europaeus* agglutinin, *Lens* culimaris agglutinin, *Aleuria aurantia* lectin, *Anguilla* lectin, *Rhizopus stolonifera* lectin, *Ralstonia solanacearum* lectin, a saccharide binding fragment of any thereof, and a combination of any two or more thereof.

Item 13. The glucose-responsive zwitterionic polymer-insulin-saccharide composition of any of items 9 to 12 wherein the saccharide binding molecule is selected from the group consisting of: concanavalin A, a phytohemoagglutinin derived from *Galanthus nivalis* (snowdrop), *Pisum sativum* (pea), *Lathyrus odoratus* (sweet pea), *Lens culinaris* (lentil), *Narcissus pseudonarcissus* (daffodil), *Vicia faba* (fava bean), and *Vicia sativa* (garden vetch), a saccharide binding fragment of any thereof, and a combination of any two or more thereof.

Item 14. The glucose-responsive zwitterionic polymer-insulin-saccharide composition of any of items 9 to 13 wherein the saccharide binding molecule comprises two or more binding fragments of lectins covalently linked to each other.

Item 15. The glucose-responsive zwitterionic polymer-insulin-saccharide composition of any of items 9 to 14 wherein the saccharide binding molecule is a human saccharide binding molecule.

Item 16. The glucose-responsive zwitterionic polymer-insulin-saccharide composition of any of items 9 to 15 wherein the saccharide binding molecule is a non-human saccharide binding molecule.

Item 17. The glucose-responsive zwitterionic polymer-insulin-saccharide composition of any of items 9 to 16 wherein the saccharide binding molecule is Concavalin A and the saccharide is mannose.

Item 18. The glucose-responsive zwitterionic polymer-insulin-saccharide composition of any of items 9 to 17, wherein the ratio of the saccharide binding molecule to the zwitterionic polymer-insulin-saccharide composition is in the range of 0.001:1-1:0.001.

Item 19. The glucose-responsive zwitterionic polymer-insulin-saccharide composition of any of items 9 to 18, wherein the saccharide binding molecule is covalently bonded to a second polymer or a hydrogel wherein the second polymer comprises a zwitterionic polymer or zwitterionic repeating unit and/or the hydrogel comprises a zwitterionic polymer or zwitterionic repeating unit.

Item 20. The glucose-responsive zwitterionic polymer-insulin-saccharide composition of any of items 9 to 19 in the form of a gel.

Item 21. The glucose-responsive zwitterionic polymer-insulin-saccharide composition of any of items 9 to 20, further comprising a hydrogel carrier, where the glucose-responsive zwitterionic polymer-insulin-saccharide composition is encapsulated by the hydrogel carrier, producing a hydrogel encapsulated glucose-responsive zwitterionic polymer-insulin-saccharide composition.

Item 22. The glucose-responsive zwitterionic polymer-insulin-saccharide composition of item 21, wherein the hydrogel carrier comprises a zwitterionic polymer or zwitterionic repeating unit.

Item 23. The glucose-responsive zwitterionic polymer-insulin-saccharide composition of any of items 20 to 22, wherein the gel is in the form of particles having a particle diameter or longest dimension in the range of 1 nm to 50 cm.

Item 24. The glucose-responsive zwitterionic polymer-insulin-saccharide composition of any of items 9 to 23, further comprising a pharmaceutically acceptable carrier.

Item 25. A zwitterionic polymer-insulin composition.

Item 26. The zwitterionic polymer-insulin composition of item 25, wherein the composition comprises a reaction product selected from the group consisting of: a (poly)carboxybetaine polymer comprising reactive groups that react with primary amines, and insulin; a (poly)sulfobetaine polymer comprising reactive groups that react with primary amines, and insulin; and a (poly)phosphobetaine polymer comprising reactive groups that react with primary amines, and insulin.

Item 27. The zwitterionic polymer-insulin composition of item 26, wherein the (poly)carboxybetaine polymer comprising reactive groups that react with primary amines is selected from the group consisting of: (poly)carboxybetaine acrylamide comprising reactive groups that react with primary amines; (poly)carboxybetaine methacrylate comprising reactive groups that react with primary amines; (poly)carboxybetaine methacrylamide comprising reactive groups that react with primary amines; (poly)carboxybetaine acrylate comprising reactive groups that react with primary amines; (poly)carboxybetaine vinyl comprising reactive groups that react with primary amines; (poly)sulfobetaine acrylamide comprising reactive groups that react with primary amines; (poly)sulfobetaine methacrylate comprising reactive groups that react with primary amines; (poly)sulfobetaine methacrylamide comprising reactive groups that react with primary amines; (poly)sulfobetaine acrylate comprising reactive groups that react with primary amines; (poly)sulfobetaine vinyl comprising reactive groups that react with primary amines; (poly)phosphobetaine acrylamide comprising reactive groups that react with primary amines; (poly)phosphobetaine methacrylate comprising reactive groups that react with primary amines; (poly)phosphobetaine methacrylamide comprising reactive groups that react with primary amines; (poly)phosphobetaine acrylate comprising reactive groups that react with primary amines; (poly)phosphobetaine vinyl comprising reactive groups that react with primary amines; and any two or more thereof.

Item 28. The zwitterionic polymer-insulin composition of item 26 or item 27, wherein the reactive groups that react with primary amines are selected from the group consisting of: isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters.

Item 29. The zwitterionic polymer-insulin composition of any of items 25 to 28, wherein the composition comprises a reaction product of an NHS ester terminated (poly)carboxybetaine polymer and insulin.

Item 30. The zwitterionic polymer-insulin composition of any of items 25 to 29, wherein the composition comprises a reaction product of insulin and an NHS ester terminated (poly)carboxybetaine polymer selected from the group consisting of: NHS ester terminated (poly)carboxybetaine acrylamide; NHS ester terminated (poly)carboxybetaine methacrylate; NHS ester terminated (poly)carboxybetaine methacrylamide; NHS ester terminated (poly)carboxybetaine acrylate; NHS ester terminated (poly)carboxybetaine vinyl; NHS ester terminated (poly)sulfobetaine acrylamide; NHS ester terminated (poly)sulfobetaine methacrylate; NHS ester terminated (poly)sulfobetaine methacrylamide; NHS ester terminated (poly)sulfobetaine acrylate; NHS ester terminated (poly)sulfobetaine vinyl; NHS ester terminated (poly)phosphobetaine acrylamide; NHS ester terminated (poly)phosphobetaine methacrylate; NHS ester terminated (poly)phosphobetaine methacrylamide; NHS ester terminated (poly)phosphobetaine acrylate; NHS ester terminated (poly)phosphobetaine vinyl; and two or more thereof.

Item 31. The zwitterionic polymer-insulin composition of any of items 25 to 30, wherein the composition comprises a reaction product of: a (poly)carboxybetaine polymer comprising reactive groups that react with primary amines; and insulin.

Item 32. The zwitterionic polymer-insulin composition of item 25 comprising:
a polymerization reaction product of a zwitterionic monomer and an insulin-containing monomer.

Item 33. The zwitterionic polymer-insulin composition of item 32, wherein the zwitterionic monomer has the structural formula:

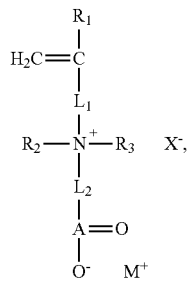

where $R_1$, $R_2$, and $R_3$ are each independently selected from hydrogen, alkyl, and aryl groups; $L_1$ is a linker that covalently couples a cationic center to a polymer backbone; $L_2$ is a linker that covalently couples the cationic center to an anionic group; $A(=O)O^-$ is the anionic group; $X^-$ is the counter ion associated with the cationic center; and $M^+$ is a metal cation, an ammonium cation, or an organic cation.

Item 34. The zwitterionic polymer-insulin composition of item 32 or 33, wherein the zwitterionic monomer is selected from the group consisting of: carboxybetaine acrylamide; carboxybetaine methacrylate; carboxybetaine methacrylamide; carboxybetaine acrylate; carboxybetaine vinyl; sulfobetaine acrylamide; sulfobetaine methacrylate; sulfobetaine methacrylamide; sulfobetaine acrylate; sulfobetaine vinyl; phosphobetaine acrylamide; phosphobetaine methacrylate; phosphobetaine methacrylamide; phosphobetaine acrylate; phosphobetaine vinyl; and two or more thereof Item 35. The zwitterionic polymer-insulin composition of any of items 32 to 24 wherein the insulin monomer comprises a terminal acryloyl functional group.

Item 36. A hydrogel carrier or barrier for glucose-responsive release of insulin, comprising a zwitterionic polymer, a saccharide, and a saccharide binding molecule.

Item 37. A method of treatment of a subject in need of insulin, comprising: administering a composition selected from the group consisting of: a zwitterionic polymer-insulin composition, a zwitterionic polymer-insulin-saccharide composition, a glucose-responsive zwitterionic polymer-insulin composition, and a combination of any two or more thereof, of any of items 1 to 36.

Item 38. The method of item 37, wherein the subject is human.

Item 39. The method of item 37 or 38, wherein the subject has type 1 diabetes, type 2 diabetes, gestational diabetes or pre-diabetes.

Item 40. A medical device comprising a composition selected from the group consisting of: a zwitterionic polymer-insulin composition, a zwitterionic polymer-insulin-saccharide composition, a glucose-responsive zwitterionic polymer-insulin composition, and a combination of any two or more thereof, according to any of items 1 to 39.

Item 41. The medical device of item 40 wherein the glucose-responsive zwitterionic polymer-insulin-saccharide composition is in gel form.

Item 42. The conjugate, composition, device or method of any one or more of the above items wherein the zwitterionic polymer-insulin conjugate comprises a zwitterionic polymer conjugated to at least one insulin amino acid residue selected from the group consisting of: GlyA1, PheB2 and LysB29.

Item 43. The conjugate, composition, device or method of any one or more of the above items wherein the zwitterionic polymer-insulin conjugate is (poly)carboxybetaine polymer-insulin, (poly)sulfobetaine polymer-insulin, or (poly)phosphobetaine polymer-insulin, wherein the (poly)carboxybetaine polymer-insulin, (poly)sulfobetaine polymer-insulin or (poly)phosphobetaine polymer-insulin comprises (poly)carboxybetaine polymer, (poly)sulfobetaine polymer or (poly)phosphobetaine polymer conjugated to LysB29.

Item 44. The conjugate, composition, or method of any one or more of the above items wherein the zwitterionic polymer-insulin conjugate is (poly)carboxybetaine polymer-insulin, (poly)sulfobetaine polymer-insulin or (poly)phosphobetaine polymer-insulin wherein the (poly)carboxybetaine polymer-insulin, (poly)sulfobetaine polymer-insulin or (poly)phosphobetaine polymer-insulin comprises (poly)carboxybetaine polymer, (poly)sulfobetaine polymer or (poly)phosphobetaine polymer conjugated to at least one insulin amino acid residue selected from the group consisting of: GlyA1, PheB2 and LysB29.

Item 45. The conjugate, composition, device or method of any one or more of the above items wherein the zwitterionic polymer-insulin conjugate is (poly)carboxybetaine polymer-insulin, (poly)sulfobetaine polymer-insulin or (poly)phosphobetaine polymer-insulin, wherein the (poly)carboxybetaine polymer-insulin, (poly)sulfobetaine polymer-insulin or (poly)phosphobetaine polymer-insulin comprises (poly)carboxybetaine polymer, (poly)sulfobetaine polymer or (poly)phosphobetaine polymer conjugated to LysB29.

Item 46. The conjugate, composition, or method of any one or more of the above items wherein the zwitterionic polymer-insulin conjugate comprises a mixture of a zwitterionic polymer-insulin conjugates including zwitterionic polymer conjugated to insulin at LysB29, zwitterionic polymer conjugated to insulin at PheB2 and zwitterionic polymer conjugated to insulin at GlyA1, wherein 50% or more of the zwitterionic polymer-insulin conjugates in the mixture comprise zwitterionic polymer conjugated to insulin at LysB29.

Item 47. The conjugate, composition, or method of any one or more of the above items wherein the zwitterionic polymer-insulin conjugate comprises a mixture of a zwitterionic polymer-insulin conjugates including (poly)carboxybetaine polymer conjugated to insulin at LysB29, (poly)carboxybetaine polymer conjugated to insulin at PheB2 and (poly)carboxybetaine polymer conjugated to insulin at GlyA1, wherein 50% or more of the zwitterionic polymer-insulin conjugates in the mixture comprise (poly)carboxybetaine polymer conjugated to insulin at LysB29.

Item 48. The conjugate, composition, or method of any one or more of the above items wherein the zwitterionic polymer-insulin conjugate comprises a mixture of a zwitterionic polymer-insulin conjugates including (poly)sulfobetaine polymer conjugated to insulin at LysB29, (poly) sulfobetaine polymer conjugated to insulin at PheB2 and (poly)sulfobetaine polymer conjugated to insulin at GlyA1, wherein 50% or more of the zwitterionic polymer-insulin conjugates in the mixture comprise (poly)sulfobetaine polymer conjugated to insulin at LysB29.

Item 49. The conjugate, composition, or method of any one or more of the above items wherein the zwitterionic polymer-insulin conjugate comprises a mixture of a zwitterionic polymer-insulin conjugates including (poly)phosphobetaine polymer conjugated to insulin at LysB29, (poly) phosphobetaine polymer conjugated to insulin at PheB2 and (poly)phosphobetaine polymer conjugated to insulin at GlyA1, wherein 50% or more of the zwitterionic polymer-insulin conjugates in the mixture comprise (poly)phosphobetaine polymer conjugated to insulin at LysB29.

Item 50. The conjugate, composition, device or method of any one or more of the above items wherein the zwitterionic polymer-insulin conjugate comprises native human insulin conjugated to a zwitterionic polymer.

Item 51. The conjugate, composition, device or method of any one or more of the above items wherein the zwitterionic polymer-insulin conjugate comprises an insulin analog selected from the group consisting of: insulin glulisine, insulin lispro, insulin aspart, insulin glargine, insulin detemir, insulin isophane, GLP-1, and a GLP-1 agonist, conjugated to a zwitterionic polymer.

Item 52. A composition comprising insulin substantially as described herein.

Item 53. A method of treating a subject in need of insulin substantially as described herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Any patents or publications mentioned in this specification are incorporated herein by reference to the same extent as if each individual publication is specifically and individually indicated to be incorporated by reference.

The compositions and methods described herein are presently representative of embodiments, exemplary, and not intended as limitations on the scope of the disclosure. Changes therein and other uses will occur to those skilled in the art. Such changes and other uses can be made without departing from the scope of the disclosure as set forth in the claims.

The invention claimed is:

1. A composition, comprising:
   a zwitterionic polymer-insulin-saccharide composition comprising a zwitterionic polymer-insulin composition covalently bonded to a saccharide moiety or a saccharide monomer; and
   a lectin in physical mixture with the zwitterionic polymer-insulin-saccharide composition, wherein the lectin binds to the saccharide of the zwitterionic polymer-insulin-saccharide composition, forming a glucose-responsive zwitterionic polymer-insulin-saccharide composition.

2. The composition of claim 1, further comprising a hydrogel carrier, where the glucose-responsive zwitterionic polymer-insulin-saccharide composition is encapsulated by the hydrogel carrier, forming a hydrogel encapsulated glucose-responsive zwitterionic polymer-insulin-saccharide composition.

* * * * *